United States Patent
Qin et al.

(10) Patent No.: US 12,318,457 B2
(45) Date of Patent: Jun. 3, 2025

(54) OLIGOSACCHARIDE LINKER, LINKER-PAYLOAD COMPRISING THE SAME AND GLYCAN CHAIN-REMODELED ANTIBODY-DRUG CONJUGATE, PREPARATION METHODS AND USES THEREOF

(71) Applicant: GENEQUANTUM HEALTHCARE (SUZHOU) CO., LTD., Suzhou (CN)

(72) Inventors: Gang Qin, Suzhou (CN); Meijun Xiong, Suzhou (CN); Mingyu Hu, Suzhou (CN)

(73) Assignee: GENEQUANTUM HEALTHCARE (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 18/469,292

(22) Filed: Sep. 18, 2023

(65) Prior Publication Data
US 2024/0082419 A1    Mar. 14, 2024

Related U.S. Application Data

(63) Continuation of application No. PCT/CN2023/098081, filed on Jun. 2, 2023.

(30) Foreign Application Priority Data

Jun. 2, 2022 (CN) .................. 202210625988.5
Jun. 2, 2022 (CN) .................. 202210629801.9
Mar. 30, 2023 (WO) ............... PCT/CN2023/085098

(51) Int. Cl.
| A61K 47/68 | (2017.01) |
|---|---|
| A61K 47/54 | (2017.01) |
| A61K 47/65 | (2017.01) |
| A61P 35/00 | (2006.01) |

(52) U.S. Cl.
CPC ........ *A61K 47/6889* (2017.08); *A61K 47/549* (2017.08); *A61K 47/65* (2017.08); *A61K 47/68031* (2023.08); *A61K 47/68033* (2023.08); *A61K 47/68035* (2023.08); *A61K 47/68037* (2023.08); *A61K 47/6805* (2017.08); *A61K 47/6809* (2017.08); *A61K 47/6811* (2017.08); *A61P 35/00* (2018.01)

(58) Field of Classification Search
CPC .. A61K 31/7016; A61K 47/549; A61K 47/65; A61P 35/00
See application file for complete search history.

(56) References Cited

U.S. PATENT DOCUMENTS

| 9,175,326 | B2 | 11/2015 | Wang |
|---|---|---|---|
| 9,850,473 | B2 | 12/2017 | Wang |
| 9,884,123 | B2 * | 2/2018 | Sengupta ............... A61K 47/00 |
| 10,836,815 | B2 | 11/2020 | Wang et al. |
| 10,851,174 | B2 | 12/2020 | Wang et al. |
| 11,459,380 | B2 | 10/2022 | Wang et al. |
| 11,559,581 | B2 | 1/2023 | Davis et al. |
| 11,643,450 | B2 | 5/2023 | Wang et al. |
| 11,834,688 | B2 | 12/2023 | Qin et al. |
| 11,845,970 | B2 | 12/2023 | Wang et al. |
| 12,012,582 | B2 | 6/2024 | Qin et al. |
| 2012/0226024 | A1 | 9/2012 | Wang et al. |
| 2020/0323995 | A1 * | 10/2020 | Satomaa ............ A61K 47/6809 |
| 2023/0355791 | A1 * | 11/2023 | Van Delft ........ A61K 47/68037 |
| 2024/0197900 | A1 | 6/2024 | Huang et al. |

FOREIGN PATENT DOCUMENTS

| CN | 104220603 A | 12/2014 | |
|---|---|---|---|
| CN | 109071630 A | 12/2018 | |
| CN | 114395051 A | 4/2022 | |
| CN | 114480115 A | 5/2022 | |
| WO | WO-2007/133855 A2 | 11/2007 | |
| WO | WO-2013/120066 A1 | 8/2013 | |
| WO | WO-2018/039373 A1 | 3/2018 | |
| WO | WO2018036403 A1 * | 3/2018 | ............. C08B 37/00 |
| WO | WO-2020/006176 A1 | 1/2020 | |
| WO | WO-2022/174834 A1 | 8/2022 | |
| WO | WO-2022/226420 A2 | 10/2022 | |
| WO | 2024/002330 A1 | 1/2024 | |

OTHER PUBLICATIONS

Huang (WO2018036403 A1; machine English translation done on May 14, 2024).*
Boeggeman, E., et al. "Site specific conjugation of fluoroprobes to the remodeled Fc N-glycans of monoclonal antibodies using mutant glycosyltransferases: Application for cell surface antigen detection," Bioconjug Chem., vol. 20, No. 6, pp. 1228-1236, (2009).
Danishefsky, I., et al. "Investigations on the Chemistry Heparin V. Disaccharides Obtained after Partial Hydrolysis," Bioconjugate Chemistry, vol. 101, No. 1, pp. 37-45, (1965).
Dickgiesser, S., et al. "Site-Specific Conjugation of Native Antibodies Using Engineered Microbial Transglutaminases," Bioconjugate Chemistry, vol. 31, No. 4, pp. 1070-1076, (2020).

(Continued)

*Primary Examiner* — Pancham Bakshi
(74) *Attorney, Agent, or Firm* — Hoxie & Associates LLC

(57) ABSTRACT

The present disclosure further relates to a linker-payload compound including an oligosaccharide group, especially a disaccharide group, where the oligosaccharide group is linked to the remainder of the compound by an amide bond. The present disclosure further relates to an antibody-drug conjugate (ADC) containing the linker-payload compound, where the glycan chain in an antibody is remodeled with the oligosaccharide moiety in the linker-payload compound. The present disclosure further relates to preparation methods and use of the above-mentioned substances.

10 Claims, 16 Drawing Sheets

Specification includes a Sequence Listing.

(56) References Cited

OTHER PUBLICATIONS

Huang, W., et al. "Chemoenzymatic Glycoengineering of Intact IgG Antibodies for Gain of Functions," J Am Chem Soc., vol. 134, No. 29, pp. 12308-12318, (2012).

Li, X., et al. "Preparation of well-defined antibody-drug conjugates through glycan remodeling and strain-promoted azide-alkyne cycloadditions," Angew Chem Int Ed Engl., vol. 53, No. 28, pp. 7179-7182, (2014).

Van Geel, R., et al. "Chemoenzymatic Conjugation of Toxic Payloads to the Globally Conserved N-Glycan of Native mAbs Provides Homogeneous and Highly Efficacious Antibody-Drug Conjugates," Bioconjug Chem., vol. 26, No. 11, pp. 2233-2242, (2015).

Wang, L.-X., et al. "Glycoengineering of Antibodies for Modulating Functions," Annu Rev Biochem, vol. 88, pp. 433-459, (2019).

Zang, X., et al. "Synthesis and Evaluation of Three Azide-Modified Disaccharide Oxazolines as Enzyme Substrates for Single-Step Fc Glycan-Mediated Antibody-Drug Conjugation," Bioconjugate Chemistry, vol. 33, No. 6, pp. 1179-1191, (2022).

Zeng, Y., et al. "Recent advances in synthetic glycoengineering for biological applications," Curr Opin Biotechnol., vol. 74, pp. 247-255, (2022).

Zhang, X., et al. "General and Robust Chemoenzymatic Method for Glycan-Mediated Site-Specific Labeling and Conjugation of Antibodies: Facile Synthesis of Homogeneous Antibody-Drug Conjugates," ACS Chem Biol., vol. 16, No. 11, pp. 2502-2514, (2021).

Zhou, Q., et al. "Site-specific antibody-drug conjugation through glycoengineering," Bioconjug Chem., vol. 25, No. 3, pp. 510-520, (2014).

Zhu, Z., et al. "Site-specific antibody-drug conjugation through an engineered glycotransferase and a chemically reactive sugar," MAbs, vol. 6, No. 5, pp. 1190-1200, (2014).

Zuberbühler, K., et al. "Fucose-specific conjugation of hydrazide derivatives to a vascular-targeting monoclonal antibody in IgG format," Chem Commun, vol. 48, pp. 7100-7102, (2012).

Chuang, H. et al., "Development of biotinylated and magnetic bead-immobilized enzymes for efficient glyco-engineering and isolation of antibodies," Bioorganic Chemistry, vol. 112, (2021), Abstract Only, DOI: 10.1016/j.bioorg.2021.104863.

Shi, W. et al. "One-step synthesis of site-specific antibody-drug conjugates by reprograming IgG glycoengineering with LacNAc-based substrates," Acta Phamaceutica Sinica. B, vol. 12, No. 5, pp. 2417-2428, (2022), DOI: 10.1016/j.apsb.2021.12.013.

Parsons, T. et al., "Optimal Synthetic Glycosylation of a Therapeutic Antibody," Angew. Chem. Int. Ed., vol. 55, pp. 2361-2367, (2016).

\* cited by examiner

SDS-PAGE detection analysis of ADC-1

HIC-HPLC detection analysis of ADC-1

SEC-HPLC detection analysis of ADC-1

Detection of affinity of ADC-1 for cell surface ErbB2/HER2 ($EC_{50}$, nM)

Proliferation inhibition action of ADC-1 and other different drugs on tumor cells BT474 ($IC_{50}$, nM)

Proliferation inhibition action of ADC-1 and other different drugs on tumor cells NCI-N87 ($IC_{50}$, nM)

Proliferation inhibition action of ADC-1 and other different drugs on tumor cells HepG2 ($IC_{50}$, nM)

Inhibition effect of ADC-1 on NCI-N87 CDX mouse models

SDS-PAGE detection analysis of ADC-2

| DAR0 area | DAR2 area | DAR4 area | DAR |
|---|---|---|---|
| 1.26% | 8.51% | 90.23% | 3.78 |

HIC chromatogram of ADC-2

SEC chromatogram of ADC-2

Proliferation inhibition action of ADC-2 and other different drugs on tumor cells SK-BR-3 ($IC_{50}$, nM)

Proliferation inhibition action of ADC-2 and other different drugs on tumor cell HCC1954 ($IC_{50}$, nM)

Proliferation inhibition action of ADC-2 and other different drugs on tumor cells MDA-MB-468 ($IC_{50}$, nM)

SEC-HPLC detection analysis of ADC-3

High resolution mass spectrometry deconvolution diagram of ADC-3

Proliferation inhibition action of ADC-3 and other different drugs on tumor cells BxPC-3 ($IC_{50}$, nM)

Proliferation inhibition action of ADC-3 and other different drugs on tumor cells FaDu ($IC_{50}$, nM)

Proliferation inhibition action of ADC-3 and other different drugs on tumor cells HepG2 ($IC_{50}$, nM)

Tumor inhibition effect of ADC-3 on NCI-N87 CDX mice

Influence of ADC-3 on body weight of NCI-N87 CDX mice

| DAR0 area | DAR1 area | DAR2 area | DAR |
|---|---|---|---|
| 0.49% | 10.10% | 89.41% | 1.89 |

HIC-HPLC detection analysis diagram of ADC-4

SEC-HPLC detection analysis diagram of ADC-4

| DAR0 area | DAR1 area | DAR2 area | DAR |
|---|---|---|---|
| 1.24% | 10.91% | 87.95% | 1.87 |

HIC-HPLC detection analysis of ADC-5

SEC-HPLC detection analysis of ADC-5

In vitro inhibition activity of ADC-4 and ADC-5 on BxPC-3

HIC-HPLC detection analysis of ADC-6

SEC-HPLC detection analysis of ADC-6

In vitro inhibition activity of ADC-6 on SK-BR-3

In vitro inhibition activity of ADC-6 on NCI-N87

OLIGOSACCHARIDE LINKER, LINKER-PAYLOAD COMPRISING THE SAME AND GLYCAN CHAIN-REMODELED ANTIBODY-DRUG CONJUGATE, PREPARATION METHODS AND USES THEREOF

CROSS REFERENCE TO RELATED APPLICATIONS

This application claims priority to and is a continuation of International Application No. PCT/CN2023/098081, filed on Jun. 2, 2023, which claims priority to and the benefit of International Application No. PCT/CN2023/085098, filed on Mar. 30, 2023, Chinese Patent Application No. 202210625988.5, filed on Jun. 2, 2022, and Chinese Patent Application No. 202210629801.9, filed on Jun. 2, 2022, the disclosures of which are incorporated herein by reference in its entirety

REFERENCE TO A SEQUENCE LISTING

This application contains a Sequence Listing as a separate part of the disclosure. The contents of the Sequence Listing (GQH-16-PCTC-SequenceListing.xml; Size 8,313 bytes; and Date of Creation: Sep. 8, 2023) are incorporated herein by reference.

TECHNICAL FIELD

The present disclosure relates to an oligosaccharide (especially disaccharide) linker. The present disclosure further relates to a linker-payload compound including an oligosaccharide group, especially a disaccharide group, where the oligosaccharide group is attached to the remainder of the compound by an amide bond. The present disclosure further relates to an antibody-drug conjugate (ADC) including the linker-payload compound, where a glycan chain in an antibody is remodeled with the oligosaccharide group in the linker-payload compound. The present disclosure further relates to preparation methods and use of the above-mentioned substances.

BACKGROUND

Cancer is one of the leading causes of human death, with about one in six deaths worldwide each year related to cancer. There were 24.5 million new cancer cases and 9.6 million cancer deaths worldwide in 2017. Cancer is mainly treated through surgical treatment, radiation treatment and drug therapy. With the development and application of these therapies, the survival status of cancer patients has been greatly improved. The drug therapy for cancer has evolved through three generations: chemotherapy, targeted therapy and immunotherapy. The chemotherapy plays an important role in cancer treatment. However, it also has large non-therapeutic side effects. That is, it will kill a large number of normal cells while killing cancer cells. The targeted therapy reduces the serious toxicity and side effects of traditional chemotherapy to a certain extent. In this therapy, a small molecule targeted drug (mainly tyrosine kinase inhibitor at present) or a monoclonal antibody is mainly utilized to target a specific gene or protein (i.e., target) involved in the growth and survival of tumor cells to tumor cells and tissue. Antibody-drug conjugates (ADCs) are innovative targeted drugs in which a highly active small molecule drug is linked to a monoclonal antibody via chemical bond to form an innovative drug molecule. The ADCs leverage the high activity of the small molecule drugs and the high specificity and targeting ability of antibody drugs, which can reduce the non-therapeutic side effects of small molecule toxins on important tissue and organs such as liver, kidney, nerve and heart to a certain extent, furthermore overcome the limited efficacy of an antibody therapy on solid tumors. Therefore, ADC therapeutics have become one of the hotspots of current research and development of an anti-tumor drug.

The development of ADCs involves systematic engineering of four elements, the monoclonal antibody, the bioactive small molecule, the linker as well as the conjugation method. The conjugation method greatly influences drug related properties such as stability in drug efficacy, metabolic consistency and quality control (Tsuchikama K, An Z. Antibody-drug conjugates: recent advances in conjugation and linker chemistries. Protein Cell 2018, 9, 33-46). For ADCs currently on the market and in the clinical stage, random conjugation based on lysine or cysteine residues are mainly utilized, which often results in a highly heterogeneous mixtures with random conjugation sites and a non-uniform drug/antibody ratio (DAR). As a result, it is prone to problems in aspects of process stability, quality control, drug stability, metabolic consistency, safety, etc.

In order to overcome the above problems caused by random conjugation, a lot of research has been conducted for the development and application of site-specific conjugation strategies in academia and industry since 2008, and some promising progress has been made. These site-specific conjugation methods can be roughly divided into three types: a conjugation technology based on engineering mutagenesis to introduce specific amino acids, an enzymatic conjugation technology based on peptide tag insertion and a site-specific conjugation technology based on enzymatic glycan remodeling. The exploration and application of these site-specific conjugation technologies in the development of ADCs have effectively solved many problems arising from random conjugations. However, the first two types of site-specific conjugation technologies usually require extra antibody engineering or modification, thus lacking the versatility in preparing ADCs for antibodies with different targets. Each new antibody requires a lot of repetitive and tedious cell engineering. Therefore, the efficiency of new drug development is greatly reduced. The site-specific conjugation based on antibody Fc glycan remodeling does not require antibody modification and cell engineering, which greatly reduces the difficulty and workload in development. Therefore, it has the potential to become a versatile platform technology for antibody site-specific conjugation.

Highly conserved glycosylation is found in asparagine at position 297 in an Fc region of the antibody (N-297 Glycan). Site-specific attachment of different molecules on the antibody can be achieved by the glycan remodeling of this site (Wang L X, Tong X, Li C. Glycoengineering of Antibodies for Modulating Functions. Annu Rev Biochem 2019, 88, 433-459). There are two major types of site-specific conjugation technologies based on antibody Fc glycan modification:

1) Chemical method: using sodium periodate to oxidize core fucose (Zuberbuhler K, Casi G, Bernardes G J, et al. Fucose-specific conjugation of hydrazide derivatives to a vascular-targeting monoclonal antibody in IgG format. Chem Commun 2012, 48, 7100-7102) or o-diol in sialic acid at the end of glycosyl (Zhou Q, Stefano J E, Manning C, et al. Site-specific antibody-drug conjugation through glycoengineering. Bioconjugate Chem 2014, 25, 510-520) to obtain corresponding aldehydes, and aldehydic carbonyl group can be conjugated with small molecule toxin fragments to prepare ADCs. The limitation of such methods lies in glycan structure at N-297 site is diverse, and not all monoclonal antibody glycan contains reactive sites, resulting in great limitations to substrates; and 2) Enzymatic catalysis method: using deglycosylation-transglycosylation catalysis relay with tool enzymes such as endoglycosidase and glycosyltransferase to achieve glycan remodeling to introduce a biologically orthogonal reactive group, and then site-specific conjugation preparation of ADCs is achieved through subsequent chemical reactions (Wang L X, Tong X, Li C. Glycoengineering of antibodies for modulating functions. Annu Rev Biochem 2019, 88, 433-459; and Zeng Y, Tang F, Shi W, et al. Recent advances in synthetic glycoengineering for biological applications. Current Opinion in Biotechnol. 2022, 74, 247-255).

In 2012, Wang Laixi et al. reported an antibody glycan remodeling site-specific conjugation technology based on the catalysis of endoglycosidase Endo S and its mutant (Huang W, Giddens J, Fan S Q, et al. Chemoenzymatic glycoengineering of intact IgG antibodies for gain of functions. J. Am. Chem. Soc. 2012, 134, 12308). In this technology, a glycan-remodeled antibody with a defined glycan structure and azide modifications is synthesized through the selective deglycosylation at the β-1,4-glycosidic bond between GlcNAc-GlcNAc of Fc glycan at N-297 site by wild type Endo S, and followed by the transglycosylation mediated by a mutated enzyme Endo S D233Q. Base on this work, Wang Laixi and Huang Wei et al. have developed a large type of ADC site-specific conjugation technologies, in which deglycosylation-transglycosylation-click chemistry three-step process was involved, under the catalysis of tool enzymes such as endoglycosidase Endo S or Endo S2 and their mutants (Zeng Y, Tang F, Shi W, et al. Recent advances in synthetic glycoengineering for biological applications. Current Opinion in Biotechnol. 2022, 74, 247-255.). In 2021, Wang Laixi et al. reported Endo S2-catalyzed site-specific conjugation of antibody via glycan remodeling in a one-pot manner, where a bioorthogonal azide functional group is introduced to the antibody, and then ADC molecules are obtained after a click reaction step (Zhang X, Ou C, Liu H, et al. General and robust chemoenzymatic method for glycan-mediated site-specific labeling and conjugation of antibodies: facile synthesis of homogeneous antibody-drug conjugates. ACS Chem. Biol. 2021, 16, 11, 2502-2514). At present, the above technologies are all in the basic research stage, and there have been no report on the clinical development of ADCs based on corresponding technologies.

Another type of commonly used tool enzymes in the glycan remodeling site-specific conjugation technology is β-1,4-galactosyltransferase (β-1,4-Gal-T1) and its mutants (β-1,4-Gal-T1 Y289L). Uridine diphosphate galactose (Gal-UDP) is taken as a donor in this enzyme to transfer galactose (Gal) to the non-reducing end of acetylglucosamine (GlcNAc) of glycoprotein. In 2009, Qasba et al. (Boeggeman E, Ramakrishnan B, Pasek M, et al. Site specific conjugation of fluoroprobes to the remodeled Fc N-glycans of monoclonal antibodies using mutant glycosyltransferases: application for cell surface antigen detection. Bioconjugate Chem. 2009, 20, 6, 1228-1236) first reported a site-specific conjugation technology in which β-1,4-Gal-T1 and β-1,4-Gal-T1 Y289L were used as tool enzymes, and C2-keto-Gal-UDP or N-azidoacetylgalactosamine-UDP (GalNAz-UDP) as a donor, providing ketone or azide modified antibodies. On this basis, they reported a first example of β-1,4-Gal-T1 and its mutant mediated ADC synthesis in 2014, in which three sequential steps including deglycosylation, transglycosylation and bioorthogonal reaction were involved. It is worth noting that a corresponding ADC molecule still retains a considerable degree of affinity for FcγRIIIa and FcγRI receptors, and the antibody-dependent cytotoxicity (ADCC) effect of the molecule is somewhat retained. This molecule demonstrates potential killing efficacy in Her2-positive JIMT-1 breast cancer cell lines (Zhu Z, Ramakrishnan B, Li J, et al. Site-specific antibody-drug conjugation through an engineered glycotransferase and a chemically reactive sugar. mAbs 2014, 6, 1190-1200). On the basis of the above work, a three-step ADC synthesis method involving deglycosylation-transglycosylation-bioorthogonal reaction process was developed by Synaffix via combined use of tool enzymes endoglycosidases Endo S and β-1,4-Gal-T1 Y289L (Van Geel R, Wijdeven M A, Heesbeen R, et al. Chemoenzymatic conjugation of toxic payloads to the globally conserved N-glycan of native mAbs provides homogeneous and highly efficacious antibody-drug conjugates. Bioconjugate Chem. 2015, 26, 2233-2242). Furthermore, a four-step synthesis method for ADCs through deglycosylation-transglycosylation-transglycosylation-bioorthogonal reaction process was reported in the references (Li X, Fang T, Boons G J. Preparation of well-defined antibody-drug conjugates through glycan remodeling and strain-promoted azide-alkyne cycloadditions. Angew. Chem. Int. Ed. 2014, 53, 7179-7182), and a total of three tool enzymes, β-1,4-Gal-T1, β-1,4-Gal-T1 Y289L and sialyltransferase, were used in this method.

The aforementioned glycan remodeling reaction avoids the problem of antibody engineering in other site-specific conjugation technologies, but still with very big limitations. In one aspect, the glycan remodeling reaction has lengthy conjugation steps and cumbersome operation, and at least two steps of enzymatic reaction plus one step of chemical reaction are required, that is to say, at least three steps of reaction and three times of complete purification are required to afford the resulted ADCs. In another aspect, even a trace amount of tool enzyme residue in the product could lead to the decomposition of ADC products via deglycosylation, which may cause the shedding of toxin molecules, resulting in servere toxic reactions, this would pose a major challenge to drug development and production, and also brings a major hidden danger to the safety of ADCs. More importantly, in the aforementioned glycan remodeling reaction, the chemical methodology for the linking of oligosaccharide and toxin molecules is still quite limited, and additional reactions may be required to make the manner desirable. However, these additional reactions in turn may lead to many adverse byproducts. The present disclosure aims to solve these problems.

SUMMARY

The present disclosure provides a novel oligosaccharide (especially disaccharide) linker and a preparation method and application thereof. A linker-payload compound including an oligosaccharide group is further provided, where the oligosaccharide group is attached to the remainder of the compound via an amide bond. Specifically, the present disclosure provides a linker-payload compound with formula (I):

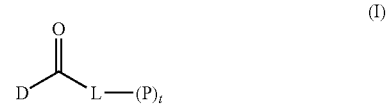

where
P is a payload;
D-C(O)-L- is a linker;
D-C(O)— is an oligosaccharide structure, which is a -first hexosyl or its derivative moiety-(second hexosyl or its derivative moiety)$_f$-β-D-N-acetylglucosamine moiety or a -first hexosyl or its derivative moiety- (second hexosyl or its derivative moiety)$_f$-β-D-glucose oxazoline moiety, where C-6 of the first hexosyl or its derivative moiety is in the form of —C(O)—, which is —C(O)— in D-C(O)—, the β-D-N-acetylglucosamine moiety is

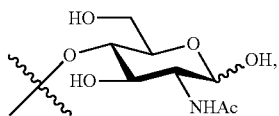

the β-D-glucose oxazoline moiety is

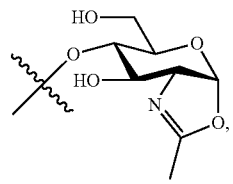

and f is 0, 1, 2, 3, 4, 5 or 6;

L is a linker end, for example, it can be cleaved from P chemically (e.g., via hydrolysis) or biologically (e.g., via enzymatic catalysis) to release P, and L is directly connected to carbonyl in D-C(O)— via —NH— therein, where when L is a unbranched linker end, L is attached to one P, and t is 1, while when L is a branch linker end, each branch can be attached to one P, and t is an integer greater than 1 (e.g., 2, 3, 4, 5, 6, 7, 8, 9, or 10).

The present disclosure further relates to an antibody-drug conjugate (ADC) including the linker-payload compound, where a glycan chain in an antibody is remodeled with the oligosaccharide group in the linker-payload compound. Specifically, the present disclosure provides an antibody-drug conjugate having a site-specific attachment based on an N-glycosylation site in the Fc region of an antibody, having formula (II):

where the C-6 of the first hexosyl or its derivative moiety is in the form of —C(O)—;

L is a linker end (for example, it can be cleaved from P chemically (e.g., via hydrolysis) or biologically (e.g., via enzymatic catalysis) to release P), and L is directly connected to carbonyl in the first hexosyl or its derivative moiety via —NH— therein, where when L is a unbranched linker end, L is attached to one P, and t is 1, while when L is a branch linker end, each branch can be attached to one P, and t is an integer greater than 1 (e.g., 2, 3, 4, 5, 6, 7, 8, 9, or 10).

f is 0, 1, 2, 3, 4, 5 or 6.

The present disclosure further relates to preparation methods and use of the above-substances.

Since a novel oligosaccharide structure that forms the amide bond is employed in the present disclosure, the scope of ADCs obtained by the glycan remodeling technology is extended. Where expected, compounds with a NH$_2$ group (e.g., a compound with a structure of L'-(P)$_t$, where P and t are as defined herein, and L' is the same as L as defined herein, except that —NH— attached to D-C(O)— in L is H$_2$N— in L') can each form a linker-payload

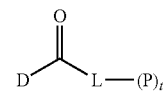

containing the oligosaccharide linker by simple amide formation reactions via the above-mentioned oligosaccharide structure, and then furnish ADCs with the antibody, and

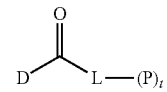

the conjugation with the antibody can be carried out via one-pot enzyme catalysis process. In addition, ADCs, provided by the present disclosure, with a novel oligosaccharide structure that enables the formation of the amide bond, can be efficiently delivered to target cells and efficiently release the payload in the target cells. In the present disclosure, a unique oligosaccharide carboxylic acid substrate

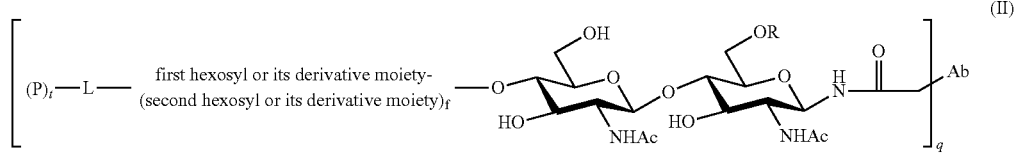

where
P is a payload;
R is hydrogen or α-L-fucosyl group;
q is 1 or 2;
Ab is an antibody or antigen-binding fragment (e.g., —NHC(O)CH$_2$— in formula (II) is from asparagine at position 297 in the Fc region of the antibody), (e.g., 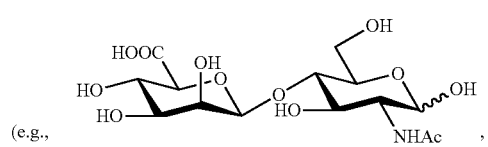

-continued

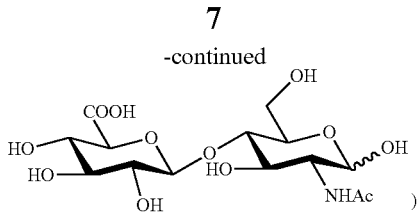

can be effectively connected to an amine compound through a mild, compatible amide formation in a single step, thereby simplifying and accelerating the synthesis of the linker-payload compound, without the need for additional reactions that may lead to many adverse by-products.

DETAILED DESCRIPTION

General Definition

Figure 1:
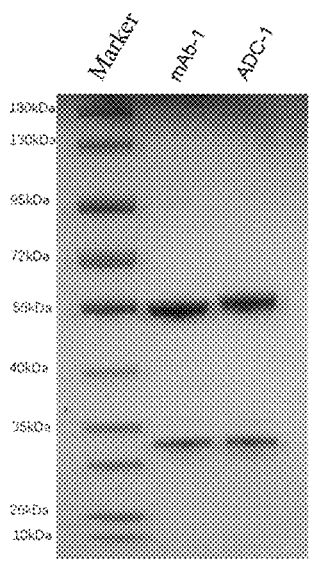
FIG. 1. SDS-PAGE detection analysis of ADC-1

Unless otherwise defined, all technical and scientific terms used herein have the same meanings as those commonly understood by those skilled in the art. The technologies used herein refer to technologies generally understood in the art, including variants and equivalent substitutions that are obvious to those skilled in the art. Although it is believed that the following terms are easy to understand by those skilled in the art, the following definitions are elaborated to better illustrate the present disclosure. When a trade name appears herein, it refers to a corresponding product or its active constituent. All patents, published patent applications, and publications referenced herein are incorporated herein by reference.

When a certain amount, concentration or another value or parameter is described in the form of a range, preferred range or preferred upper limit or preferred lower limit, it should be understood as equivalent to specifying any range formed by combining any upper limit or preferred value with any lower limit or preferred value, regardless of whether the range is explicitly stated or not. Unless otherwise specified, the numeric ranges listed herein are intended to include the endpoints of the range and all integers and fractions (decimals) within the range. For example, the expression "i is an integer from 1 to 20" indicates that i is any integer from 1 to 20. For example, i may be 1, 2, 3, 4, 5, 6, 7, 8, 9, 10, 11, 12, 13, 14, 15, 16, 17, 18, 19 or 20. Other similar expressions, e.g., j, g, k, and the like should also be understood in a similar way.

Unless the context otherwise specifies, singular forms such as "a/an" and "the" include plural forms. The expression "one or more" or "at least one" may represent 1, 2, 3, 4, 5, 6, 7, 8, 9 or more.

The terms "about" and "approximately", when used with a numerical variable, usually mean that the value of the variable and all values of the variable are within the experimental error range (e.g., within the 95% confidence interval of the mean) or within a range of ±10% or wider of a specified value.

The term "optional" refers to the events subsequently described that may or may not necessarily occur, and the description includes cases where the events or situations described therein occur or do not occur.

The expressions "comprising", "including", "containing" and "having" are open-ended and do not exclude additional unlisted elements, steps or constituents. The expression "consisting of" does not include any unspecified elements, steps or constituents. The expression "substantially consisting of" means that the scope is limited to the specified elements, steps or constituents and optionally existing elements, steps or constituents that do not materially influence the essential and novel features of the subject claimed for protection. It should be understood that the expression "comprising" includes the expression "substantially consisting of" and "consisting of".

The term "targeting molecule" refers to a molecule that has affinity for specific targets (e.g., a receptor, a cell surface protein, a cytokine, a tumor specific antigen, etc.). The targeting molecule can deliver the payload to a specific site in vivo by targeted delivery. The targeting molecule can recognize one or more targets. A specific target is defined by the target it recognizes. For example, the targeting molecule targeting the receptor can deliver cytotoxin to a site containing a large number of receptors. Examples of the targeting molecules include, but are not limited to, an antibody, a binding protein of a given antigen, an antibody mimic, a scaffold protein with affinity for a given target, a ligand, etc. Targets recognized by the targeting molecule include, but are not limited to, CD19, CD22, CD25, CD30/TNERSF8, CD33, CD37, CD44v6, CD56, CD70, CD71, CD74, CD79b, CD117/KIT, CD123, CD138, CD142, CD174, CD227/MUC1, CD352, CLDN18.2, DLL3, ErbB2/HER2, CN33, GPNMB, ENPP3, Nectin-4, EGFRvIII, SLC44A4/AGS-5, CEACAM5, PSMA, TIM1, LY6E, LIV1, Nectin4, SLITRK6, HGFR/cMet, SLAMF7/CS1, EGFR, BCMA, AXL, NaPi2B, GCC, STEAP1, MUC16, Mesothelin, ETBR, EphA2, 5T4, FOLR1, LAMP1, Cadherin 6, FGFR2, FGFR3, CA6, CanAg, Integrin $\alpha$V, TDGF1, ephrin A4, TROP2, PTK7, NOTCH3, C4.4A, FLT3, B7H3/4, a tissue factor (TF) and ROR1/2.

HER2 refers to human epidermal growth factor receptor-2, which belongs to the epidermal growth factor (EGFR) receptor tyrosine kinase family. In this application, the terms ErbB2 and HER2 have the same meaning and can be used interchangeably.

TROP2 is a transmembrane glycoprotein encoded by a Tacstd2 gene. TROP2 is an intracellular calcium signal sensor and is overexpressed in a variety of tumors.

CLDN18.2 (Claudin-18 isoform 2) is a member of the human Claudin family. CLDN18.2 is a pan-cancer target expressed in primary and metastatic lesions of several human cancer types.

As used herein, the term "antibody" is used in a broad way, and its definition encompasses conventional antibodies, recombinant antibodies/genetically engineered antibodies, especially intact monoclonal antibodies, polyclonal antibodies, monospecific antibodies, multispecific antibodies (e.g., bispecific antibodies) and antibody fragments, as long as they have the required biological activity. The antibody may be any subtype (e.g., IgG, IgE, IgM, IgD, and IgA) or subclass, and can originate from any suitable species. In some embodiments, the antibody is human or mouse-derived. The antibody may also be a fully human antibody, a humanized antibody, or a chimeric antibody prepared by recombinant methods.

The monoclonal antibody used herein refers to an antibody obtained from a substantially homogeneous antibody population. That is, except for a few possible natural mutations, individual antibodies that make up the population are the same. The monoclonal antibody has high specificity for a single antigen site. The term "monoclonal" refers to that the features of the antibody originate from the substantially homogeneous antibody population and should not be interpreted as requiring specific methods to produce the antibody.

An intact antibody or full-length antibody substantially includes an antigen binding variable region and a light chain constant region (CL) and a heavy chain constant region (CH), which may include CH1, CH2, CH3 and CH4, depending on the subtype of the antibody. The antigen binding variable region (also referred to as a fragment variable region, Fv fragment) generally includes a light chain variable region (VL) and a heavy chain variable region (VH). The constant region may be a constant region having a natural sequence (e.g., a constant region having a human natural sequence) or a variant of its amino acid sequence. The variable region recognizes and interacts with a target antigen. The constant region can be recognized by and interacts with an immune system.

The antibody fragment may include a portion of the intact antibody, preferably its antigen binding region or variable region. Examples of the antibody fragments include Fab, Fab', F(ab')2, an Fd fragment consisting of VH and CH1 domains, an Fv fragment, a single domain antibody (dAb) fragment, and an isolated complementary determining region (CDR). The Fab fragment is an antibody fragment obtained by digesting full-length immunoglobulins with papain, or a fragment having the same structure produced by, for example, recombinant expression. The Fab fragment includes a light chain (including VL and CL) and another chain, where the other chain includes a variable region (VH) of the heavy chain and a constant region (CH1) of the heavy chain. The F(ab')2 fragment is an antibody fragment obtained by digesting immunoglobulins with papain at pH 4.0 to 4.5, or a fragment having the same structure produced by, for example, recombinant expression. The F(ab')2 fragment substantially includes two Fab fragments, where each heavy chain moiety includes several additional amino acids, including cysteine that forms a disulfide bond linking the two fragments. The Fab' fragment is a fragment that includes half of the F(ab')2 fragment (one heavy chain and one light chain). The antibody fragment may include multiple chains attached together, for example by a disulfide bond and/or peptide linker. Examples of the antibody fragments further include single-chain Fv (scFv), Fv, dsFv, a bispecific antibody, Fd and Fd' fragments, as well as other fragments, including a modified fragment. The antibody fragment generally includes at least or about 50 amino acids, generally at least or about 200 amino acids. The antigen-binding fragment may include any one where an antibody immunospecifically binding to antigen is available when it is inserted into a framework of the antibody (for example, by replacing a corresponding region).

Specifically, the antibody-drug conjugate of this application is site-specific conjugated based on any natural N-glycosylation modified site containing the FC region of the antibody. For a molecule comprising glycan chain in the FC region of the antibody (including but not limited to antibodies/bispecific antibodies/FC fusion proteins/single chain antibodies/nanoantibodies, etc.), one-step preparation is carried out with an oligosaccharide-containing linker-payload in this application. Therefore, the antibody in this application has no special restrictions, except that its FC region contains a glycan chain, which may be a natural antibody.

In addition, the antibody of the present disclosure may also be prepared by using the technologies well known in the art, such as the following technologies or a combination thereof: a recombination technology/genetic engineering technology, a phage display technology, a synthesis technology or other technologies known in the art. For example, a genetically engineered recombinant antibody can be expressed by a suitable culture system (e.g., *Escherichia coli* (*E. Coli*) or mammalian cells). The genetic engineering may refer to, for example, introducing a ligase specific recognition sequence at its end.

As used herein, the term "targeting molecule-drug conjugate" is referred to as "conjugate". Examples of the conjugates include, but are not limited to, the antibody-drug conjugate.

A small molecule compound refers to a molecule of the same size as an organic molecule generally used in pharmaceutical drugs. The term does not encompass biological macromolecules (e.g. proteins, nucleic acids, etc.), but encompasses low molecular weight peptides or their derivatives, such as dipeptides, tripeptides, tetrapeptides, pentapeptides, etc. Generally, the molecular weight of the small molecule compound may be, for example, about 100 Da to about 2000 Da, about 200 Da to about 1000 Da, about 200 Da to about 900 Da, about 200 Da to about 800 Da, about 200 Da to about 700 Da, about 200 Da to about 600 Da, and about 200 Da to about 500 Da.

The cytotoxin refers to a substance that inhibits or prevents cell expression activity and cell function, and/or causes cell damage. The cytotoxin generally used in ADCs is more toxic than that of chemotherapy drugs. Examples of the cytotoxin include, but are not limited to, drugs targeting the following targets: microtubule cytoskeletons, DNA, RNA, kinesin-mediated protein transport, and regulation of apoptosis. Drugs targeting the microtubule cytoskeletons may be, for example, a microtubule stabilizer or tubulin polymerization inhibitor. Examples of the microtubule stabilizers include, but are not limited to, taxanes. Examples of the tubulin polymerization inhibitors include, but are not limited to, maytansinoids, auristatins, vinblastins, colchicines and aplysiatoxins. Drugs targeting DNA may be, for example, drugs that directly destroy a DNA structure or topoisomerase inhibitors. Examples of drugs that directly destroy the DNA structure include, but are not limited to, a DNA double strand breaker, a DNA alkylator, and a DNA intercalator. The DNA double strand breaker may be, for example, enediyne antibiotics, including, but not limited to, dynemicin, esperamicin, neoearcinostatin, uncialamycin, etc. The DNA alkylator may be, for example, a DNA bis-alkylator, i.e., a DNA cross linker or DNA mono-alkylator. Examples of the DNA alkylators include, but are not limited to, pyrrolo [2,1-c] [1,4]benzodiazepine (PBD) dimers, 1-(chloromethyl)-2,3-dihydro-1H-benzo[e]indole (CBI) dimers, CBI-PBD isodimers, indolinebenzodiazepine (IGN) dimers, a duocarmycin-like compounds, etc. Examples of the topoisomerase inhibitors include, but are not limited to, exatecan and its derivatives (e.g., DX8951f, DXd-(1) and DXd-(2), structures of which are described below), camptothecins and anthracyclines. Drugs targeting RNA may be, for example, drugs that inhibit splicing, and examples of the drugs include, but are not limited to, pladienolide. Drugs targeting kinesin-mediated protein transport may be, for example, a mitosis kinesin inhibitor, including, but not limited to, a kinesin spindle protein (KSP) inhibitor.

"Spacer" refers to a structure that is located between different structural modules and can space the structural modules spatially. The definition of the spacer does not limit whether it has a certain function, and whether it can be cut off or degraded in vivo. Examples of the spacers include, but are not limited to, amino acid and non-amino acid structures, where the non amino acid structures may be, but are not limited to, amino acid derivatives or analogs. "Spacer sequence" refers to an amino acid sequence that serves as the spacer, and examples of the spacer sequence include, but are not limited to, a single amino acid, a sequence containing multiple amino acids, for example a sequence containing two amino acids, such as GA, or for example GGGGS, GGGGSGGGGS, GGGGSGGGGSGGGGS, etc. A self-immolative spacer (e.g., a self-immolative spacer Sp1) is a covalent component. The covalent component causes a protective moiety of a precursor to be activated followed by successive cleavage of two chemical bonds: the protective moiety (e.g., a cleavable sequence) is removed after activated, which initiates a cascade of decomposition reactions, resulting in the sequential release of smaller molecules. Examples of the self-immolative spacers include, but are not limited to, p-aminobenzyloxycarbonyl (PABC), acetal, heteroacetal, and a combination thereof.

As used herein, the term "amino acid" includes both "natural amino acids" and "unnatural amino acids".

The term "natural amino acid" refers to amino acids, which are protein constituent amino acids, including twenty common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine), and less common selenocysteine and pyrrolysine.

As used herein, the term "unnatural amino acid" refers to amino acids, which are not protein constituent amino acids. Specifically, this term refers to amino acids that are not natural amino acids as defined above.

The term "alkyl" refers to a straight or branched-chain saturated aliphatic hydrocarbon group consisting of carbon and hydrogen atoms. The saturated aliphatic hydrocarbon group is attached to the remainder of the molecule by a single bond. The alkyl may have 1 to 20 carbon atoms, referring to "$C_1$-$C_{20}$ alkyl", for example, $C_1$-$C_4$ alkyl, $C_1$-$C_3$ alkyl, $C_1$-$C_2$ alkyl, $C_3$ alkyl, $C_4$ alkyl, and $C_3$-$C_6$ alkyl. Non-limiting examples of the alkyl include, but are not limited to, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or isomers thereof. Divalent free radical refers to a group obtained by removing a hydrogen atom from a carbon atom having free valence electrons of a corresponding monovalent free radical. The divalent free radical has two attachment sites attached to the remainder of the molecule. For example, "alkylene" or "alkylidene" refers to a saturated straight or branched-chain divalent bivalent hydrocanbon radical. Examples of "alkylene" include, but are not limited to, methylene (—$CH_2$—), ethylidene (—$C_2H_4$—), propylidene (—$C_3H_6$—), butylene (—$C_4H_8$—), pentylene (—$C_5H_{10}$—), hexylene (—$C_6H_{12}$—), 1-methylethylidene (—CH(CH$_3$)CH$_2$—), 2-methylethylidene (—CH$_2$CH(CH$_3$)—), methylpropylidene or ethylpropylidene.

The term "cycloalkyl" refers to a cyclic saturated aliphatic group consisting of carbon and hydrogen atoms. The cyclic saturated aliphatic group is attached to the remainder of the molecule by a single bond. The cycloalkyl may have 3 to 10 carbon atoms, namely "$C_3$-$C_{10}$ cycloalkyl", for example cyclopropyl, cyclobutyl, cyclopentyl, cyclohexyl, cycloheptyl, cyclooctyl, cyclononyl, or cyclodecyl. "Cycloalkylene" refers to divalent cycloalkyl.

The term "heterocyclyl" refers to that one or more carbon atoms in the above-mentioned cycloalkyl are replaced by heteroatoms selected from nitrogen, oxygen and sulfur, for example, aze, oxa, or thiocyclic propyl, aze, oxa, or thiocyclic butyl, pyrrolidinyl, pyrazolidinyl, imidazolidinyl, tetrahydrofuryl, tetrahydrothienyl, piperidinyl, piperazinyl, tetrahydropyranyl, or tetrahydrothiapyranyl. "Heterocyclylene" refers to divalent cycloalkyl.

When referring to "substitution" herein, unless otherwise referring to, relevant substituents are selected from alkyl, halogen, amino, monoalkyl amino, dialkyl amino, nitro, cyano, formyl, alkyl carbonyl, carboxy, alkyl oxycarbonyl, alkyl carbonyloxy, aminocarbonyl, monoalkylaminocarbonyl, dialkylaminocarbonyl, formylamino, alkyl carbonylamino, formyl (monoalkyl) amino or alkyl carbonyl (monoalkyl) amino.

As used herein, when a group is combined with another group, the attachment between the groups may be linear or branched, provided that a chemically stable structure is formed. The structure formed by such combination may be attached to other moieties of the molecule by any suitable atom in the structure, preferably by a specified chemical bond. For example, when two or more divalent groups selected from —CR$^1$R$^2$—, $C_{1-10}$ alkylene, $C_{4-10}$ cycloalkylene, $C_{4-10}$ heterocyclylene, and —(CO)— are bonded together to form a combination, two or more divalent groups can be linearly attached with each other, for example, —CR$^1$R$^2$—$C_{1-10}$ alkylene-(CO)—, —CR$^1$R$^2$—$C_{4-10}$ cycloalkylene-(CO)—, —CR$^1$R$^2$—$C_{4-10}$cycloalkylene-$C_{1-10}$ alkylene-(CO)—, —CR$^1$R$^2$—CR$^{1'}$R$^{2'}$—(CO)—, —CR$^1$R$^2$—CR$^{1'}$R$^{2'}$—CR$^{1''}$R$^{2''}$—(CO)—, etc. The resulting bivalent structure may be further attached to other moieties of the molecule.

When multiple identical letters representing chemical groups appear in the same chemical structural formula, they are chosen independently and are not necessarily the same. For example, multiple M in formula I-2 are each independently selected from LKa-L$^2$-L$^1$-B—P; while multiple L$^2$ and the like are also independent of each other and not necessarily the same.

As used herein, the expression "antibody-drug conjugate" and "antibody-conjuated drug" have the same meaning.

Linker-Payload Compound

In a first aspect, the present disclosure provides a linker-payload compound having formula (I):

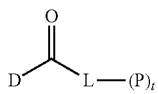

where

P is a payload;

D-C(O)-L- is a linker;

D-C(O)— is an oligosaccharide structure, which is a -first hexosyl or its derivative moiety- (second hexosyl or its derivative moiety)$_f$-β-D-N-acetylglucosamine moiety or a -first hexosyl or its derivative moiety- (second hexosyl or its derivative moiety)$_f$-β-D-glucose oxazoline moiety, where C-6 of the first hexosyl or its derivative moiety is in the form of —C(O)—, which is —C(O)— in D-C(O)—, the β-D-N-acetylglucosamine moiety is

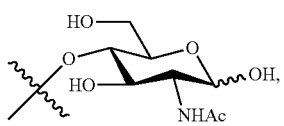

the β-D-glucose oxazoline moiety is

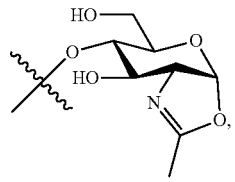

and f is 0, 1, 2, 3, 4, 5 or 6;

L is a linker end (for example, it can be cleavedcleaved from P chemically (e.g., via hydrolysis) or biologically (e.g., via enzymatic catalysis) to release P), and L is directly connected to carbonyl in D-C(O)— via —NH— therein, where when L is a unbranched linker end, L is attached to one P, and t is 1, while when L is a branch linker end, each branch can be attached to one P, and t is an integer greater than 1 (e.g., 2, 3, 4, 5, 6, 7, 8, 9, or 10).

In an embodiment, -L-(P)$_t$ is -L$^2$-L$^1$-B—P, i.e., formula (I) is:

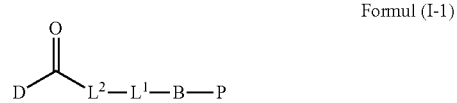

Formul (I-1)

where

B is independently absent, or is 1) below, or 2) below, or a combination of 1) and 2) below: 1) the self-immolative spacer Sp1; 2) a divalent group, or a combination of two or more divalent groups, where the divalent group is selected from: —CR$^1$R$^2$—, $C_{1-10}$ alkylene, $C_{4-10}$ cycloalkylene, $C_{4-10}$ heterocyclylene and —(CO)—;

L$^1$ is independently absent, or is a uncleavable sequence, for example conjugating a payload to an antibody by a thioether bond; or a cleavable sequence including an amino acid sequence that is enzymatically cleavable, where the amino acid sequence that is enzymatically cleavable includes 1, 2, 3, 4, 5, 6, 7, 8, 9 or 10 amino acids;

L$^2$ is independently absent; or is 1) below; or 2) below; or a combination of 1) and 2) below:

1) —NH—$C_{2-20}$ alkylene, where one or more —CH$_2$— structures in the alkylene are optionally replaced by the following groups: —CR$^3$R$^4$—, —O—, —(CO)—, —S—, —S(=O)$_2$—, —NR$^5$—, —N*R$^6$R$^7$—, $C_{4-10}$ cycloalkylene, $C_{4-10}$ heterocyclylene and phenylene, where the cycloalkylene, the heterocyclylene and the phenylene are each independently unsubstituted or is substituted with at least one substituent selected from halogen, —$C_{1-10}$ alkyl, —$C_{1-10}$ haloalkyl, —$C_{1-10}$ alkylene-NH—R$^8$ and —$C_{1-10}$ alkylene-O—R$^9$;

2) an amino acid residue sequence, i.e., -*(AA)$_n$**-, where n is an integer from 1 to 100, AA, when occurring each time, is independently an amino acid residue, * represents the N-terminus of a corresponding amino acid and ** represents the C-terminus of the corresponding amino acid, and —(C$_2$H$_4$—O)$_m$—(CH$_2$)$_p$— is optionally present between amino and α-carbon of an amino acid, where m is 1, 2, 3, 4, 5, 6, 7, 8, 9 or 10; p is 0, 1, 2 or 3, and the * terminus forms an amide bond with the carbonyl in the oligosaccharide structure;

$R^1$, $R^2$, $R^3$, $R^4$, $R^5$, $R^6$, $R^7$, $R^8$ and $R^9$ are each independently selected from hydrogen, halogen, substituted or unsubstituted-$C_{1-10}$ alkyl, and $C_{4-10}$ cycloalkylene; or $R^1$ and $R^2$ and carbon atoms attached thereto together form a 3 to 6-membered cycloalkylene, and/or $R^3$ and $R^4$ and carbon atoms attached thereto together form a 3 to 6-membered cycloalkylene;

P is a payload attached to moiety B, or moiety $L^1$, or moiety $L^2$.

In another embodiment, -L-(P)$_t$ is

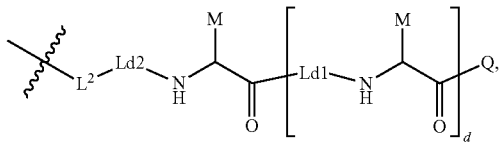

i.e., formula (I) is:

Formula (I-2)

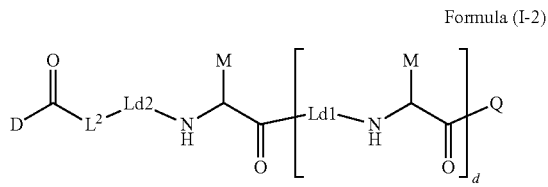

where

Ld2 and each Ld1 are bonds independently, or are selected from —NH—$C_{1-20}$ alkylene-(CO)— and —NH-(PEG)$_i$-(CO)—, or are natural amino acids independently unsubstituted or substituted with —CO-(PEG)$_j$-$R^{11}$ on the side chain or oligomeric natural amino acids with a polymerization degree of 2 to 10 (i.e., 2, 3, 4, 5, 6, 7, 8, 9 or 10);

-(PEG)$_i$- and -(PEG)$_j$- are each a PEG fragment, including a specified number of continuous —(O—$C_2H_4$)— structural units or continuous —($C_2H_4$—O)— structural units, optionally with $C_{1-10}$ alkylene attached at one end;

M is hydrogen or LKa-$L^2$-$L^1$-B-P;

Q is $NH_2$ or $L^2$-$L^1$B-P;

provided that the following cases are excluded: M is hydrogen and Q is $NH_2$;

each LKa is independently selected from

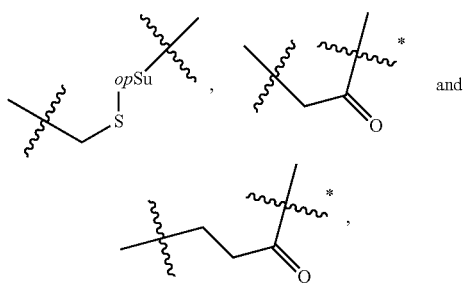

opSu is

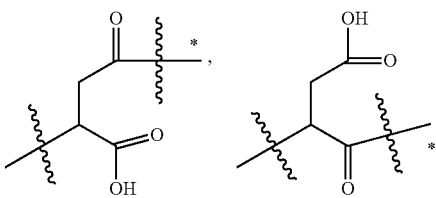 [SMILES: *C(=O)CC(*)C(=O)O ; *C(=O)C(*)CC(=O)O]

or a mixture thereof; where, * represents a moiety attached to $L^2$;

each $L^2$ is independently absent; or is 1) below; or 2) below; or a combination of 1) and 2) below:
1) —NH—$C_{2-20}$ alkylene, where one or more —$CH_2$— structures in the alkylene are optionally replaced by the following groups: —$CR^3R^4$—, —O—, —(CO)—, —S—, —S(=O)$_2$—, —$NR^5$—, —N*$R^6R^7$—, $C_{4-10}$ cycloalkylene, $C_{4-10}$ heterocyclylene and phenylene, where the cycloalkylene, the heterocyclylene and the phenylene are each independently unsubstituted or is substituted with at least one substituent selected from halogen, —$C_{1-10}$ alkyl, —$C_{1-10}$ haloalkyl, —$C_{1-10}$ alkylene-NH—$R^8$ and —$C_{1-10}$ alkylene-O—$R^9$; preferably, this group is —NH—$(C_2H_4)_2$—$(C_2H_4)$CO—;
2) an amino acid residue sequence, i.e., -*(AA)$_n$**-, where n is an integer from 1 to 100, AA, when occurring each time, is independently an amino acid residue, * represents the N-terminus of a corresponding amino acid and ** represents the C-terminus of the corresponding amino acid, and —($C_2H_4$—O)$_m$—(CH$_2$)$_p$— is optionally present between amino and α-carbon of an amino acid, where m is 1, 2, 3, 4, 5, 6, 7, 8, 9 or 10; p is 0, 1, 2 or 3, and the * terminus forms an amide bond with the carbonyl in the oligosaccharide structure; preferably, this sequence is -Gly-Gly-Gly-;

$L^1$ is independently absent, or is a uncleavable sequence, for example conjugating a payload to an antibody by a thioether bond; or a cleavable sequence including an amino acid sequence that is enzymatically cleavable, where the amino acid sequence that is enzymatically cleavable includes 1, 2, 3, 4, 5, 6, 7, 8, 9 or 10 amino acids;

Each B is independently absent, or is 1) below, or 2) below, or a combination of 1) and 2) below: 1) the self-immolative spacer Sp1; 2) a divalent group, or a combination of two or more divalent groups, where the divalent group is selected from: —$CR^1R^2$—, $C_{1-10}$ alkylene, $C_{4-10}$ cycloalkylene, $C_{4-10}$ heterocyclylene and —(CO)—;

P is a payload attached to moiety B, or moiety $L^1$, or moiety $L^2$;

$R^1$, $R^2$, $R^3$, $R^4$, $R^5$, $R^6$, $R^7$, $R^8$ and $R^9$ are each independently selected from hydrogen, halogen, substituted or unsubstituted —$C_{1-10}$ alkyl, and $C_{4-10}$ cycloalkylene; or $R^1$ and $R^2$ and carbon atoms attached thereto together form a 3 to 6-membered cycloalkylene, and/or $R^3$ and $R^4$ and carbon atoms attached thereto together form a 3 to 6-membered cycloalkylene;

$R^{11}$ is $C_{1-10}$ alkyl;

d is 0, 1, 2, 3, 4, 5 or 6;

each i is independently an integer from 1 to 100 (e.g., 1, 2, 3, 4, 5, 6, 7, 8, 9 or 10), preferably 1 to 20. Preferably, each i is independently an integer from 1 to 12, preferably 2 to 8, especially 4; and each j is independently an integer from 1 to 100 (e.g., 1, 2, 3, 4, 5, 6, 7, 8, 9 or 10), preferably 1 to 20. Preferably, each j is independently an integer from 1 to 12, preferably 8 to 12, especially 8, 9, 12 or 13.

In an embodiment, at least one of B, $L^1$ and $L^2$ is not "absent".

In an embodiment, $L^2$ is selected from: —NH—(CH$_2$)$_1$—(CH$_2$)$_2$(CO)—, where a is an integer of 0, 1, 2, 3, 4 or 5;

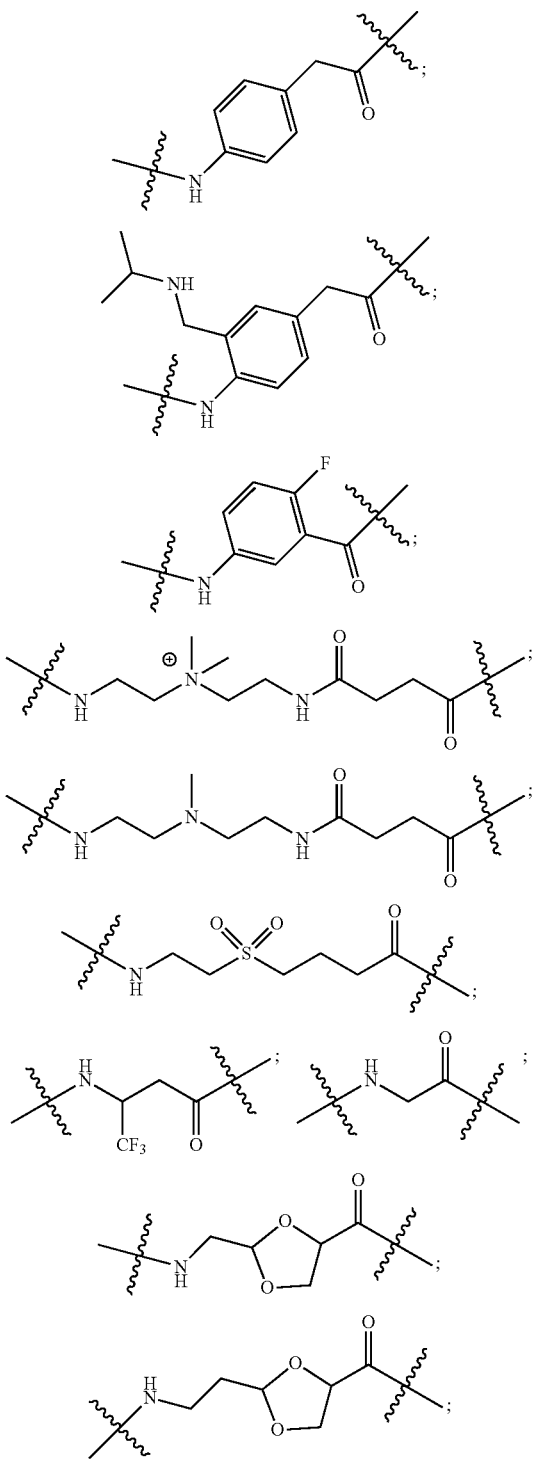

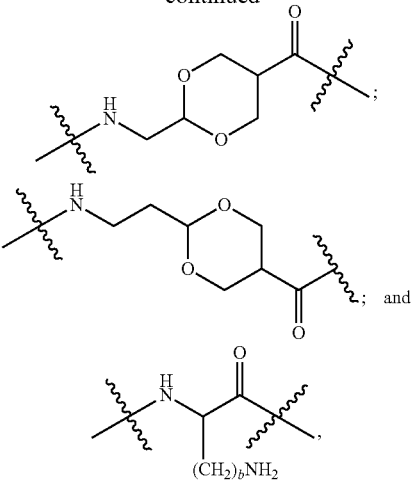

b is 1, 2, 3, 4, 5, 6, 7, 8, 9 or 10. In an embodiment, the carbonyl in the above-mentioned $L^2$ structure is attached to $L^1$. In an embodiment, a is 0, 1, 2 or 3, preferably 3.

In an embodiment, $L^2$ is an amino acid residue sequence, i.e., -*(AA)$_n$**-, where n is an integer from 1 to 100, AA, when occurring each time, is independently an amino acid residue, * represents the N-terminus of a corresponding amino acid and ** represents the C-terminus of the corresponding amino acid, and —(C$_2$H$_4$—O)$_m$—(CH$_2$)$_p$— is optionally present between amino and α-carbon of an amino acid, where m is 1, 2, 3, 4, 5, 6, 7, 8, 9 or 10; p is 0, 1, 2 or 3, and the * terminus forms an amide bond with the carbonyl in the oligosaccharide structure. In an embodiment, AA, when occurring each time, is independently any one of Phe, Lys, Gly, Ala, Leu, Asn, Val, Ile, Pro, Trp, Ser, Tyr, Cys, Met, Asp, Gln, Glu, Thr, Arg and His, or any combination thereof. In an embodiment, n is an integer from 1 to 50, preferably an integer from 1 to 30, preferably an integer from 1 to 20, preferably an integer from 1 to 10, preferably 1, 2, 3, 4, 5, 6, 7, 8, 9 and 10.

In an embodiment, $L^1$ includes a cleavable sequence of an amino acid sequence that is enzymatically cleavable, where the amino acid sequence that is enzymatically cleavable includes 1, 2, 3, 4, 5, 6, 7, 8, 9 or 10 amino acids. In an embodiment, the amino acid sequence that is enzymatically cleavable is selected from -Gly-Gly-Phe-Gly-, -Phe-Lys-, -Val-Cit-, -Val-Lys-, -Gly-Phe-Leu-Gly-, -Ala-Leu-Ala-Leu-, -Ala-Ala-Ala- and a combination thereof; a preferred amino acid sequence that is enzymatically cleavable is -Gly-Gly-Phe-Gly-. In an embodiment, $L^1$ is any one of Val, Cit, Phe, Lys, Gly, Ala, Leu, Asn or any combination thereof, preferably -Gly-Gly-Phe-Gly-, -Phe-Lys-, -Val-Cit-, -Val-Lys-, -Gly-Phe-Leu-Gly-, -Ala-Leu-Ala-Leu-, -Ala-Ala-Ala- and a combination thereof. In an embodiment, $L^1$ represents -Val-Cit-.

In an embodiment, Sp1 is selected from p-aminobenzyloxycarbonyl (PABC), acetal, heteroacetal and a combination thereof. Preferably, Sp1 is acetal, heteroacetal or PABC. Further preferably, the heteroacetal is selected from N,O-heteroacetal. More preferably, Sp1 is —O—CH$_2$—U— or —NH—CH$_2$—U—, where —O— or —NH— is attached to an amino acid sequence that is enzymatically cleavable, U is absent, or is CH$_2$, O, S or NH, preferably O or S.

In an embodiment, B is absent, or is —NH—CH$_2$—U—, or —NH—CH$_2$—U—(CH$_2$)$_g$—(CO)—, where g is 1, 2, 3, 4, 5 or 6, U is absent, or is CH$_2$, O, S or NH, preferably O or S. In an embodiment, B is absent. In an embodiment, B is 1) below, 2) below, or a combination of 1) and 2) below: 1) the self-immolative spacer Sp1; 2) a divalent group, or a combination of two or more divalent groups, where the divalent group is selected from: —CR$^1$R$^2$—, C$_{1-10}$ alkylene and —(CO)—. In an embodiment, B is —NH—CH$_2$—U—, or —NH—CH$_2$—U—(CH$_2$)$_g$—(CO)—, U is absent, or is CH$_2$, O, S or NH, preferably O or S. In an embodiment, B is attached to the payload by the amide bond or ester bond or ether bond. In an embodiment, B is selected from:

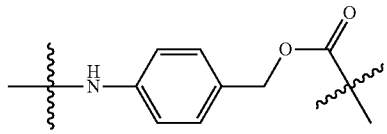 [SMILES: *Nc1ccc(COC(*)=O)cc1]

(-PABC-), —NH—CH$_2$—U—, or —NH—CH$_2$—U—(CH$_2$)$_g$—(CO)—, where g is 1, 2, 3, 4, 5 or 6; U is absent, or is CH$_2$, O, S or NH, preferably O or S.

In an embodiment, -L$^1$-B- represents -Val-Cit-PABC- or -Gly-Gly-Phe-Gly-.

In an embodiment, -L$^2$-L$^1$-B- represents -Gly-Gly-Gly-Val-Cit-PABC- or —HN—(C$_2$H$_4$—O)$_m$—(CH$_2$)$_p$-Gly-Gly-Phe-Gly-.

In an embodiment, Ld2 and each Ld1 are independently selected from bonds, or

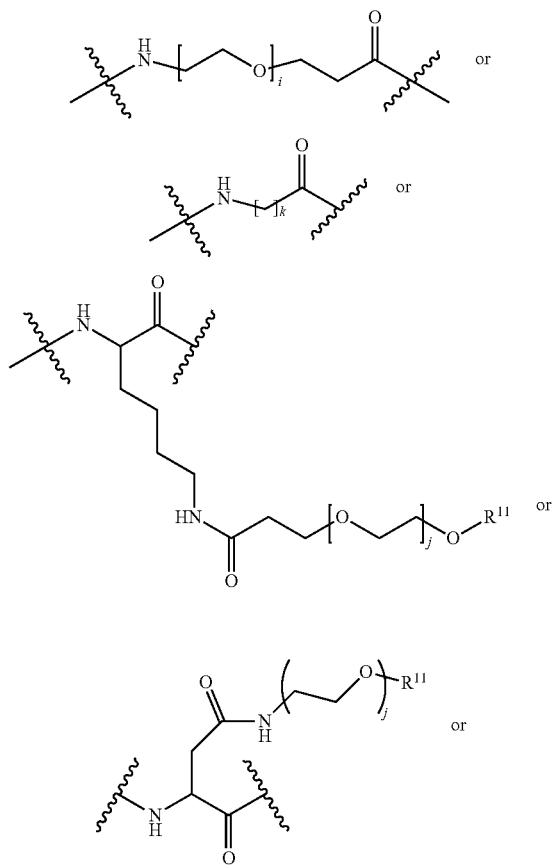

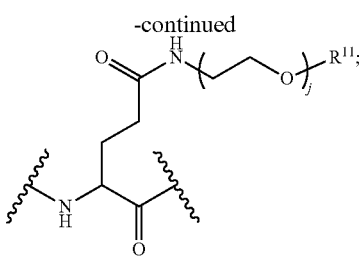

each i, j and k are independently selected from integers from 1 to 100.

In an embodiment, each i, j and k are independently selected from integers from 1 to 20. In an embodiment, each i, j and k are independently selected from integers from 1 to 12.

In an embodiment, each i is independently selected from an integer from 2 to 8, especially 4.

In an embodiment, each j is independently selected from integers from 8 to 12, especially 8 or 12.

In an embodiment, each k is independently selected from an integer from 1 to 7, especially 1 or 3 or 5.

In an embodiment, Ld2 and each Ld1 are independently selected from bonds; or C$_{1-10}$ alkylene with amino and carbonyl at both ends, respectively, or a certain length of PEG fragment (denoted as -(PEG)$_i$-) with amino and carbonyl at both ends, respectively, or one or more natural amino acids, where the natural amino acids are each independently unsubstituted or substituted with a certain length of PEG fragment (denoted as —CO-(PEG)$_j$-) on the side chain.

In an embodiment, -(PEG)$_i$- includes (O—C$_2$H$_4$)$_i$— or —(C$_2$H$_4$—O)$_i$—, and optionally, C$_{1-10}$ alkylene is attached at one end; -(PEG)$_j$- includes (O—C$_2$H$_4$)$_j$— or —(C$_2$H$_4$—O)$_j$—, and optionally, C$_{1-10}$ alkylene is attached at one end. In a very specific embodiment, -(PEG)$_i$- includes —C$_2$H$_4$—(O—C$_2$H$_4$)$_i$— or —(C$_2$H$_4$—O)$_i$—C$_2$H$_4$—.

In an embodiment, the payload may be selected from the group consisting of small molecule compounds (e.g., small molecule drugs with various mechanisms of action, including various traditional small molecule drugs, photoacoustic dynamic therapy drugs, photothermal therapy drugs, for example, chemotherapy drugs, small molecule targeted drugs, immune agonists, and the like, for example, traditional cytotoxic drugs such as cis-platinum, paclitaxel, 5-fluorouracil, cyclophosphamide and bendamustine; small molecule targeted drugs such as imatinib mesylate, gefitinib and anlotinib; immune agonists such as STING agonists and TLR agonists), nucleic acids and nucleic acid analogs, tracer molecules (including fluorescent molecules, biotin, fluorophores, chromophores, spin resonance probes and radioactive labels), short peptides, polypeptides, peptidomimetics and proteins. In an embodiment, the payload is selected from the group consisting of small molecule compounds and nucleic acid molecules. In a preferred embodiment, the payload is selected from small molecule compounds. In a more preferred embodiment, the payload is selected from the group consisting of cytotoxin and fragments thereof.

In an embodiment, the payload is a cytotoxin or a fragment thereof, having an optional moiety L derivatized to be attached into formula (I), or moiety B, moiety L$^2$ or moiety L$^1$ or a compound of formula (I-1) or formula (I-2).

In an embodiment, the cytotoxin is selected from the group consisting of drugs targeting microtubule cytoskeleton. In a preferred embodiment, the cytotoxinis selected from the group consisting of taxanes, maytenins, auristatins, epothilones, combretastatin A-4 phosphate, combretastatin A-4 and its derivatives, indole-sulfonamides, vinblastines such as vinblastine, vincristine, vincristine, vindesine, vinorelbine, vinflunine, vinglycinate, anhy-drovinblastine, dolastatin 10 and its analogs, halichondrin B, indole-3-oxoacetamides, podophyllotoxins, 7-diethylamino-3-(2'-benzoxazolyl)-coumarin (DBC), discodermolide and laulimalide. In another embodiment, the cytotoxin is selected from the group consisting of DNA topoisomerase inhibitors such as camptothecins and their derivatives, mitoxantrone and mitoguazone. In a preferred embodiment, the cytotoxin is selected from the group consisting of nitrogen mustards such as chlorambucil, chlornaphazine, cholophosphamide, estramustine, ifosfamide, nitrogen mustard, nitrobin hydrochloride, melphalan, novembichin, phenamet, phenesterine, prednimustine, trofosfamide and uramustine. In yet another preferred embodiment, the cytotoxin is selected from the group consisting of nitrosoureas such as carmustine, flubenzuron, formoterol, lomustine, nimustine and ranimustine. In an embodiment, the cytotoxin is selected from the group consisting of aziridines. In a preferred embodiment, the cytotoxin is selected from the group consisting of benzodopa, carboquone, meturedepa and uredepa. In an embodiment, the cytotoxin is selected from the group consisting of antitumor antibiotics. In a preferred embodiment, the cytotoxin is selected from the group consisting of enediyne antibiotics. In a more preferred embodiment, the cytotoxin is selected from the group consisting of dynemicin, esperamicin, neoearcinostatin and aclacinomycin. In another preferred embodiment, the cytotoxin is selected from the group consisting of actinomycin, anthramycin, bleomycins, actinomycin C, carabicin, carminomycin, sarkomycin, carminomycin, actinomycin D, daunorubicin, detorubicin, doxorubicin, pharmorubicin, esorubicin, idarubicin, marcellomycin, mitomycins, nogalamycin, olivomycin, peplomycin, porfiromycin, puromycin, quelamycin, rodorubicin, streptonigrin, streptozocin, zinostatin and zorubicin. In yet another preferred embodiment, the cytotoxin is selected from the group consisting of trichothecenes. In a more preferred embodiment, the cytotoxin is selected from the group consisting of T-2 toxin, veracurin A, roridin A and anguidine. In an embodiment, the cytotoxin is selected from the group consisting of anti-tumor amino acid derivatives. In a preferred embodiment, the cytotoxin is selected from the group consisting of ubenimex, azaserine and 6-diazo-5-oxo-L-norleucine. In another embodiment, the cytotoxin is selected from the group consisting of folate analogs. In a preferred embodiment, the cytotoxin is selected from the group consisting of denopterin, methotrexate, pteropterin, trimetrexate and edatrexate. In an embodiment, the cytotoxin is selected from the group consisting of purine analogs. In a preferred embodiment, the cytotoxin is selected from the group consisting of fludarabine, 6-purinethiol, thiamiprine and thioguanine. In yet another embodiment, the cytotoxin is selected from the group consisting of pyrimidine analogs. In a preferred embodiment, the cytotoxin is selected from the group consisting of ancitabine, gemcitabine, enocitabine, azacitidine, 6-azauridine, carmofur, cytarabine, dideoxyuridine, doxifluridine and floxuridine. In an embodiment, the cytotoxin is selected from the group consisting of androgens. In a preferred embodiment, the cytotoxin is selected from the group consisting of calusterone, dromostanolone propionate, epitiostanol, mepitiostane and testolactone. In another embodiment, the cytotoxin is selected from the group consisting of antiadrenergic drugs. In a preferred embodiment, the cytotoxin is selected from the group consisting of aminoglutethimide, mitotane and trilostane. In an embodiment, the cytotoxin is selected from the group consisting of antiandrogens. In a preferred embodiment, the cytotoxin is selected from the group consisting of flutamide, nilutamide, bicalutamide, leuprolide acetate and goserelin. In another embodiment, the cytotoxin is selected from the group consisting of protein kinase inhibitors and proteasome inhibitors. In another embodiment, the cytotoxin is selected from the group consisting of vinblastins, colchicines, taxanes, auristatins, maytansinoids, calicheamicin, doxonubicin, duocarmucin, SN-38, cryptophycin analogs, deruxtecan, duocarmazine, calicheamicin, centanamycin, dolastansine, pyrrolobenzodiazepine (PBD) and exatecan. In an embodiment, the cytotoxin is selected from the group consisting of vinblastins, colchicines, taxanes, auristatins and maytansinoids.

In an embodiment, the cytotoxin is exatecan or its derivative, for example, DX8951f and the like.

In an embodiment, the cytotoxin is maytansinoid, for example, DM1 and the like. It should be noted that when a cytotoxin including a thiol moiety is used, the thiol moiety can react with a maleimide moiety to form thiosuccimide, for example, maytansinoid, such as DM1, and the cytotoxin can be directly attached by the thiosuccimide. In this case, it is understood that in some embodiments, the payload and the thiol moiety together constitute the cytotoxin. Therefore, in this case, the payload represents the remainder of the cytotoxin molecule in addition to the thiol moiety.

In an embodiment, the cytotoxin is auristatin, for example, monomethyl auristatin E (MMAE), monomethyl auristatin F (MMAF), monomethyl auristatin D (MMAD), etc. The synthesis and structure of an auristatin compound are described in US20060229253, the full disclosure of which is incorporated herein by reference.

The payload contains an active group that can react with an active group in the compound of formula (I) and thus covalently conjugate the payload with the compound of formula (I). A compound containing no active group require proper derivatization to obtain the payload.

In an embodiment, the cytotoxin is the compound of the following formula (i)

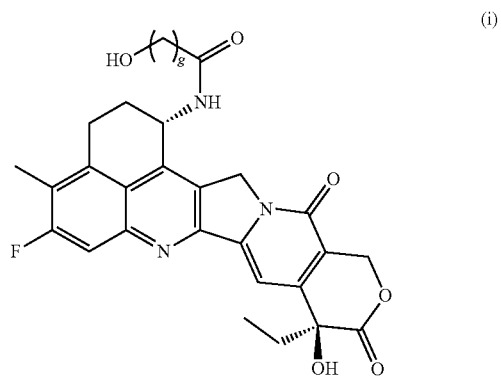

(i)

where g is any integer from 1 to 6.

In an embodiment, g is any integer from 1 to 3, preferably 1.

In an embodiment, the cytotoxin is selected from the following compounds 1 to 15; where the wavy bond represents an attachment site to the compound of formula (I).

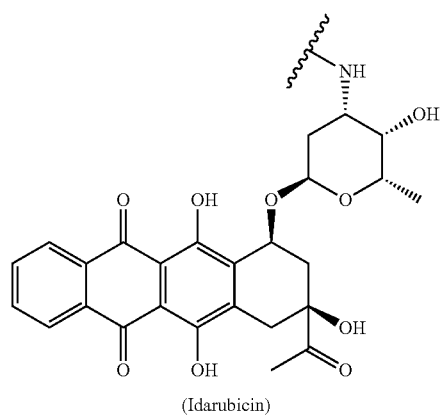
(Idarubicin) 1
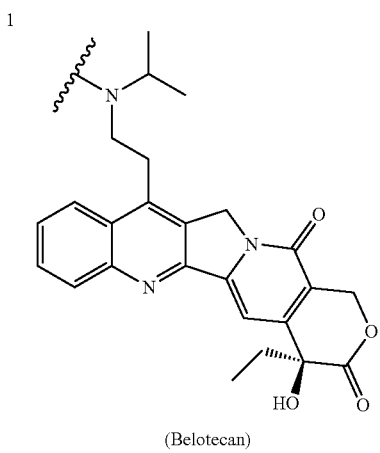
(Belotecan) 2
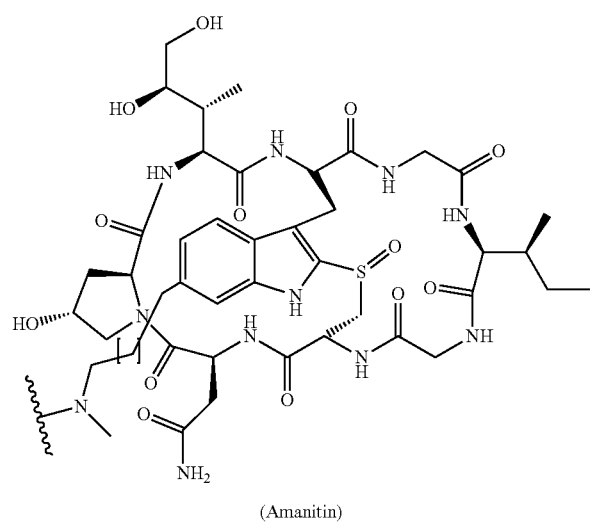
(Amanitin) 3
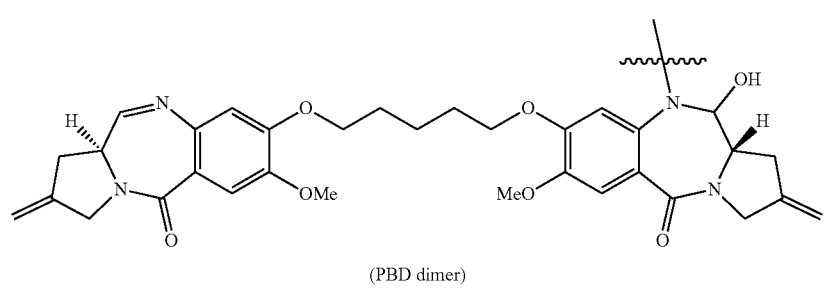
(PBD dimer) 4
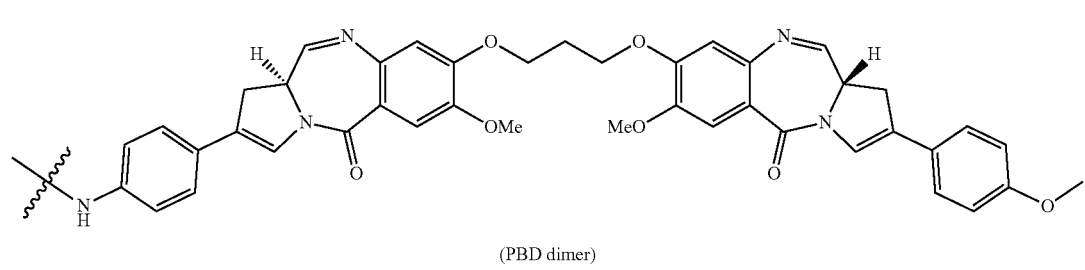
(PBD dimer) 5

-continued
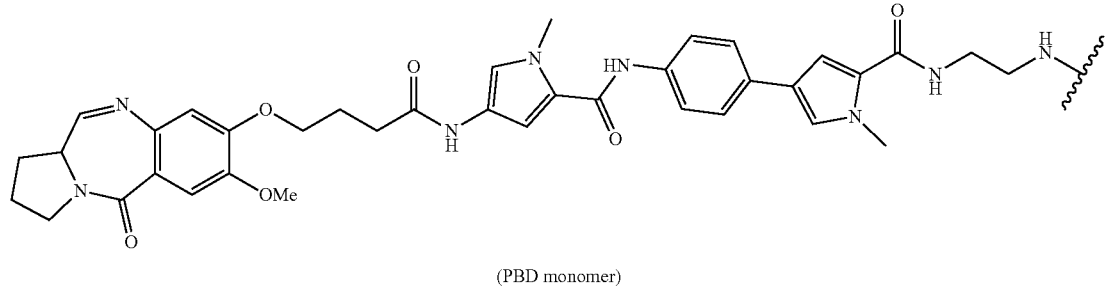
(PBD monomer)
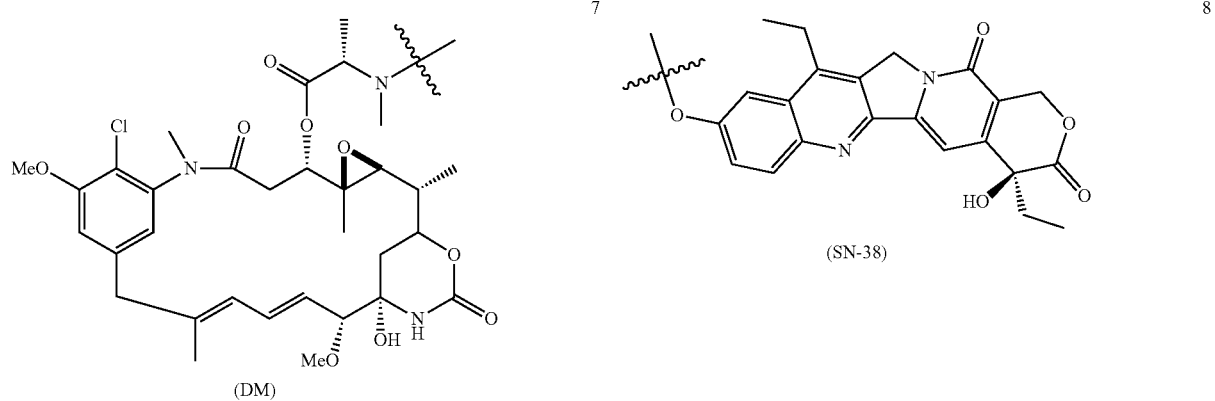
(DM)
(SN-38)
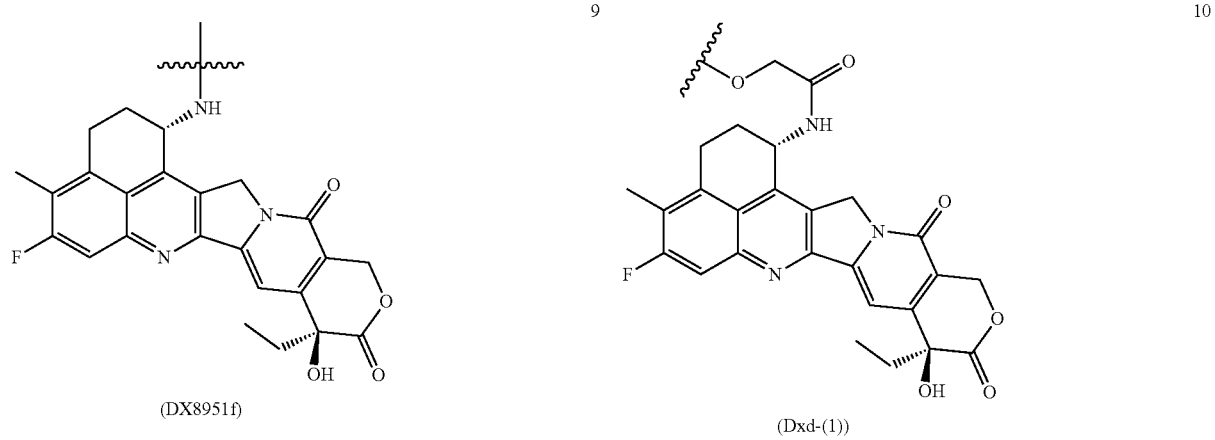
(DX8951f)
(Dxd-(1))
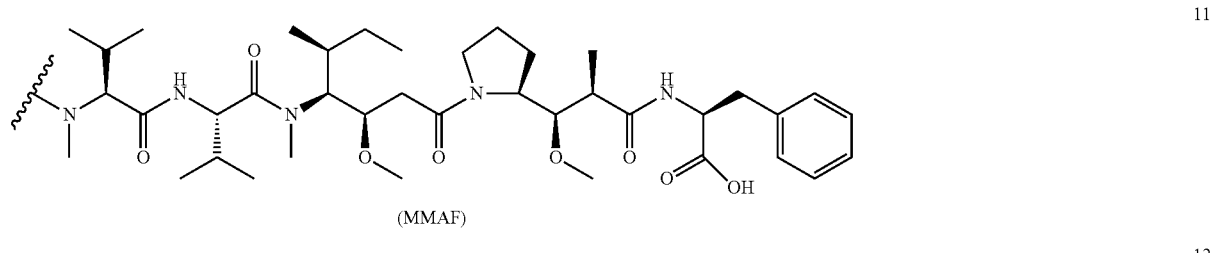
(MMAF)
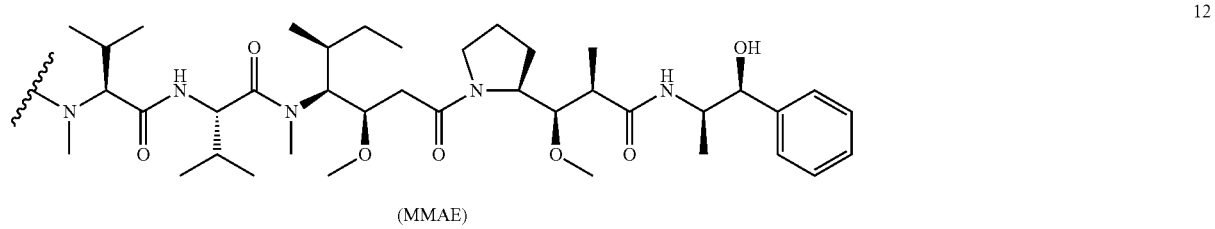
(MMAE)

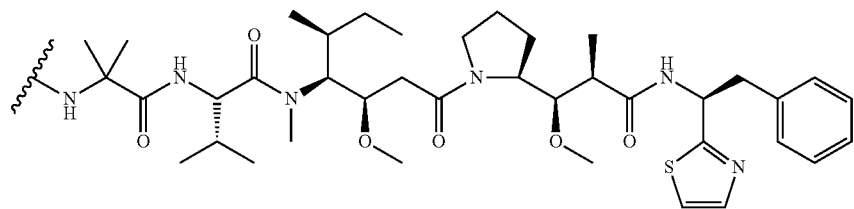

(Auristatin 0101)

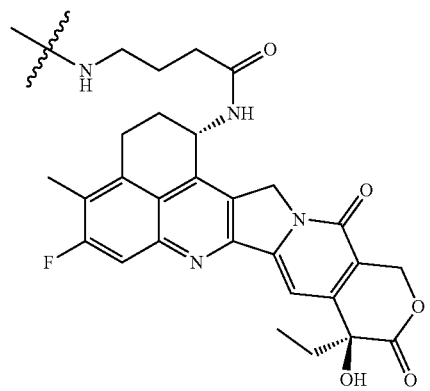

(Dxd-(2))

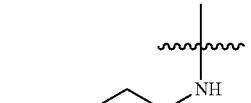

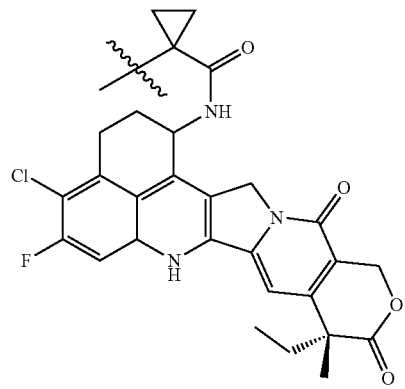

In some embodiments, the payload is selected from DX8951f (compound 9), DXd-(1) (compound 10), DXd-(2) (compound 14), and compound 15, preferably DX8951f or DXd-(1), more preferably DXd-(1).

In an embodiment, the first hexosyl or its derivative moiety is selected from glucosyl, mannosyl, galactosyl, fructosyl, gulosyl, idosyl or their derivatives, and the C-6 of the first hexosyl or its derivative moiety is in the form —C(O)—.

In an embodiment, the second hexosyl or its derivative moiety, when occurring each time, is independently selected from glucosyl, mannosyl, galactosyl, fructosyl or their derivatives.

In an embodiment, individual monosaccharide moieties in the oligosaccharide structure are attached by β-(1→4) glucosidic bonds.

In an embodiment, the derivative is independently selected from derivatives in which the hydroxyl of uronic acid or monosaccharide is replaced by acylamino (e.g., alkanoylamino, such as formylamino, acetamido, propionamido, etc., especially acetamido).

In an embodiment, the first hexosyl or its derivative moiety is selected from

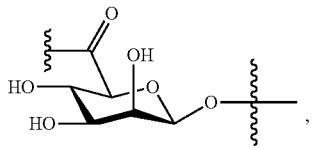

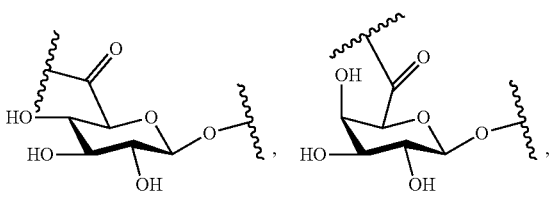

-continued
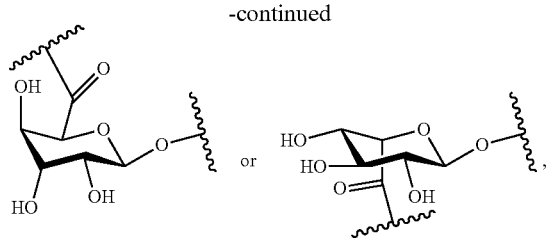
preferably, selected from
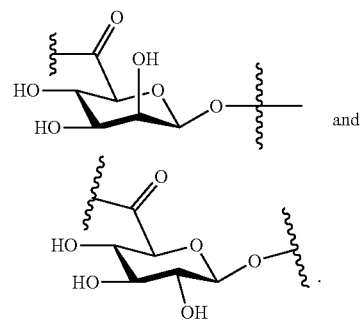
and
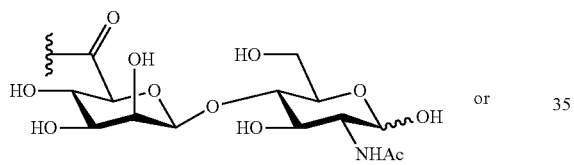
In an embodiment, f is 0.
In an embodiment, D-C(O)— is a disaccharide structure
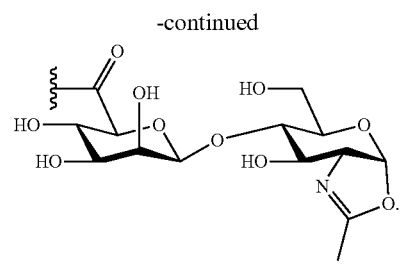
-continued
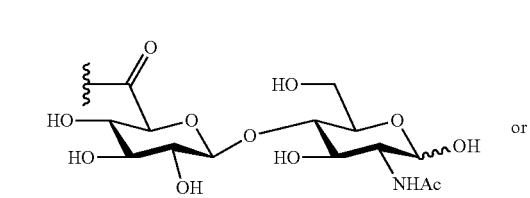
In an embodiment, D-C(O)— is a disaccharide structure
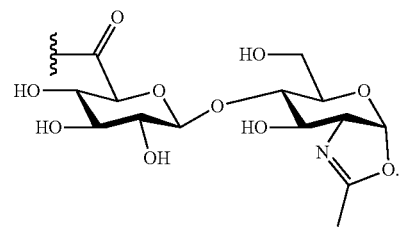
In an embodiment, the linker-payload compound having formula (I) is:

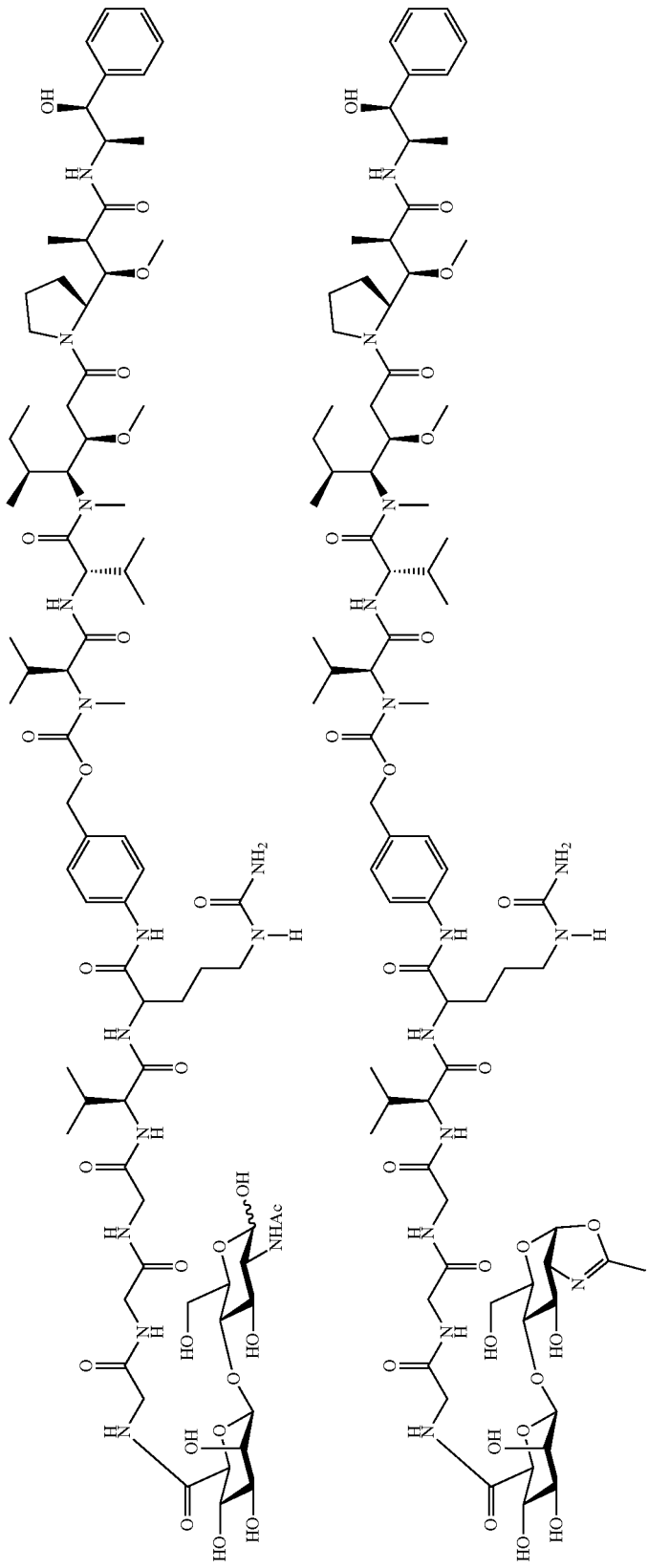

For example,

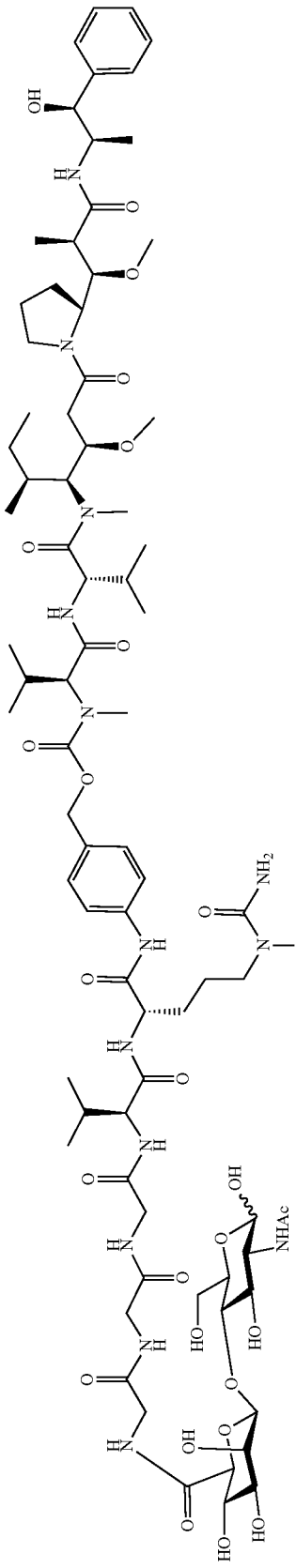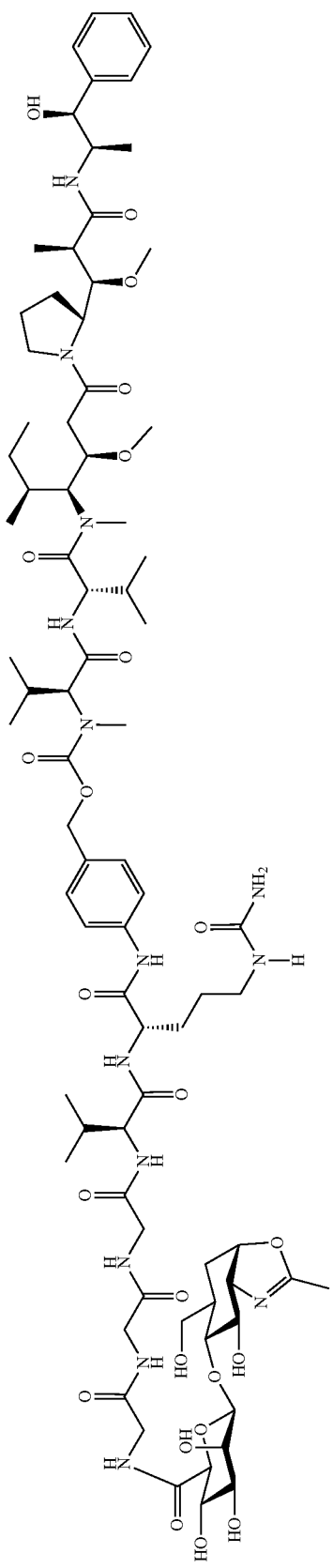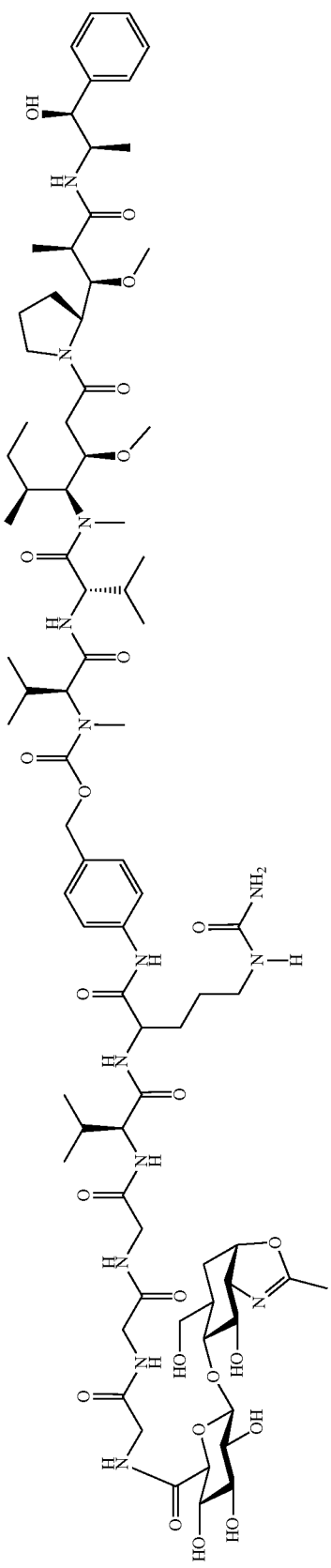

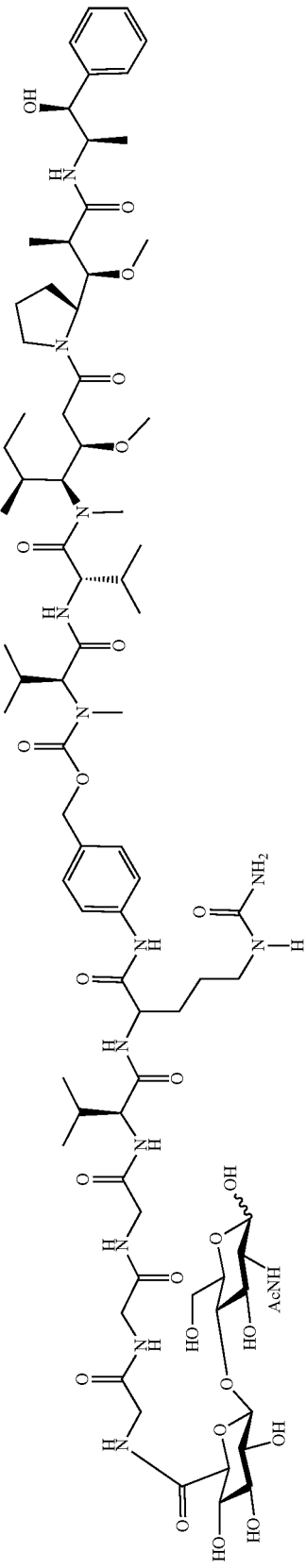

In another aspect, the present disclosure provides a linker-payload compound, which is obtained by a method including the following steps:
(i) oxidizing the primary alcohol at site 6 of an end first hexosyl unit of oligosaccharide containing the end first hexosyl unit and an end N-acetyl glucosamine (GlcNAc) unit into carboxyl to obtain an intermediate compound (a) having the carboxyl, where there are optionally 1, 2, 3, 4, 5 or 6 second hexosyl units or their derivative moieties between the end first hexosyl unit and the end N-acetyl glucosamine (GlcNAc) unit; and
(ii) reacting the carboxyl in the intermediate compound (a) obtained in step (i) with a reactive group in a linker end-payload compound (b) with the reactive group at the end to obtain the linker-payload compound.

In an embodiment of this another aspect,
the first hexosyl unit is selected from glucosyl, mannosyl, galactosyl or fructosyl; and/or
the second hexosyl, when occurring each time, is independently selected from glucosyl, mannosyl, galactosyl or fructosyl; and/or
individual monosaccharide moieties in the oligosaccharide are attached by β-(1→4) glucosidic bonds; and/or
the derivative is independently selected from derivatives in which hydroxyl of monosaccharide is replaced by acylamino (e.g., alkanoylamino, such as formylamino, acetamido, propionamido, etc., especially acetamido).

In an embodiment of this another aspect,
the first hexosyl unit is mannosyl or glucosyl; and/or
the second hexosyl unit or its derivative moiety is absent.

In an embodiment of this another aspect, the oligosaccharide in step (i) has the following structure:

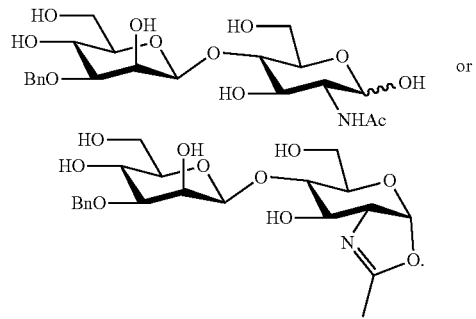

or

In an embodiment of this another aspect, the oligosaccharide in step (i) has the following structure:

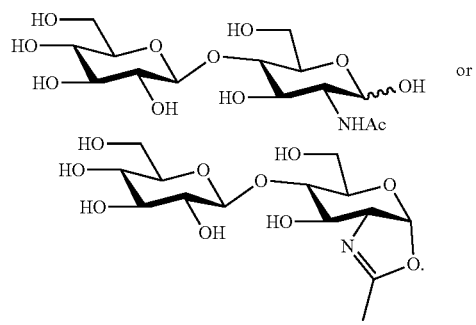

or

In an embodiment of this another aspect, a reactive group of the linker end-payload compound (b) with the reactive group at the end in step (ii) is amino In an embodiment of this another aspect, the method may further include the steps of converting the intermediate compound (a) having the carboxyl into acyl halide, and further reacting the acyl halide with the linker end-payload compound (b) with the reactive group at the end to obtain the linker-payload compound.

In an embodiment of this other aspect, the linker-payload compound is a linker-payload compound defined in the first aspect or each embodiment thereof.

Preparation Method of Linker-Payload Compound

In a second aspect, the present disclosure provides a method for preparing a linker-payload compound having formula (I). Unless otherwise specified, each variable is as defined in the first aspect or each embodiment thereof.

In an embodiment, the method includes the step of enabling D-C(O)—OH and L'-(P)$_t$ to undergo an amide formation reaction to form

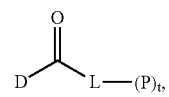

where L' is the same as L defined in the first aspect or each embodiment thereof, except that —NH— attached to D-C(O)— in L is H$_2$N— in L'.

In an embodiment, when D-C(O)— of the prepared linker-payload compound of formula (I) in

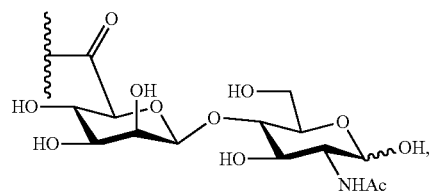

the method may further include the step of condensing

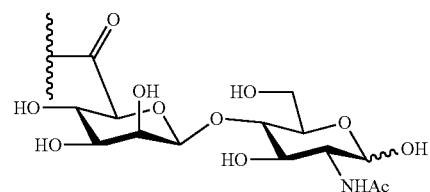

into

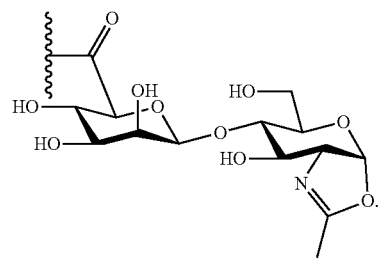

In an embodiment, the condensation is carried out in the presence of water, base and 2-chloro-1,3-dimethylimidazolidinium chloride (DMC, cas: 37091-73-9). In an embodiment, the base is inorganic base or organic base. In an embodiment, the inorganic base is potassium carbonate, potassium phosphate, etc. In an embodiment, the organic base is amine, for example tertiary amine, such as triethylamine (Et₃N).

In an embodiment, the amide formation reaction is carried out in the presence of an organic solvent, organic base and a condensation reagent. In an embodiment, the organic solvent is selected from N,N-dimethylformamide (DMF) and N,N-dimethylacetamide (DMA). In an embodiment, the organic base is selected from diisopropylethylamine (DIPEA) and N-methylmorpholine (NMM). In an embodiment, the condensation reagent is selected from HATU, HBTU, TBTU and PyBOP.

In an embodiment, D-C(O)—OH is

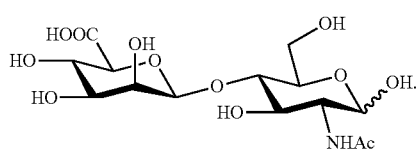

In an embodiment,

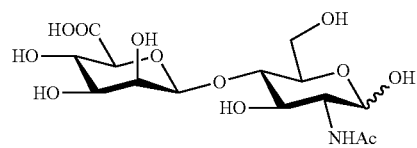

is prepared from

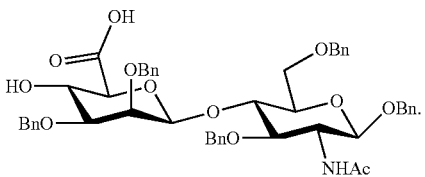

In an embodiment, the preparation is carried out under the condition that debenzylation protection is performed for the substrate. In an embodiment, the deprotection is carried out in the presence of hydrogen and a palladium catalyst. In an embodiment, the palladium catalyst is selected from palladium carbon and palladium carbon hydroxide.

In an embodiment,

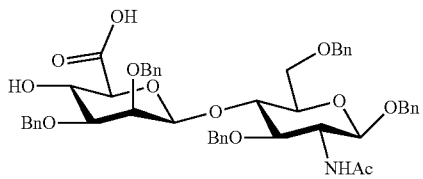

is prepared from

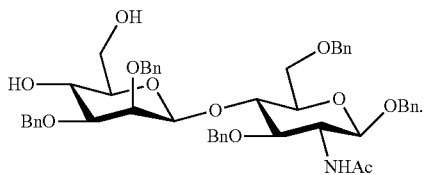

In an embodiment, the preparation is carried out in the presence of an oxidant and an optional oxidation catalyst. In an embodiment, the oxidant is iodobenzene diacetate. In an embodiment, the oxidation catalyst is 2,2,6,6-tetramethyl-1-piperidine oxide.

In an embodiment,

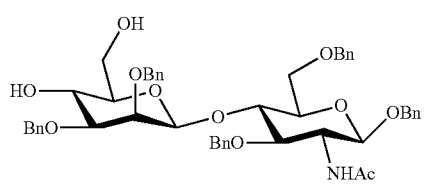

is prepared from

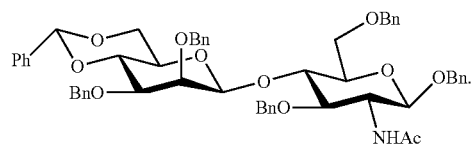

In an embodiment, the preparation is carried out in the presence of acid. In an embodiment, the acid is p-toluenesulfonic acid.

In an embodiment,

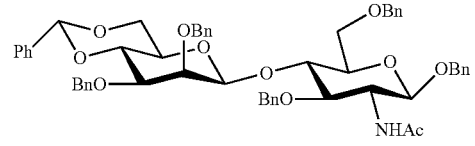

is prepared from

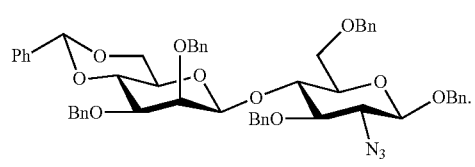

In an embodiment, the preparation is carried out in the presence of thioacetic acid (AcSH) and an organic solvent. In an embodiment, the organic solvent is selected from chloroform and pyridine or a mixture of the two.

In an embodiment,

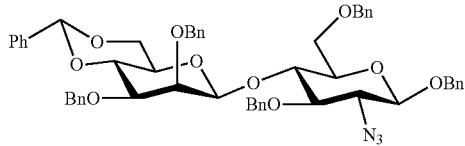

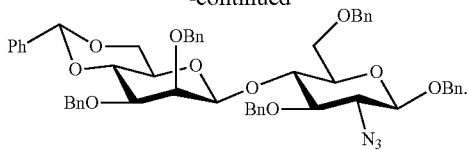

Antibody-Drug Conjugate

In a third aspect, the present disclosure provides an antibody drug-conjugate having a site-specific attachment based on an N-glycosylation site in an Fc region of an antibody, having formula (II):

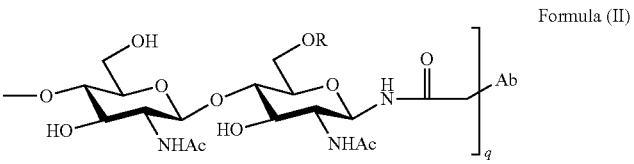

is prepared from

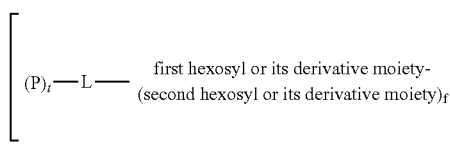

by forming a β-(1-+4) glucosidic bond. In an embodiment, the preparation is carried out under the glycosidic bond formation condition. In an embodiment, the glycosidic bond formation condition includes the use of trifluoromethanesulfonic anhydride without water.

The present disclosure further provides the following compounds:

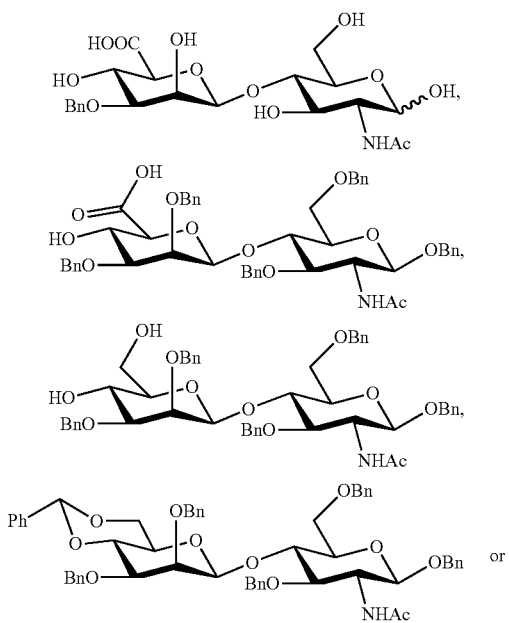

where
P is a payload;
R is hydrogen or α-L-fucosyl group;
q is 1 or 2;
Ab is an antibody or antigen-binding fragment (e.g., —NHC(O)CH$_2$— in formula (II) is from asparagine at position 297 in the Fc region of the antibody),
where the carbon at site 6 of the first hexosyl or its derivative moiety is in the form of —C(O)—; L is a linker end (for example, it can be cleaved from P chemically (e.g., by hydrolysis) or biologically (e.g., via enzymatic catalysis) to release P), and L is directly connected to carbonyl in the first hexosyl or its derivative moiety via —NH— therein, where when L is a unbranched linker end, L is attached to one P, and t is 1, while when L is a branch linker end, each branch can be attached to one P, and t is an integer greater than 1 (e.g., 2, 3, 4, 5, 6, 7, 8, 9, or 10).
f is 0, 1, 2, 3, 4, 5 or 6.

In an embodiment, the first hexosyl or its derivative moiety is selected from glucosyl, mannosyl, galactosyl, fructosyl, gulosyl, idosyl or their derivatives, and the carbon at site 6 of the first hexosyl or its derivative moiety is in the form —C(O)—.

In an embodiment, the second hexosyl or its derivative moiety, when occurring each time, is independently selected from glucosyl, mannosyl, galactosyl, fructosyl or their derivatives.

In an embodiment, the individual monosaccharide moieties are attached by β-(1→4) glycosidic bonds.

In an embodiment, the derivative is independently selected from derivatives in which the hydroxyl of uronic acid or monosaccharide is replaced by acylamino (e.g., alkanoylamino, such as formylamino, acetamido, propionamido, etc., especially acetamido).

In an embodiment, the first hexosyl or its derivative moiety is selected from

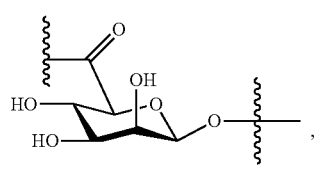

-continued

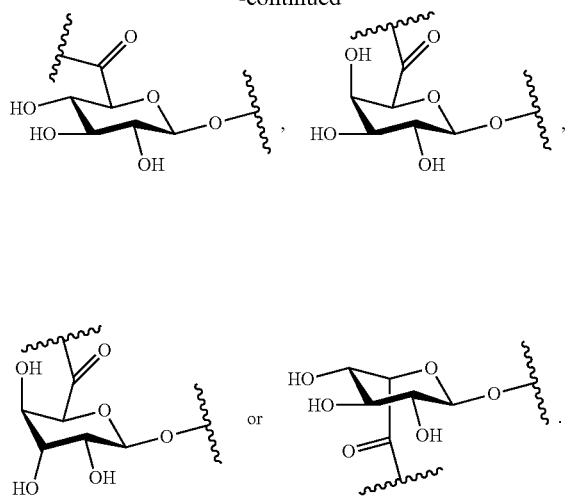

In an embodiment, f is 0.

In an embodiment, —NHC(O)CH$_2$— in formula (II) is from asparagine at position 297 in the Fc region of the antibody.

In an embodiment, the targets recognized by Ab include, but are not limited to, CD19, CD22, CD25, CD30/TN-FRSF8, CD33, CD37, CD44v6, CD56, CD70, CD71, CD74, CD79b, CD117/KIT, CD123, CD138, CD142, CD174, CD227/MUC1, CD352, CLDN18.2, DLL3, ErbB2/HER2, CN33, GPNMB, ENPP3, Nectin-4, EGFRvIII, SLC44A4/AGS-5, CEACAM5, PSMA, TIM1, LY6E, LIV1, Nectin4, SLITRK6, HGFR/cMet, SLAMF7/CS1, EGFR, BCMA, AXL, NaPi2B, GCC, STEAP1, MUC16, Mesothelin, ETBR, EphA2, 5T4, FOLR1, LAMP1, Cadherin 6, FGFR2, FGFR3, CA6, CanAg, Integrin αV, TDGF1, ephrin A4, Trop2, PTK7, NOTCH3, C4.4A, FLT3, B7H3/4, a tissue factor (TF) and ROR1/2.

In some embodiments, Ab is a monoclonal antibody. In some embodiments, Ab is an anti-human HER2 antibody or its antigen-binding fragment. Examples of the anti-human HER2 antibodies include, but are not limited to, Pertuzumab and Trastuzumab. In an embodiment, Ab is Trastuzumab.

In an embodiment, formula (II) is formula (II-1):

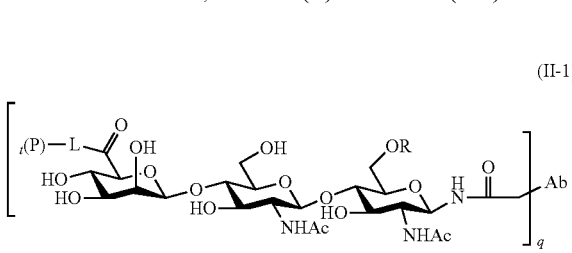

In an embodiment, formula (II) is formula (II-2):

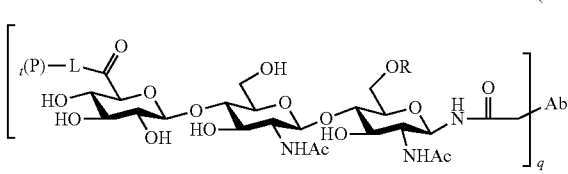

In an embodiment, formula (II) is formula (II-3):

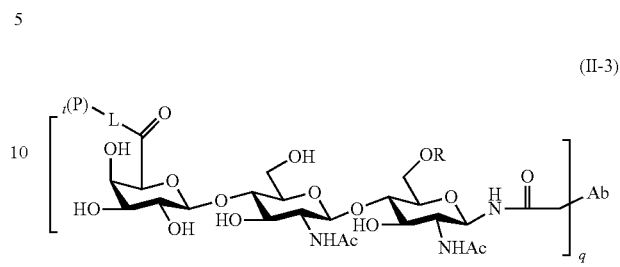

In an embodiment, formula (II) is formula (II-4):

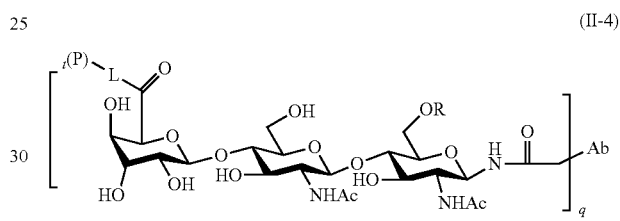

In an embodiment, formula (II) is formula (II-5):

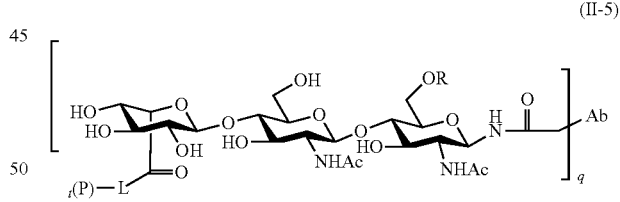

where

R is hydrogen or α-L-fucosyl group;

q is 1 or 2;

Ab is an antibody or antigen-binding fragment (e.g., —NHC(O)CH$_2$— in formula (II-1) is from asparagine at position 297 in the Fc region of the antibody); and the remaining variables are as defined in the first aspect or each embodiment thereof.

In an embodiment, formula (II) is selected from formulas (II-1), (II-2), (II-3), (II-4) and (II-5):

Formula (II-1)

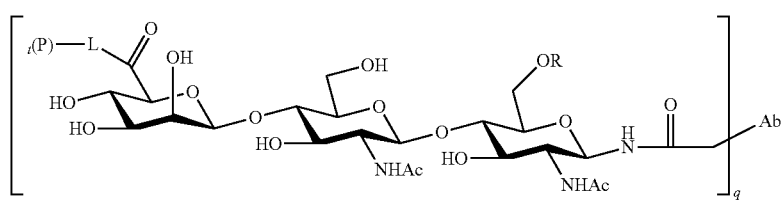

Formula (II-2)

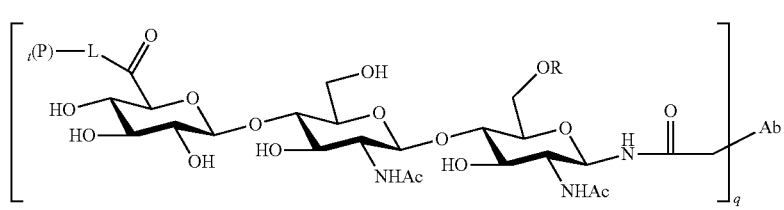

Formula (II-3)

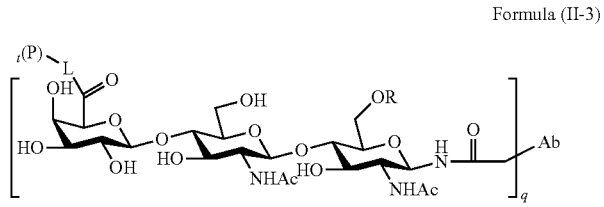

Formula (II-4)

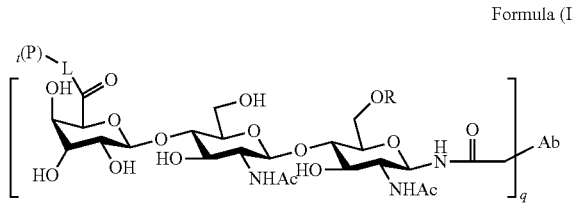

Formula (II-5)

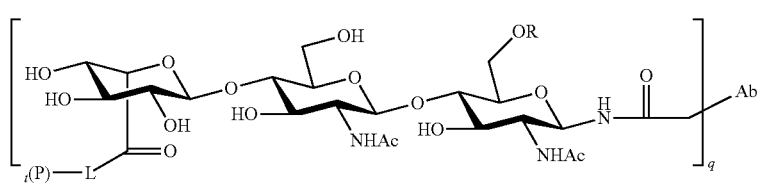

where
R is hydrogen or α-L-fucosyl group;
q is 1 or 2, for example, q is 2;
Ab is an anti-CD19 antibody, an anti-CD20 antibody, an anti-CD22 antibody, an anti-CD25 antibody, an anti-CD30/TNFRSF8 antibody, an anti-CD33 antibody, an anti-CD37 antibody, an anti-CD44v6 antibody, an anti-CD56 antibody, an anti-CD70 antibody, an anti-CD71 antibody, an anti-CD74 antibody, an anti-CD79b antibody, an anti-CD117/KITk antibody, an anti-CD123 antibody, an anti-CD138 antibody, an anti-CD142 antibody, an anti-CD174 antibody, an anti-CD227/MUC1 antibody, an anti-CD352 antibody, an anti-CLDN18.2 antibody, an anti-DLL3 antibody, an anti-ErbB2/HER2 antibody, an anti-CN33 antibody, an anti-GPNMB antibody, an anti-ENPP3 antibody, an anti-Nectin-4 antibody, an anti-EGFRvIII antibody, an anti-SLC44A4/AGS-5 antibody, an anti-CEACAM5 antibody, an anti-PSMA antibody, an anti-TIM1 antibody, an anti-LY6E antibody, an anti-LIV1 antibody, an anti-Nectin4 antibody, an anti-SLITRK6 antibody, an anti-HGFR/cMet antibody, an anti-SLAMF7/CS1 antibody, an anti-EGFR antibody, an anti-BCMA antibody, an anti-AXL antibody, an anti-NaPi2B antibody, an anti-GCC antibody, an anti-STEAP1 antibody, an anti-MUC16 antibody, an anti-mesothelin antibody, an anti-ETBR antibody, an anti-EphA2 antibody, an anti-5T4 antibody, an anti-FOLR1 antibody, an anti-LAMP1 antibody, an anti-Cadherin 6 antibody, an anti-FGFR2 antibody, an anti-FGFR3 antibody, an anti-CA6 antibody, an anti-CanAg antibody, an anti-integrin-αV antibody, an anti-TDGF1 antibody, an anti-ephrin A4 antibody, an anti-TROP2 antibody, an anti-PTK7 antibody, an anti-NOTCH3 antibody, an anti-C4.4A antibody, an anti-FLT3 antibody, an anti-B7H3/4 antibody, an anti-tissue factor (TF) antibody, and an anti-ROR1/2 antibody, preferably an anti-CD19 antibody, an anti-ErbB2/HER2 antibody, an anti-CLDN18.2 antibody, an anti-Nectin-4 antibody, an anti-FGFR3 antibody, and an anti-Trop2 antibody, more preferably an anti-ErbB2/HER2 antibody, and an anti-Trop2 antibody; particularly preferably an anti-ErbB2/HER2 antibody (e.g., Trastuzumab);

(P)$_t$-L- is selected from:
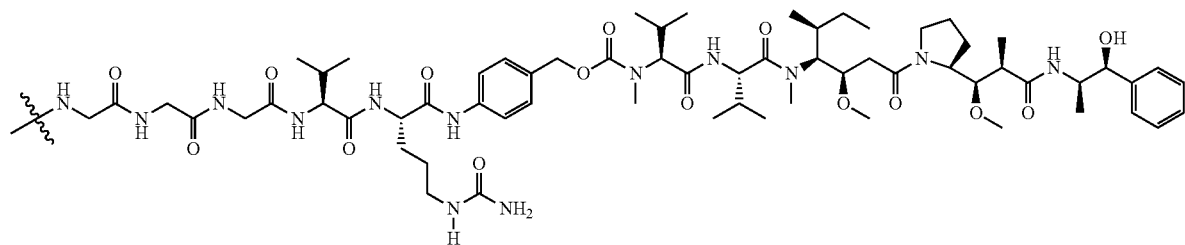
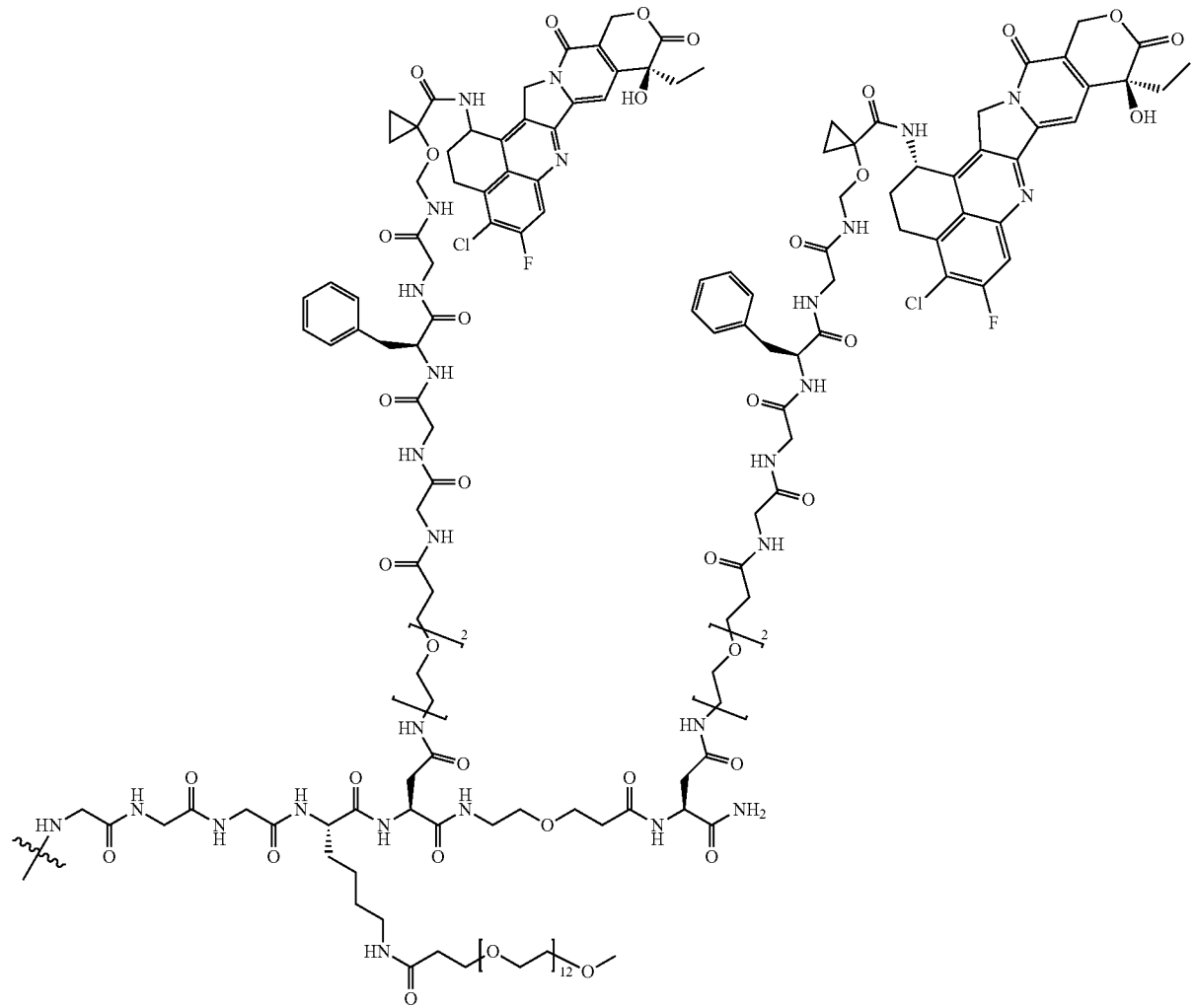

-continued
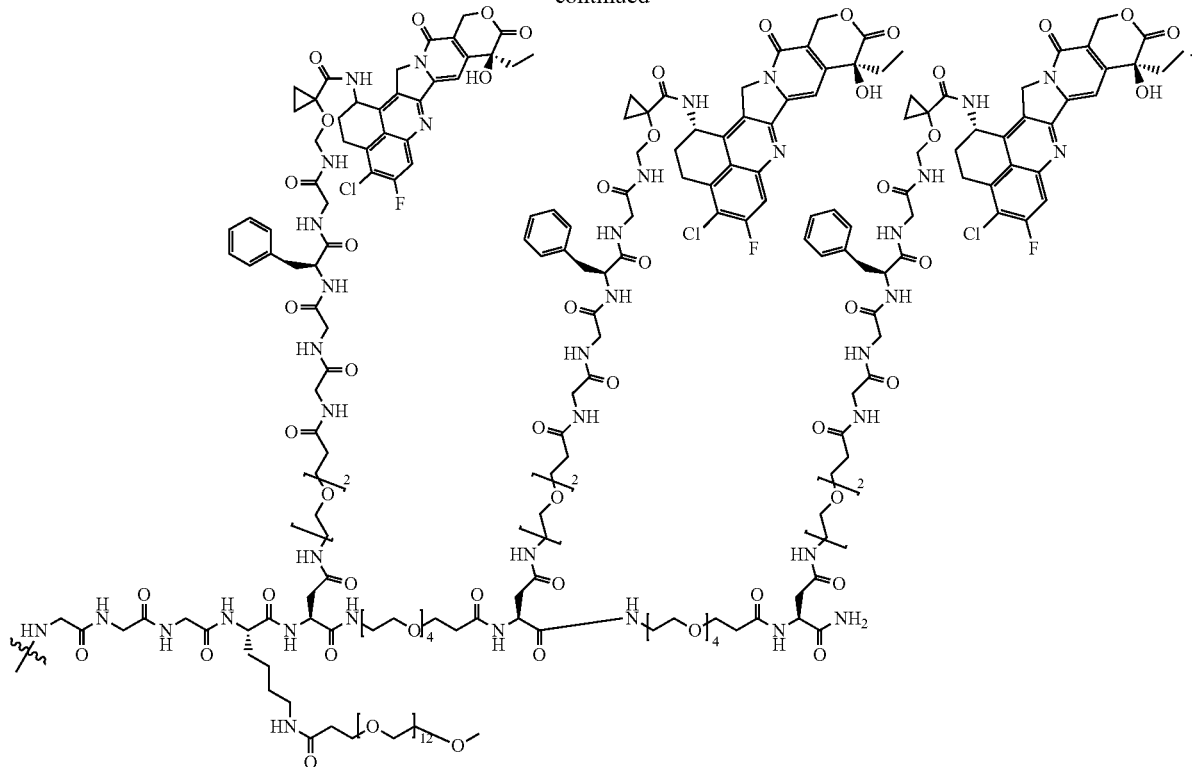
In an embodiment, R in formula (II) is α-L-fucosyl group;
q is 2;
Ab is Trastuzumab;
(P)<sub>t</sub>-L- is
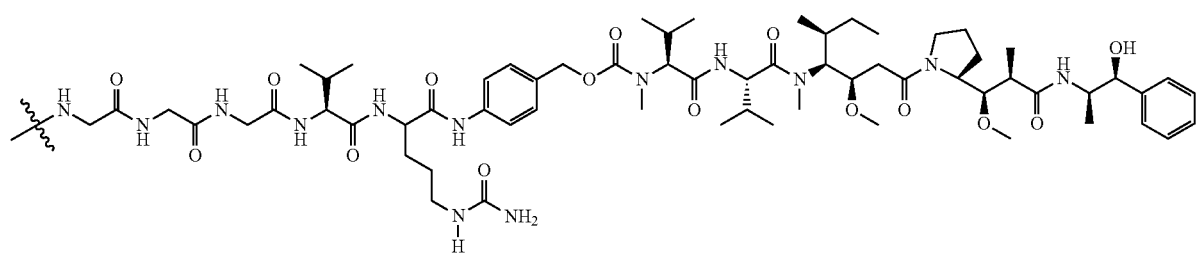 [SMILES: *NCC(=O)NCC(=O)NCC(=O)N[C@H](C(=O)NC(CCCNC(N)=O)C(=O)Nc1ccc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)cc1)C(C)C]
for example,
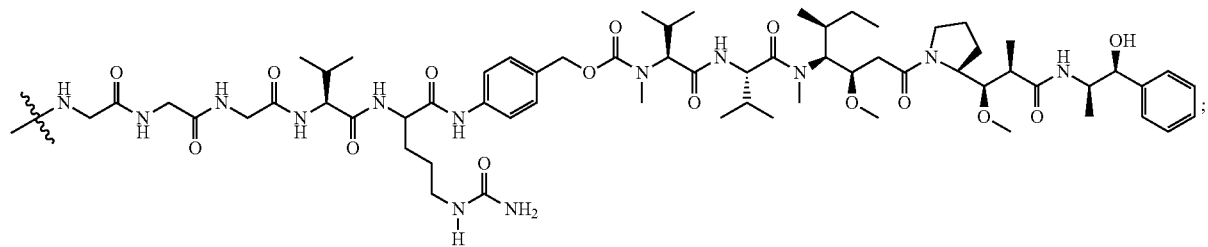 [SMILES: *NCC(=O)NCC(=O)NCC(=O)N[C@H](C(=O)NC(CCCNC(N)=O)C(=O)Nc1ccc(COC(=O)N(C)[C@H](C(=O)N[C@H](C(=O)N(C)[C@@H]([C@@H](C)CC)[C@@H](CC(=O)N2CCC[C@H]2[C@H](OC)[C@@H](C)C(=O)N[C@H](C)[C@@H](O)c2ccccc2)OC)C(C)C)C(C)C)cc1)C(C)C]

—NHC(O)CH$_2$— in formula (II) is from asparagine at position 297 in the Fc region of the antibody.

Preparation Method of Antibody-Drug Conjugate

In a fourth aspect, the present disclosure provides a method for preparing an antibody-drug conjugate having formula (II), including conjugating a linker-payload compound having formula (I) and an antibody Ab. Unless otherwise specified, each variable is as defined in the third aspect or each embodiment thereof.

In an embodiment, the method further includes the following steps:
a) removing part of the N-glycan chain from the antibody Ab, under the catalysis of glycosidase or its mutants, to afford a remodeled antibody in which the N-glycosylation site in Fc region is N-acetylglucosamine or fucosyl-α-1,6-N-acetylglucosamine moiety;
b) conjugating the glycan-remodeled antibody obtained in step a) and the linker-payload compound mentioned above, under the catalysis of glycosidase or its mutants. where the glycosidase or its mutants used in steps a) and b) may be the same or different.

In an embodiment, the glycosidase or its mutants used in steps a) and b) is fucose hydrolase, N-acetyl glucosamine endohydrolase or their mutants. In an embodiment, the N-acetyl glucosamine endohydrolase includes at least one of Endo-S (*Streptococcus pyogenes* endoglycosidase-S), Endo-F3 (*Elizabethkingia miricola* endoglycosidase-F3), Endo-S2 (Endoglycosidase-S2, *S. pyogenes* endoglycosidase-S2), Endo-Sd (Endoglycosidase-Sd, *S. pyogenes* endoglycosidase-Sd) and Endo-CC (Endoglycosidase-CC, *S. pyogenes* endonuclidase-CC), preferably, the endoglycosidases are Endo H, Endo D, Endo F2, Endo F3, Endo M, Endo CC1, Endo CC2, Endo Om, Endo S and Endo S2. In an embodiment, the enzyme is Endo S2.

In an embodiment, steps a) and b) are performed in one-pot method enzyme catalysis process.

In an embodiment, steps a) and b) are performed in one-pot method enzyme catalysis process, and the enzyme is Endo S2.

Pharmaceutical Composition and Pharmaceutical Preparation

Another object of the present disclosure is to provide a pharmaceutical composition, including a prophylactically or therapeutically effective amount of conjugate of the present disclosure, and at least one pharmaceutically acceptable carrier.

The pharmaceutical composition of the present disclosure can be administered in any way, as long as it achieves the effect of preventing, alleviating, preventing or treating symptoms in humans or animals. For example, various suitable dosage forms can be prepared according to the route of administration, especially injections such as a lyophilized powder injection, an injection or sterile injection powder.

The term "pharmaceutically acceptable" means that which does not produce undue toxicity, irritation, allergic reactions, or the like, has a reasonable ratio of advantages and disadvantages, and is effective for the intended use when in contact with patient tissues within the scope of normal medical judgment.

The term pharmaceutically acceptable carrier refers to those carrier materials that are pharmaceutically acceptable and do not interfere with the biological activity and properties of the conjugate. Examples of a waterborne carrier include, but are not limited to, buffered saline, etc. The pharmaceutically acceptable carriers further include a carrier substance that brings the composition close to physiological conditions, for example, pH regulators and buffers, toxicity regulators, etc., sodium acetate, sodium chloride, potassium chloride, calcium chloride, sodium lactate, etc.

In an embodiment, the drug/antibody ratio (DAR) of the pharmaceutical composition of the present disclosure is an integer or non-integer from 1 to 20, for example, about 1 to about 10, about 1 to about 8, about 1 to about 6, about 1 to about 4, about 1 to about 3, about 1 to about 2.5, and about 1 to about 2. In a particular embodiment, the DAR of the conjugate of the present disclosure is about 2, about 4, about 6 or about 8.

Treatment Method and Use

The antibody-drug conjugate of the present disclosure can be used for treating tumors and/or autoimmune diseases. Tumors that are sensitive to antibody-drug conjugate treatment include tumors characterized by specific tumor-associated antigens or cell surface receptors. These tumor cells can be recognized by targeting molecules in the antibody-drug conjugate, and can be then killed by payload/cytotoxin in the antibody-drug conjugate.

Therefore, in yet another aspect, the present disclosure further provides use of an antibody-drug conjugate of the present disclosure or a pharmaceutical composition of the present disclosure in preparation of drugs for treating diseases, disorders or conditions. The disease, disorder or condition is selected from tumors or autoimmune diseases.

In another aspect, the present disclosure provides the antibody-drug conjugate of the present disclosure or a pharmaceutical composition of the present disclosure, used for treating tumors or autoimmune diseases.

In a further aspect, the present disclosure provides a method for treating tumors or autoimmune diseases, including administering an effective amount of antibody-drug conjugate of the present disclosure or pharmaceutical composition of the present disclosure to an individual in need thereof.

In an embodiment, the antibody-drug conjugate formed by linking the anti-human HER2 or Trop2 antibody provided by the present disclosure and a small molecule cytotoxin may specifically bind to HER2 or Trop2 on the surface of a tumor cell, thereby selectively killing the tumor cell expressing HER2. In another embodiment, the present disclosure provides use of the antibody-drug conjugate of the present disclosure or the pharmaceutical composition of the present disclosure in preparation of drugs for treating diseases, disorders or conditions. The disease, disorder or condition is selected from HER2 or Trop2-positive tumors. In a more preferred embodiment, the disease, disorder or condition is selected from the group consisting of breast cancer, stomach cancer, lung cancer, ovarian cancer and urothelial cancer, etc.

The dose of the antibody-drug conjugate given to a subject can be adjusted to a considerable extent. The dose can vary depending on the specific route of administration and the needs of the subject, and can be judged by medical care professionals.

EXAMPLES

I. Preparation of Disaccharide Linker

Example 1: Preparation of Disaccharide Substrate Compound 1

Compound 1 was prepared by employing the following steps, the structure of which was as follows:

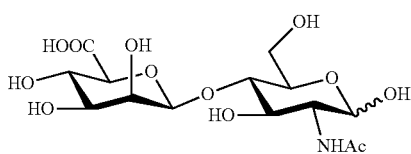

(1) Preparation of Compound 1c

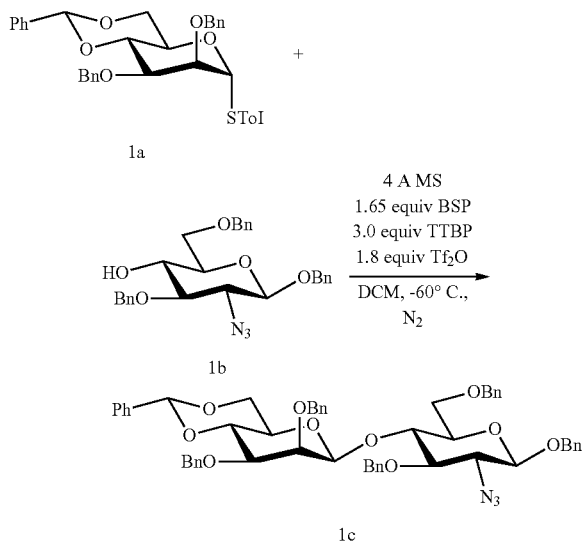

Under the condition of vacuumizing with an oil pump, a 100 mL Schlenk reaction flask was baked with a heat gun for 5 min, a pre-activated 4A molecular sieve was added after cooling, and baking was performed for another 5 min. The system was backfilled three times with nitrogen under vacuum then compound 1a (4.41 g, 7.96 mmol) was added into the system under nitrogen protection, and stirred for 3 min, and then anhydrous dichloromethane (30 mL) was added and stirred for 0.5 h. In addition, following the same operations, compound 1b (1.89 g, 3.98 mmol, dissolved in 20 mL of anhydrous dichloromethane) was added into another 50 mL Schlenk reaction flask into which the activated molecular sieve had been added, and stirred for 1 h, and pre-drying was performed to remove residual water from the system.

Under nitrogen protection, 1-(phenylsulfinyl) piperidine (BSP, 1.37 g, 6.56 mmol) and 2,4,6-tri-tert-butylpyrimidine (TTBP, 2.94 g, 11.94 mmol) were added to the above-mentioned dried compound 1a solution at room temperature (rt) and stirred for another 20 min. The reaction flask was placed in a dry ice/ethyl acetate bath, and cooled to −65° C., and trifluoromethanesulfonic anhydride (1.2 mL, 7.16 mmol) was added into the system. After 2 min, a dichloromethane solution of the previously pre-dried compound 1b was added into the system, and the resulting reaction mixture was stirred at −65° C. until the reaction was completed detected by TLC (developing solvent: EtOAc/PE=1/8) (about 3 h). A saturated sodium bicarbonate solution was added to the system for a quenching reaction, then the mixtures were extracted with dichloromethane (150 mL×3), the combined organic phase was washed successively with water and a saturated salt solution, dried over anhydrous sodium sulfate, filtered, concentrated under reduced pressure, wet loaded and separated by column chromatography (eluent: EtOAc/PE=1/12-1/10), to afford compound 1c (2.72 g, yield 75.4%, colorless viscous oily liquid). $^1$H NMR (400 MHz, chloroform-d) δ7.55 (dd, J=7.6, 2.1 Hz, 2H), 7.51-7.28 (m, 28H), 5.60 (s, 1H), 5.14 (d, J=10.4 Hz, 1H), 5.00 (d, J=12.0 Hz, 1H), 4.94 (d, J=11.8 Hz, 1H), 4.90-4.80 (m, 2H), 4.76 (d, J=12.0 Hz, 1H), 4.74-4.63 (m, 3H), 4.57 (s, 1H, H$^1$), 4.48 (d, J=12.1 Hz, 1H), 4.37 (d, J=8.1 Hz, 1H, H$^1$), 4.22-4.10 (m, 2H), 4.05 (t, J=9.3 Hz, 1H), 3.80 (d, J=3.1 Hz, 1H), 3.72 (dd, J=11.2, 2.2 Hz, 1H), 3.67-3.52 (m, 3H), 3.49 (dd, J=9.8, 3.1 Hz, 1H), 3.41 (t, J=9.3 Hz, 1H), 3.35 (dt, J=9.8, 2.9 Hz, 1H), 3.16 (td, J=9.7, 4.8 Hz, 1H). MS (ESI) m/z of $C_{54}H_{56}N_3O_{10}^+$ [M+H]$^+$: calc 906.4, found 906.7.

(2) Preparation of Compound 1d

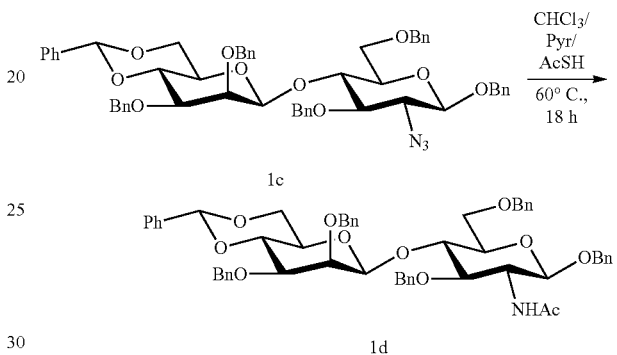

To a 25 mL Schlenk flask were added compound 1c (228 mg, 0.252 mmol), chloroform (1.2 mL), pyridine (1 mL) and AcSH (1.2 mL) successively at rt for dissolution. The reaction flask was sealed with a sleeve stopper septa, and the system was stirred at 60° C. upon the basically completion of the reaction monitored by HPLC, which took about 18 h. Most of the solvents were removed after concentration under reduced pressure, then ethyl acetate (50 mL) was added into the system, the resulting mixture was washed with saturated sodium bicarbonate solution (30 mL), 1 M hydrochloric acid (10 mL×4) and saturated sodium bicarbonate solution (30 mL) successively, the combined organic phase was dried over anhydrous sodium sulfate, and then purified by column chromatography (eluent: EtOAc/PE=1/10-1/1) after concentration under reduced pressure to afford compound 1d (200 mg, yield 86%, white solid). $^1$H NMR (400 MHz, chloroform-d) δ 7.57-7.49 (m, 2H), 7.48-7.39 (m, 5H), 7.39-7.24 (m, 23H), 5.80 (d, J=8.1 Hz, 1H), 5.59 (s, 1H), 5.00 (d, J=6.7 Hz, 1H), 4.97-4.87 (m, 3H), 4.87-4.75 (m, 2H), 4.69-4.59 (m, 4H), 4.57 (s, 1H), 4.45 (d, J=12.0 Hz, 1H), 4.19-4.05 (m, 3H), 3.96 (t, J=7.3 Hz, 1H), 3.85-3.76 (m, 2H), 3.73-3.59 (m, 4H), 3.49 (dd, J=9.8, 3.1 Hz, 1H), 3.18 (td, J=9.7, 4.8 Hz, 1H), 1.77 (d, J=1.2 Hz, 3H). MS (ESI) m/z of $C_{56}H_{60}NO_{11}^+$ [M+H]$^+$: calc 922.4, found 922.4.

(3) Preparation of Compound 1e

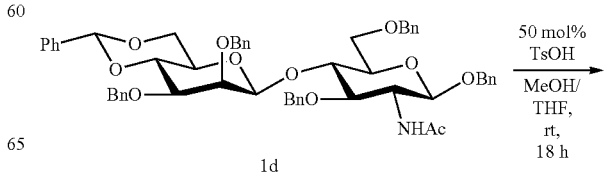

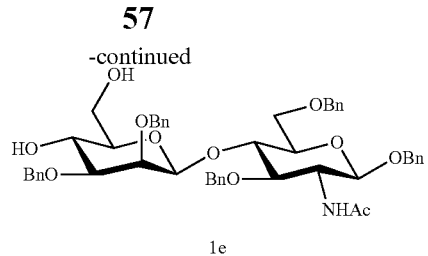

1e

At rt, compound 1d (168 mg, 0.168 mmol), p-toluenesulfonic acid monohydrate (35 mg, 0.168 mmol), methanol (5 mL), and tetrahydrofuran (5 mL) were added successively into a 100 mL single-neck flask. The system was backfilled three times with Nitrogen, and the reaction was stirred overnight at rt upon the completion of the reaction monitored by HPLC. The reaction system was quenched with saturated sodium bicarbonate solution (20 mL), extracted with dichloromethane (20 mL×3), the combined organic layer was dried over anhydrous sodium sulfate, filtered, concentrated under reduced pressure, and then purified by column chromatography (eluent: MeOH/DCM=1/20) to afford compound 1e (136 mg, yield 89%, white solid). $^1$H NMR (400 MHz, chloroform-d) δ 7.43-7.24 (m, 29H), 5.76 (d, J=7.9 Hz, 1H), 5.01 (d, J=6.9 Hz, 1H), 4.94 (dd, J=11.8, 2.3 Hz, 2H), 4.85 (d, J=11.7 Hz, 1H), 4.77 (d, J=11.8 Hz, 1H), 4.70-4.59 (m, 3H), 4.58-4.47 (m, 3H), 4.36 (d, J=11.7 Hz, 1H), 4.20 (t, J=7.9 Hz, 1H), 3.94 (t, J=7.5 Hz, 1H), 3.91-3.80 (m, 3H), 3.80-3.71 (m, 3H), 3.63-3.50 (m, 2H), 3.22-3.14 (m, 2H), 1.78 (s, 3). MS (ESI) m/z of $C_{49}H_{56}NO_{11}^+$ [M+H]$^+$: calc 834.4, found 834.5.

(4) Preparation of Compound 1f

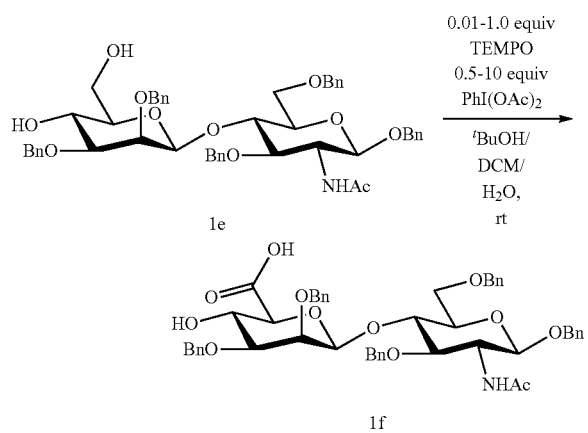

To a 100 mL single-neck flask was added compound 1e (130 mg, 0.156 mmol), dichloromethane, tert-butanol and water successively at rt, then Iodobenzene diacetate (0.5 to 10 equiv.) and 2,2,6,6-tetramethyl-1-piperidine oxide (0.01 to 1 equiv.) were added, the resulting reaction mixture was stirred overnight at rt until the reaction is completed monitored by TLC. Extraction and liquid separation were performed with dichloromethane, and a merged organic phase was dried over anhydrous sodium sulfate, filtered, concentrated, and then purified by column chromatography to afford compound 1f (100 mg, yield 75.1%, white solid). $^1$H NMR (400 MHz, chloroform-d) δ 7.42-7.31 (m, 18H), 7.30-7.27 (m, 2H), 7.25-7.20 (m, 3H), 7.15 (dd, J=6.7, 2.9 Hz, 2H), 6.06 (d, J=8.3 Hz, 1H), 4.96 (d, J=6.6 Hz, 1H), 4.93 (d, J=11.9 Hz, 1H), 4.86 (d, J=11.1 Hz, 1H), 4.81 (d, J=12.1 Hz, 1H), 4.73 (d, J=11.1 Hz, 1H), 4.71-4.65 (m, 3H), 4.65-4.57 (m, 3H), 4.49 (s, 1H), 4.46 (d, J=12.0 Hz, 1H), 4.23 (t, J=7.1 Hz, 1H), 4.15 (t, J=9.5 Hz, 1H), 3.89 (t, J=6.5 Hz, 1H), 3.86-3.65 (m, 6H), 3.54 (d, J=9.7 Hz, 1H), 3.30 (dd, J=9.3, 2.8 Hz, 1H), 1.65 (s, 3H). MS (ESI) m/z of $C_{49}H_{52}NO_{12}^-$ [M–H$^+$]$^-$: calc 846.3, found 846.3.

(5) Preparation of Compound 1

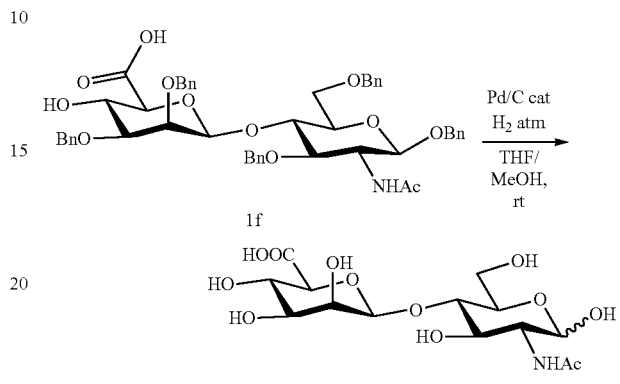

To a 50 mL single-neck flask was added compound 1f (160 mg, 0.189 mmol), tetrahydrofuran, methanol, and a palladium-carbon catalyst successively at rt, and the reaction mixture was stirred under the hydrogen atmosphere until all raw materials disappeared as detected by TLC. Filtration, concentration under reduced pressure, draining with oil pump were performed to afford compound 1 (75 mg, yield 100%, white solid). MS (ESI) m/z of $C_{14}H_{22}NO_{12}^-$ [M–H$^+$]$^-$: calc 396.1, found 396.1.

Example 2: Preparation of Disaccharide Substrate Compound 2

Compound 2 was prepared by employing the following steps, the structure of which was as follows:

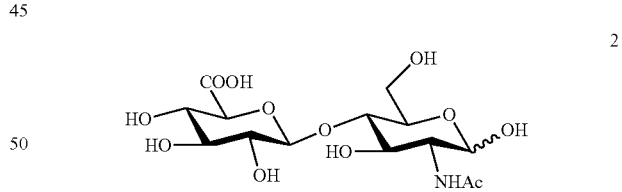

(1) Synthesis of Compound 2-1

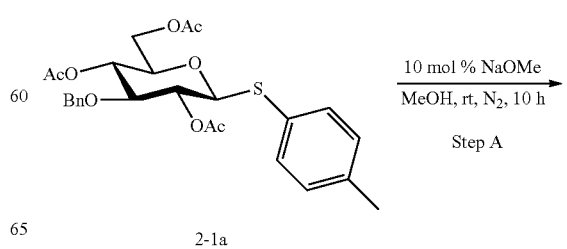

2-1a

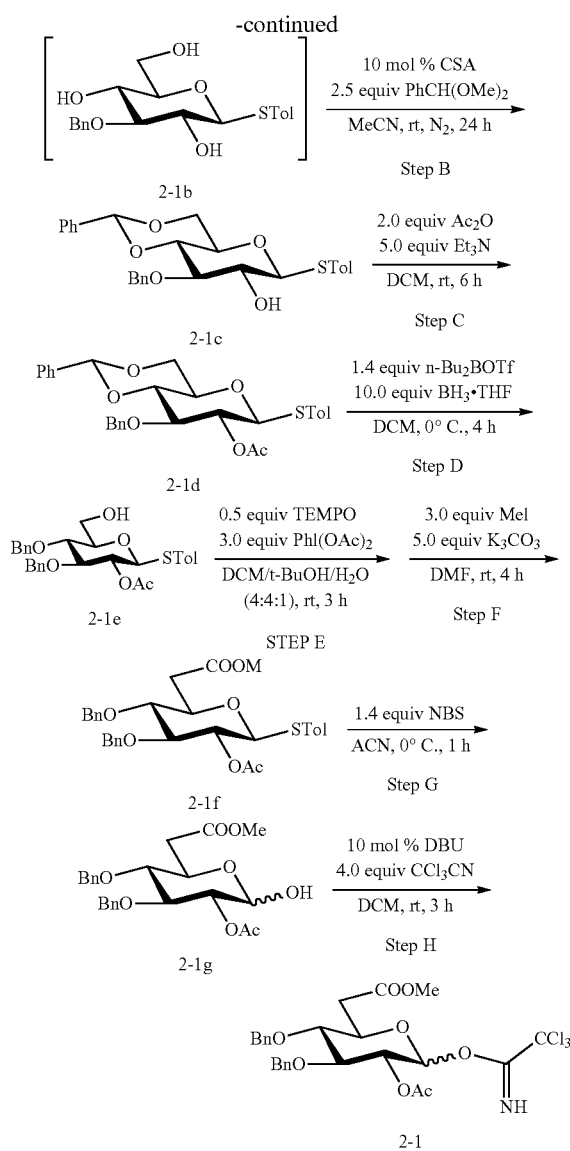

Step A: Synthesis of Compound 2-1b

Compound 2-1a (1.0 equiv., commercially available, CAS: 959153-39-0), MeOH and sodium methoxide (0.1 equiv., 5 mol/L in MeOH) were added into a single-neck flask and stirred at rt under the nitrogen atmosphere. The extent of reaction was monitored by TLC. Upon completion, the reaction was quenched by adding 1 M hydrochloric acid, and then regulated to neutral. The solvent was removed under reduced pressure, followed by the addition of a little toluene. Water was removed using the azeotropic effect under the condition of rotary evaporation under reduced pressure to afford crude product 2-1b as light yellow viscous oily liquid, and the crude product was directly used for a next reaction without further purification.

Step B: Synthesis of Compound 2-1c

To a single-neck flask were added crude product 2-1b (1 equiv.), acetonitrile, camphorsulfonic acid (0.1 equiv.) and benzaldehyde dimethyl acetal (4 equiv.) successively, the resulting reaction system was stirred overnight at rt. The reaction was monitored by TLC, upon completion (about 24 h) saturated sodium bicarbonate solution was added into the system to quench the reaction, the resulting mixture was extracted with ethyl acetate, the combined organic layer was washed with water and a saturated salt solution, dried over anhydrous sodium sulfate, filtered, concentrated and purified by column chromatography on silica gel (eluent: PE/EtOAc=5:1) to afford 2-1c (white solid, yield 83%). $^1$H NMR (400 MHz, chloroform-d) δ 7.51-7.49 (m, 2H, Ar—H), 7.45 (d, J=8.0 Hz, 2H, Ar—H), 7.42-7.37 (m, 5H, Ar—H), 7.36-7.31 (m, 3H, Ar—H), 7.15 (d, J=8.0 Hz, 2H, Ar—H), 5.56 (s, 1H, PhCH), 4.97 (d, J=11.6 Hz, 1H, PhCH$_2$), 4.81 (d, J=11.6 Hz, 1H, PhCH$_2$), 4.58 (d, J=9.6 Hz, 1H), 4.40 (dd, J=10.2, 4.8 Hz, 1H), 3.80 (dd, J=10.0, 10.4 Hz, 1H), 3.70 (dd, J=9.2, 9.2 Hz, 1H), 3.65 (dd, J=9.2, 9.2 Hz, 1H), 3.53-3.48 (m, 2H), 2.64 (br s, 1H, —OH), 2.36 (s, 3H). MS (ESI) m/z of $C_{27}H_{29}O_5S^+$ [M+H]$^+$: calc 465.2, found 465.3. $^1$H NMR data was consistent with that reported in the literature, see compound 2b1 in Nature 2007, 446, 896.

Step C: Synthesis of Compound 2-1d

To a single-neck flask was added compound 2-1c (1 equiv.), dichloromethane, and triethylamine (5 equiv.) successively, then the system was cooled to 0° C., followed by the addition of acetic anhydride (2 equiv.), the reaction was stirred for 10 min, and then the reaction system rose to room temperature and was stirred. The extent of reaction was monitored by TLC. Upon the completion (about 6 h), the reaction was quenched by adding saturated sodium bicarbonate solution. Extraction and liquid separation were performed with dichloromethane, and a combined organic layer was washed with water and a saturated salt solution, dried over anhydrous sodium sulfate, filtered, concentrated, wet loaded, and purified by column chromatography (eluent: PE/EtOAc=5:1) to afford 2-1d (white solid, yield 89%). $^1$H NMR (400 MHz, chloroform-d) δ 7.51-7.48 (m, 2H, Ar—H), 7.43-7.36 (m, 5H, Ar—H), 7.34-7.25 (m, 5H, Ar—H), 7.13 (d, J=8.0 Hz, 2H, Ar—H), 5.58 (s, 1H, PhCH), 5.00 (dd, J=8.0, 8.0 Hz, 1H, H-2), 4.87 (d, J=12.0 Hz, 1H, PhCH$_2$), 4.67 (d, J=12.0 Hz, 1H, PhCH$_2$), 4.64 (d, J=10.4 Hz, 1H, H-1), 4.39 (dd, J=10.8 Hz, J=5.2 Hz, 1H), 3.81 (t, J=10.4 Hz, 1H), 3.78-3.70 (m, 2H), 3.48 (ddd, J=9.6, 5.4, 10.0 Hz, 1H), 2.35 (s, 3H, Ar—CH$_3$), 2.05 (s, 3H, OAc). MS (ESI) m/z of $C_{29}H_{31}O_6S^+$ [M+H]$^+$: calc 507.2, found 507.4. $^1$H NMR data was consistent with that reported in the literature, see compound 3b1 in Nature 2007, 446, 896.

Step D: Synthesis of Compound 2-1e

Under the nitrogen atmosphere, the compound 2-1d (1 equiv.), dichloromethane, and borane tetrahydrofuran (10 equiv., 1 M in THF) were added successively into a 100 mL two-neck flask. The system was cooled to 0° C., followed by the dropwise addition of dibutylboron trifluoromethanesulfonate (1.4 equiv., 1.0 M in DCM). The system was maintained at 0° C. until TLC showed that the reaction completed (about 5 h). Subsequently, triethylamine solution was added into the system at 0° C. to quench the dibutylboron trifluoromethanesulfonate in the system. Then methanol was slowly dropwise added to quench the borane tetrahydrofuran. After the system no longer produces a large number of bubbles, the reaction mixture was then quenched sufficiently with water, extracted with ethyl acetate, the combine organic phase was washed with water and a saturated salt solution, dried over anhydrous sodium sulfate, filtered, concentrated, and wet loaded, and purified by rapid column chromatography on silica gel (eluent:eluent PE/EtOAc=4:1) to afford a crude product 2-1e (white solid). The product structure was confirmed by LCMS. MS (ESI) m/z of $C_{29}H_{33}O_6S^+$ [M+H]$^+$: calc 509.2, found 509.3. The crude product was directly used for the next reaction without fine purification.

Step E/F: Synthesis of Compound 2-1f

Step E: 2-1e (1 equiv.), iodosobenzene diacetate (3 equiv.), TEMPO (0.5 equiv.) and tert-butanol/dichloromethane/water (volume ratio: 4:4:1) were added successively into a single-neck flask, and the resulting mixed system was stirred at rt. The reaction was monitored by TLC (developing solvent: PE/EtOAc=2/1, containing 1 v/v % acetic acid). The reaction was quenched by adding saturated sodium thiosulfate upon completion, then extracted with dichloromethane, the combined organic layer was washed with water and a saturated salt solution, dried over anhydrous sodium sulfate, filtered, concentrated, and the resulting carboxylic acid intermediate was directly used in the next step without any further purification.

Step F: The resulting carboxylic acid intermediate in the previous step was dissolved in DMF. Iodomethane (3 equiv.) and potassium carbonate (5 equiv.) were added, and the mixture was stirred at rt. The extent of reaction was monitored by TLC (developing solvent: PE/EtOAc=5/1). After the reaction was complete (about 2 h), water was added into the system. Extraction and liquid separation were performed with ethyl acetate, and organic phases were washed with water and saturated salt solution, dried over anhydrous sodium sulfate, filtered, concentrated, and purified by column chromatography on silica gel (eluent: PE/EtOAc=7:1) to afford compound 2-1F (white solid, total yield of 59% in three steps). $^1$H NMR (400 MHz, chloroform-d) δ 7.42-7.26 (m, 12H, Ar—H), 7.16 (d, J=7.6 Hz, 2H, Ar—H), 5.02 (dd, J=8.4, 8.0 Hz, 1H), 4.83 (d, J=11.6 Hz, 1H, PhCH$_2$), 4.79 (d, J=11.2 Hz, 1H, PhCH$_2$), 4.70 (d, J=11.6 Hz, 1H), 4.64 (d, J=11.2 Hz, 1H), 4.62 (d, J=10.0 Hz, 1H), 3.97 (d, J=10.0 Hz, 1H), 3.90 (dd, J=8.4, 8.0 Hz, 1H), 3.79 (s, 3H, OMe), 3.72 (dd, J=8.8, 8.8 Hz, 1H), 2.38 (s, 3H, Ar—CH$_3$), 2.04 (s, 3H, OAc). MS (ESI) m/z of $C_{30}H_{33}O_7S^+$ [M+H]$^+$: calc 537.2, found 537.4.

Step G: Synthesis of Compound 2-1g 2-1f (1.0 equiv.) and acetone were added successively into a 50 mL single-neck flask. The system was cooled to 0° C. N-bromobutanimide (1.4 equiv.) was added. The mixture was stirred at 0° C. for about 1 h. TLC (eluent: PE/EtOAc=4/1) showed that the reaction was complete. A saturated sodium thiosulfate solution was added into the system to quench the reaction; acetone was removed by rotary evaporation under reduced pressure; water was added; and extraction and liquid separation were performed with ethyl acetate. Organic phases were merged, and washed with water and a saturated salt solution, dried over anhydrous sodium sulfate, filtered, concentrated, wet loaded, and purified by column chromatography (eluent: PE/EtOAc=6:1) to afford compound 2-1g (white solid, yield 90%). MS (ESI) m/z of $C_{23}H_{27}O_8^+$ [M+H]$^+$: calc 431.2, found 431.5.

Step H: Synthesis of Compound 2-1

Under the nitrogen atmosphere, 2-1g (1 equiv.), 1,8-diazabicyclo[5.4.0]undec-7-ene (DBU, 0.1 equiv.) and dichloromethane were added successively into a 50 mL single-neck flask; the system was cooled to 0° C. and well stirred. Subsequently, trichloroacetonitrile (4 equiv.) was added; the ice water bath was removed and the system naturally rose to rt and was stirred; the reaction was monitored by TLC (developing solvent: PE/EtOAc=2/1); after the reaction was complete (about 2 h), the solvent was removed by rotary evaporation under reduced pressure, and wet loading and purification by column chromatography (eluent: PE/EtOAc=4:1) were performed to afford compound 2-1 (light yellow viscous oily liquid, yield 87%). MS (ESI) m/z of $C_{23}H_{25}O_7^+$ [M−Cl$_3$CC(NH)O$^-$]$^+$: calc 413.2, found 413.2.

(2) Synthesis of Compound 2-2

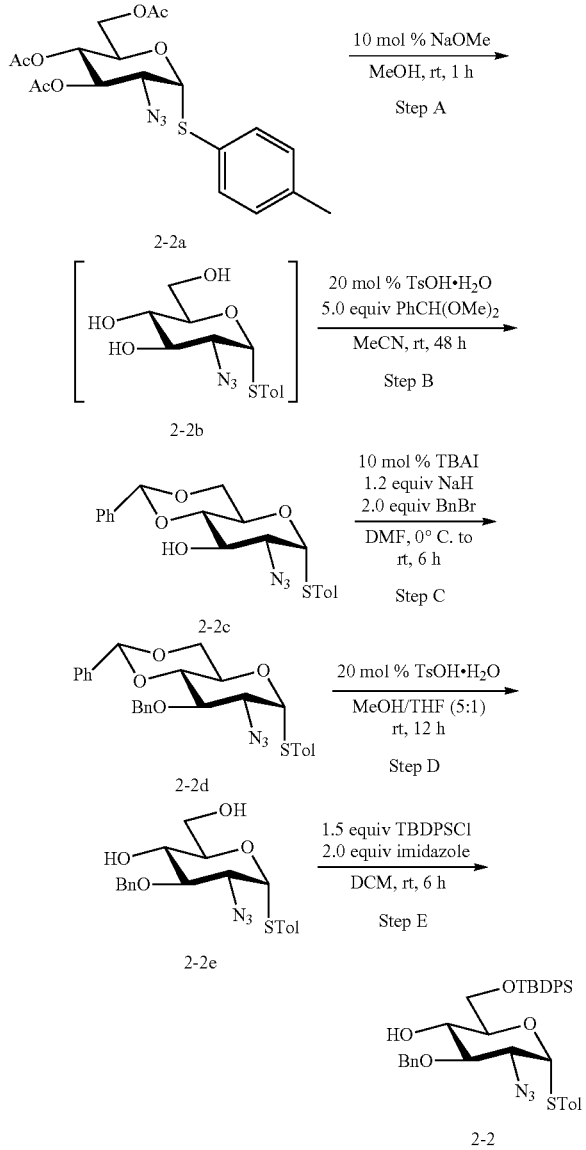

Step A: Synthesis of Compound 2-2a 2-2a (CAS: 1235137-45-7) is commercially available. See the synthesis method of compound 2 in reference *Carbohydr Res* 2016, 426, 33 for preparation.

At rt, the compound 2-2a (1 equiv.), methanol and sodium methoxide (0.1 equiv., 5 M in MeOH) were added into a single-necked flask, the resulting mixture was stirred at room temperature; the reaction was monitored by TLC (developing solvent: PE/EtOAc=2/1); after the reaction was complete (about 1 h at rt, then neutralized to pH=7 with dilute hydrochloric acid (1 M), toluene was added after the reaction solution was concentrated; and residual water in the system was removed by rotary evaporation under reduced pressure by using the azeotropic effect to afford a light brown oily crude product 2-2b, and the crude product was directly used for a next reaction without purification.

Step B: Synthesis of Compound 2-2c

At rt, p-toluenesulfonic acid monohydrate (0.2 equiv.) and anhydrous acetonitrile were added successively into the crude product 2-2b (1 equiv.) of the previous step, and fully stirred; the nitrogen atmosphere of the system was replaced, and benzaldehyde dimethyl acetal (5 equiv.) was added; the resulting reaction liquid was stirred at rt overnight until TLC (developing solvent: PE/EtOAc=5/1) showed that the reaction was complete; then a saturated sodium carbonate solution was added into the reaction system to quench the reaction; extraction and liquid separation were performed with dichloromethane; a merged organic phase was washed with water and a saturated salt water, dried over anhydrous sodium sulfate, filtered, concentrated, wet loaded, and purified by column chromatography on silica gel (eluent: PE/EtOAc=5/1) to afford compound 2-2c (white solid, total yield of 85% in two steps). $^1$H NMR (400 MHz, chloroform-d) δ 7.63-7.54 (m, 2H), 7.52-7.39 (m, 5H), 7.25-7.14 (m, 2H), 5.60 (s, 1H), 5.53 (d, J=5.4 Hz, 1H), 4.52-4.39 (m, 1H), 4.28 (dd, J=10.4, 4.9 Hz, 1H), 4.07 (t, J=9.5 Hz, 1H), 3.92 (dd, J=10.0, 5.6 Hz, 1H), 3.79 (t, J=10.3 Hz, 1H), 3.60 (t, J=9.3 Hz, 1H), 3.08 (br s, 1H), 2.40 (s, 3H). MS (ESI) m/z of $C_{20}H_{22}N_3O_4S^+$ [N+H]$^+$: calc 400.1, found 399.9. $^1$H NMR data was consistent with that reported in the literature, see compound 47 in reference Angew. Chem. Int. Ed. 2021, 60, 12413.

Step C: Synthesis of Compound 2-2d

Under the nitrogen atmosphere, compound 2-2c (1 equiv.) and anhydrous tetrahydrofuran (reaction concentration 0.2 M) were added successively into a dry two-neck flask. The two-neck flask was placed in an ice bath and cooled to 0° C. Sodium hydride (1.2 equiv., 60% content, dispersed in mineral oil) was added. Then the ice bath was removed and the system was allowed to stir at rt for 1 h, then Tetrabutylammonium iodide (0.1 equiv.) and benzyl bromide (1.5 equiv.) were added, the resulting reaction system was stirred at rt, upon completion monitored by TLC (developing solvent: PE/EtOAc=8/1) (about 6 h). After the reaction completed, water was dropwise added for quenching. Extraction and liquid separation were performed with ethyl acetate, and the merged organic phase was washed with water and a saturated salt solution, dried over anhydrous sodium sulfate, filtered, concentrated, and purified by column chromatography on silica gel (eluent: PE/EtOAc=5/1) to afford compound 2-2d (white solid, yield 97%). $^1$H NMR (400 MHz, chloroform-d) δ 7.63-7.55 (m, 2H), 7.53-7.33 (m, 10H), 7.20 (d, J=8.4 Hz, 2H), 5.67 (s, 1H), 5.56 (d, J=4.6 Hz, 1H), 5.05 (d, J=10.9 Hz, 1H), 4.90 (d, J=10.9 Hz, 1H), 4.59-4.47 (m, 1H), 4.31 (dd, J=10.4, 4.9 Hz, 1H), 4.10-3.97 (m, 2H), 3.90-3.77 (m, 2H), 2.41 (s, 3H). MS (ESI) mk of $C_{27}H_{28}N_3O_4^+$ [M+H]$^+$: calc 490.2, found 490.5. $^1$H NMR data was consistent with that reported in the literature, see compound 20 in reference Bioorg. Med. Chem. 2011, 19, 30.

Step D: Synthesis of Compound 2-2e

Compound 2-2d (1 equiv.), tetrahydrofuran/methanol (v/v=1:1, reaction concentration 0.5 M) and p-toluenesulfonic acid monohydrate (0.2 equiv.) were added into a single-neck flask and stirred overnight at rt. The extent of reaction was monitored by TLC (developing solvent: PE/EtOAc=8/1). Upon completion (about 12 h), the reaction was quenched with saturated sodium bicarbonate solution was added into the system to quench the reaction. Extraction and liquid separation were performed with ethyl acetate, and a merged organic phase was washed with water and a saturated salt solution, dried over anhydrous sodium sulfate, filtered, concentrated, wet loaded, and purified by column chromatography on silica gel (eluent: EtOAc/PE=1/1) to afford compound 2-2e. $^1$H NMR (400 MHz, chloroforms-d) δ 7.41-7.34 (m, 7H), 7.14 (d, J=8.0 Hz, 2H), 5.49 (d, J=5.2 Hz, 1H), 5.01 (d, J=11.2 Hz, 1H), 4.77 (d, J=11.2 Hz, 1H), 4.24-4.20 (m, 1H), 3.89-3.85 (m, 1H), 3.79-3.77 (m, 2H), 3.69-3.65 (m, 2H), 2.42 (br s, 1H), 2.34 (s, 3H). MS (ESI) m/z of $C_{20}H_{27}N_4O_4S^+$ [M+NH$_4$]$^+$: calc 419.2, found 419.2.

Step E: Synthesis of Compound 2-2

The compound 2-2e (1 equiv.), dichloromethane (reaction concentration 0.5 M), imidazole (2 equiv.) and tert-butylchlorodiphenylsilane (1.5 equiv.) were added successively into a single-neck flask and stirred at rt. The extent of reaction was monitored by TLC (developing solvent: EtOAc/PE=1/12). After the reaction was completed (about 6 h), the reaction was quenched by adding saturated ammonium chloride solution then extracted with dichloromethane, the combined organic layer was washed with water and a saturated salt solution, dried with anhydrous sodium sulfate, filtered, concentrated, wet loaded, and purified by column chromatography on silica gel (eluent: PE/EtOAc/DCM=15/1/1) to afford compound 2-2 (yellow viscous oily liquid, yield 66%). $^1$H NMR (400 MHz, chloroform-d) δ 7.73-7.68 (m, 4H), 7.48-7.35 (m, 13H), 7.06 (d, J=7.6 Hz, 1H), 5.49 (d, J=5.2 Hz, 1H), 4.94 (ABq, J=10.8 Hz, 2H), 4.32-4.27 (m, 1H), 3.96-3.90 (m, 2H), 3.87 (dd, J=4.8, 5.2 Hz, 1H), 3.82 (dt, J=2.8, 8.8 Hz, 1H), 3.74-3.69 (m, 1H), 2.70 (d, J=2.8 Hz, OH), 2.33 (s, 3H), 1.09 (s, 9H). MS (ESI) m/z of $C_{36}H_{42}N_3O_4SSi^+$ [M+H]$^+$: calc 640.3, found 640.2.

(3) Synthesis of Compound 2

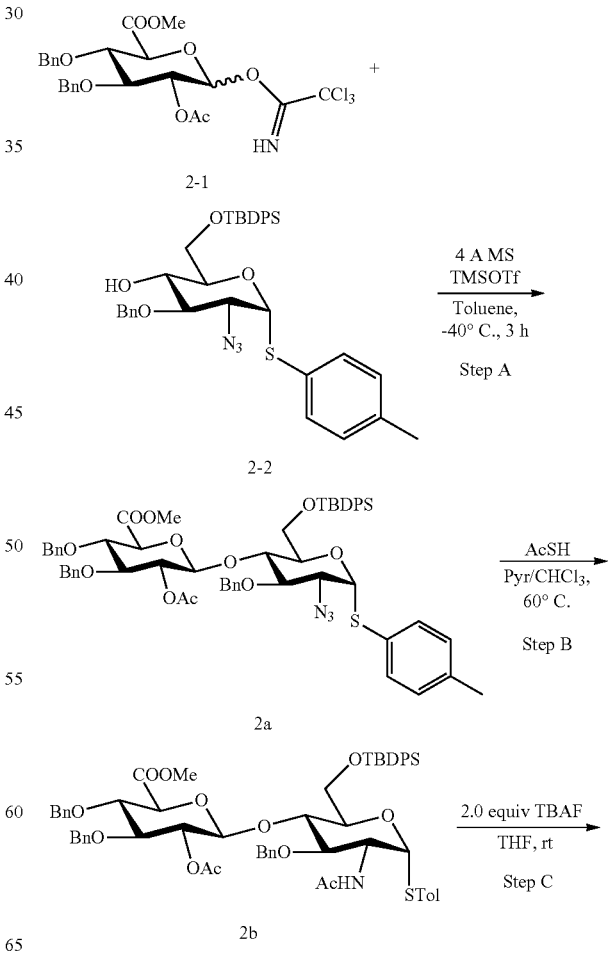

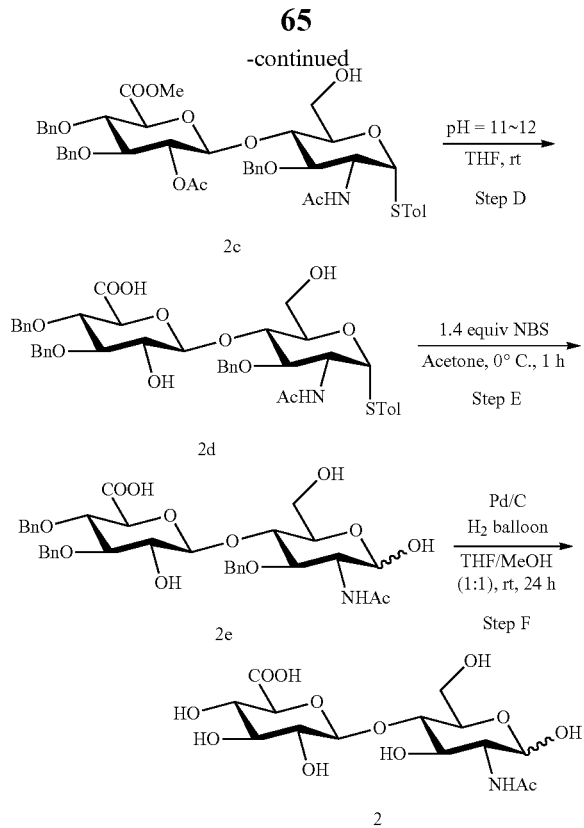

Step A: synthesis of compound 2a

A pre-activated 4A molecular sieve was added into a dry two-neck flask, baked with a heat gun under the condition of vacuumizing with an oil pump, and was naturally cooled, then backfilled with nitrogen. The above-mentioned vacuumizing-nitrogen replacement operations were repeated three times. Subsequently, compound 2-1 (2 equiv.), the compound 2-2 (1 equiv.) and anhydrous toluene was added to the system under nitrogen protection, and the resulting system was stirred at rt for 0.5 h to fully remove the residual water in the system. Subsequently, the reaction system was cooled to −40° C. and stirred. A certain amount of TMSOTf was added, the resulting reaction mixture was then stirred at this temperature until the completion of reaction monitored by TLC (about 3 h). Ttriethylamine was added into the system to quench the reaction, and filtration, concentration, wet loading, and separation by column chromatography on silica gel to afford compound 2a (white solid, yield 60%). $^1$H NMR (400 MHz, chloroform-d) δ 7.72 (d, J=6.4 Hz, 2H), 7.64 (d, J=6.4 Hz, 2H), 7.49-7.47 (m, 2H), 7.44-7.23 (m, 21H), 7.04 (d, J=7.8 Hz, 2H), 5.57 (d, J=7.2 Hz, 1H), 5.17 (d, J=7.2 Hz, 1H), 5.10 (dd, J=9.7, 8.1 Hz, 1H), 4.93 (d, J=8.0 Hz, 1H), 4.82 (d, J=11.4 Hz, 1H), 4.74 (d, J=10.9 Hz, 1H), 4.66-4.60 (m, 3H), 4.20 (dd, J=9.2, 9.2 Hz, 1H), 4.05-4.02 (m, 2H), 3.97 (dd, J=9.3, 9.2 Hz, 1H), 3.92-3.76 (m, 3H), 3.74-3.67 (m, 1H), 3.60 (s, 3H), 3.51 (dd, J=9.2, 9.2 Hz, 1H), 2.32 (s, 3H), 1.82 (s, 3H), 1.07 (s, 9H). MS (ESI) m/z of $C_{59}H_{66}N_3O_{11}SSi^+$ [M+H]$^+$: calc 1052.4, found 1052.7.

Step B: Synthesis of Compound 2b

Compound 2a (1 equiv.), andmercaptoacetic acid (CAS: 68-11-1)/pyridine/trichloromethane (v/v/v=1:1:1) were added into a reaction flask. The system rose to 60° C. and was stirred. The extend of reaction was monitored by TLC. After the reaction was complete (about 12 h), concentration under reduced pressure was performed to remove most of the solvent. An appropriate amount of ethyl acetate was added, and washed with a saturated sodium bicarbonate solution. After extraction and liquid separation, an organic phase was washed with 1 M hydrochloric acid solution. After liquid separation, washing was performed with the saturated sodium bicarbonate solution, and the resulting organic phase was dried with anhydrous sodium sulfate and then filtered, concentrated and purified by column chromatography to afford compound 2b (white solid, yield 71%). $^1$H NMR (400 MHz, chloroform-d) δ 7.70 (d, J=6.8 Hz, 2H), 7.66 (d, J=7.2 Hz, 2H), 7.44-7.28 (m, 20H), 7.26-7.21 (m, 3H), 7.00 (d, J=7.9 Hz, 2H), 5.68 (d, J=4.8 Hz, 1H), 5.36-5.30 (m, 1H), 5.09 (dd, J=9.5, 8.1 Hz, 1H), 4.92 (d, J=12.4 Hz, 1H), 4.85 (d, J=11.5 Hz, 1H), 4.75-4.66 (m, 3H), 4.63-4.57 (m, 2H), 4.29 (ddd, J=9.3, 7.7, 4.8 Hz, 1H), 4.10 (t, J=7.8 Hz, 1H), 4.01 (dd, J=11.5, 3.2 Hz, 1H), 3.94-3.89 (m, 2H), 3.86-3.84 (m, 1H), 3.80 (dd, J=11.5, 2.5 Hz, 1H), 3.67 (s, 3H), 3.60-3.51 (m, 2H), 2.28 (s, 3H), 1.85 (s, 3H), 1.82 (s, 3H), 1.07 (s, 9H). MS (ESI) m/z of $C_{61}H_{70}NO_{12}SSi^+$ [M+H]$^+$: calc 1068.4, found 1068.4.

Step C: Synthesis of Compound 2c

Compound 2b (1 equiv.) and tetrahydrofuran were added into a reaction flask. Subsequently, TBAF (2 equiv., 1 M in THF) was added into the system, and was stirred at rt. The extent of reaction was monitored by TLC. When the reaction was complete (about 10 h), a saturated ammonium chloride solution was added to quench the reaction. Then the mixture was extracted with ethyl acetate, the combined organic layer was washed with water and a saturated salt solution, dried over anhydrous sodium sulfate, filtered, concentrated and wet loaded, and preliminarily purified by column chromatography on silica gel to afford compound 2c (white solid, crude yield 56%). MS (ESI) m/z of $C_{45}H_{52}NO_{12}S^+$ [M+H]$^+$: calc 830.3, found 830.6.

Step D: Synthesis of Compound 2d

Compound 2c was dissolved in THF/MeOH (v/v=3:1). 1 M sodium hydroxide aqueous solution was slowly added to adjust the system to pH=12. The resulting reaction solution was stirred at rt until the reaction was completed (about 12 h) monitored by HPLC. The reaction was quenched with 1 M hydrochloric acid to adjust the system to pH=7 to 8. Concentration under reduced pressure was performed to remove most of the organic solvent, and the resulting crude product was purified by HPLC to afford compound 2d (white solid, yield 82%). $^1$H NMR (400 MHz, chloroform-d) δ 7.43-7.27 (m, 17H), 7.07 (d, J=7.9 Hz, 2H), 5.54 (d, J=5.0 Hz, 1H), 5.33 (d, J=8.0 Hz, 1H), 4.93 (d, J=12.1 Hz, 1H), 4.86 (d, J=11.3 Hz, 1H), 4.82-4.77 (m, 3H), 4.74 (d, J=6.8 Hz, 1H), 4.69 (d, J=12.2 Hz, 1H), 4.36 (ddd, J=10.6, 7.9, 5.0 Hz, 1H), 4.25-4.22 (m, 1H), 4.13-4.02 (m, 3H), 3.88 (t, J=8.6 Hz, 1H), 3.81 (dd, J=12.7, 2.2 Hz, 1H), 3.74 (dd, J=10.7, 8.5 Hz, 1H), 3.68-3.59 (m, 2H), 3.40 (br s, 1H), 2.30 (s, 3H), 1.77 (s, 3H). $^{13}$C NMR (100 MHz, chloroform-d) δ 170.73, 169.33, 138.20, 138.06, 137.81, 137.55, 132.37, 129.99, 129.44, 128.84, 128.76, 128.58, 128.42, 128.30, 127.90, 103.24, 88.40, 83.43, 78.89, 77.85, 77.35, 77.24, 77.03, 76.92, 76.72, 75.17, 74.93, 74.57, 74.02, 73.93, 72.95, 60.66, 52.95, 23.08, 21.06 (There were three carbon signals overlapped in the aromatic regionwithout peak appearance). MS (ESI) m/z of $C_{42}H_{46}NO_{11}S^-$ [M−H]$^-$: calc 772.3, found 772.2.

Step E: Synthesis of Compound 2e

The compound 2d was weighed and dissolved in acetone, and stirred for 5 min in an ice water bath for cooling. NBS was weighed and added into the reaction solution and reacted in the ice water bath for about 1 h. A sample was taken and sent for HPLC detection, and it was confirmed that the reaction ended. After quenching with a saturated sodium thiosulfate solution, concentration was performed to remove acetone, preparation by prep HPLC was performed, and freeze drying was performed to afford 2e (white solid, yield 45%). MS (ESI) m/z of $C_{35}H_{40}NO_{12}^-$ [M−H]$^-$: calc 666.3, found 666.4.

Step F: Synthesis of Compound 2

At rt, the compound 2e, tetrahydrofuran, methanol, and a palladium-carbon catalyst were added successively into a 50 mL single-neck flask, and the reaction system was stirred under the hydrogen atmosphere until all raw materials disappeared as detected by TLC. Filtration, concentration under reduced pressure, draining with an oil pump were performed to afford compound 2 (white solid, yield 95%). MS (ESI) m/z of $C_{14}H_{22}NO_{12}^-$ [M−H$^+$]$^-$: calc 396.1, found 396.1.

Example 3: Preparation of Disaccharide Substrate Compound 3

Compound 3 was prepared by employing the following steps, the structure of which was as follows:

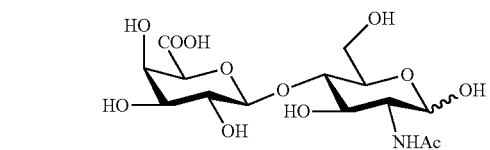

For the preparation process of the compound 3, refer to the similar synthesis method of the compound 2, and the specific route was as follows:

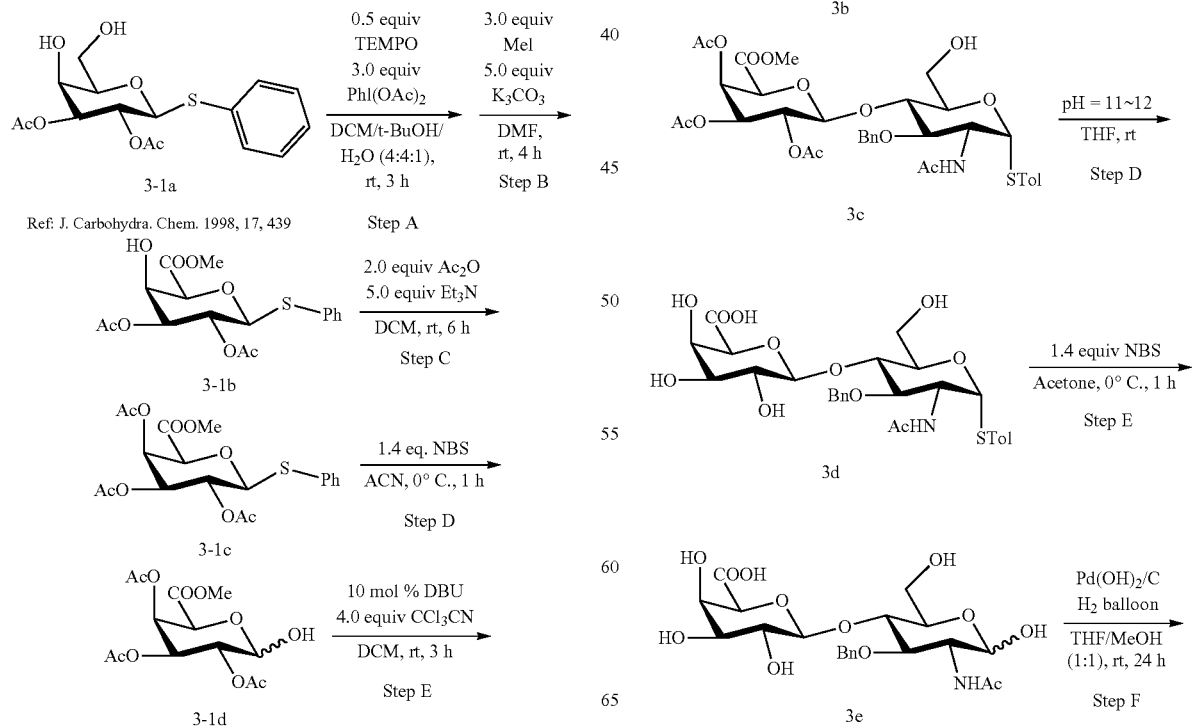

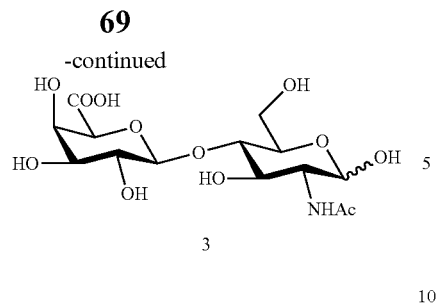

3

The final product compound 3 was verified by mass spectrometry. MS (ESI) m/z of $C_{14}H_{22}NO_{12}^-$ [M–H$^+$]$^-$: calc 396.1, found 396.0.

Example 4: Preparation of Disaccharide Substrate Compound 4

Compound 4 was prepared by employing the following steps, the structure of which was as follows:

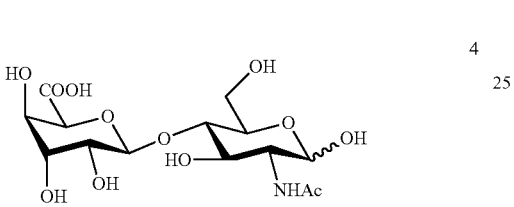

4

The preparation process of the compound 4 refers to the similar synthesis method of the compound 2, and the specific route was as follows:

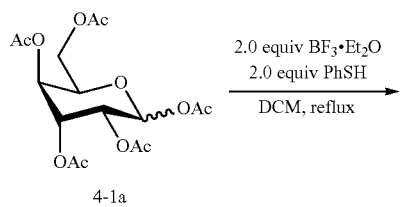

4-1a

Ref: Chem. Eur. J. 2006, 12, 845

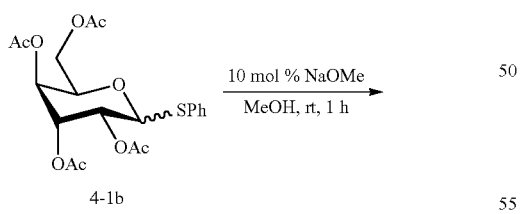

4-1b

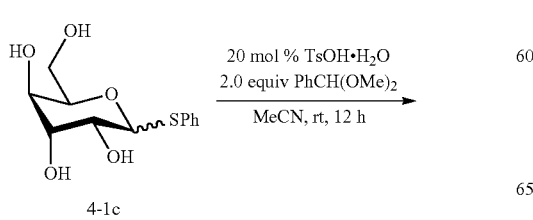

4-1c

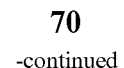

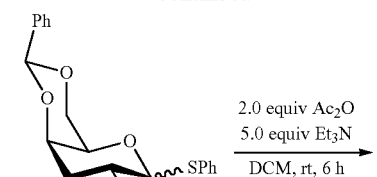

4-1d

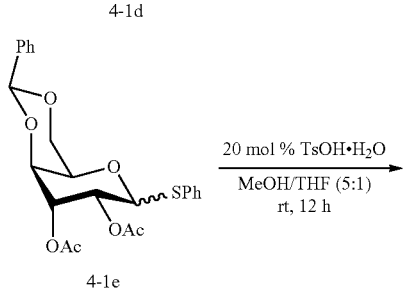

4-1e

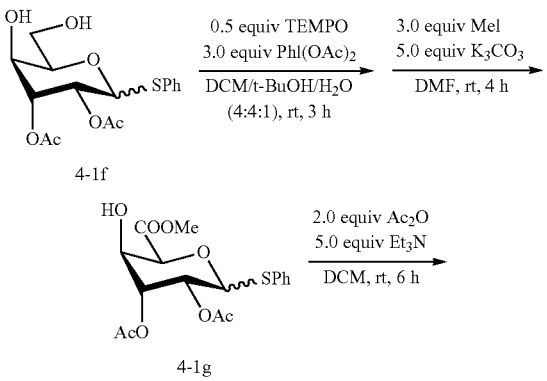

4-1f

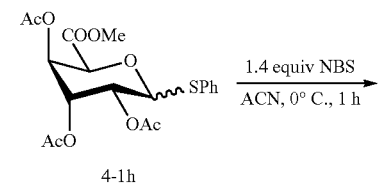

4-1g

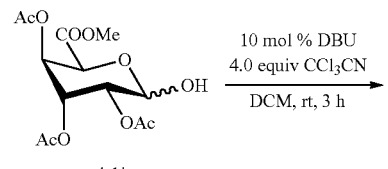

4-1h

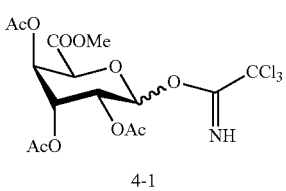

4-1i

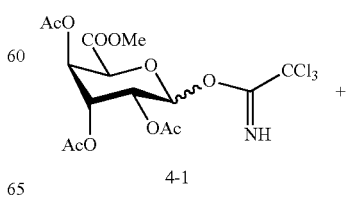

4-1

+

4-1

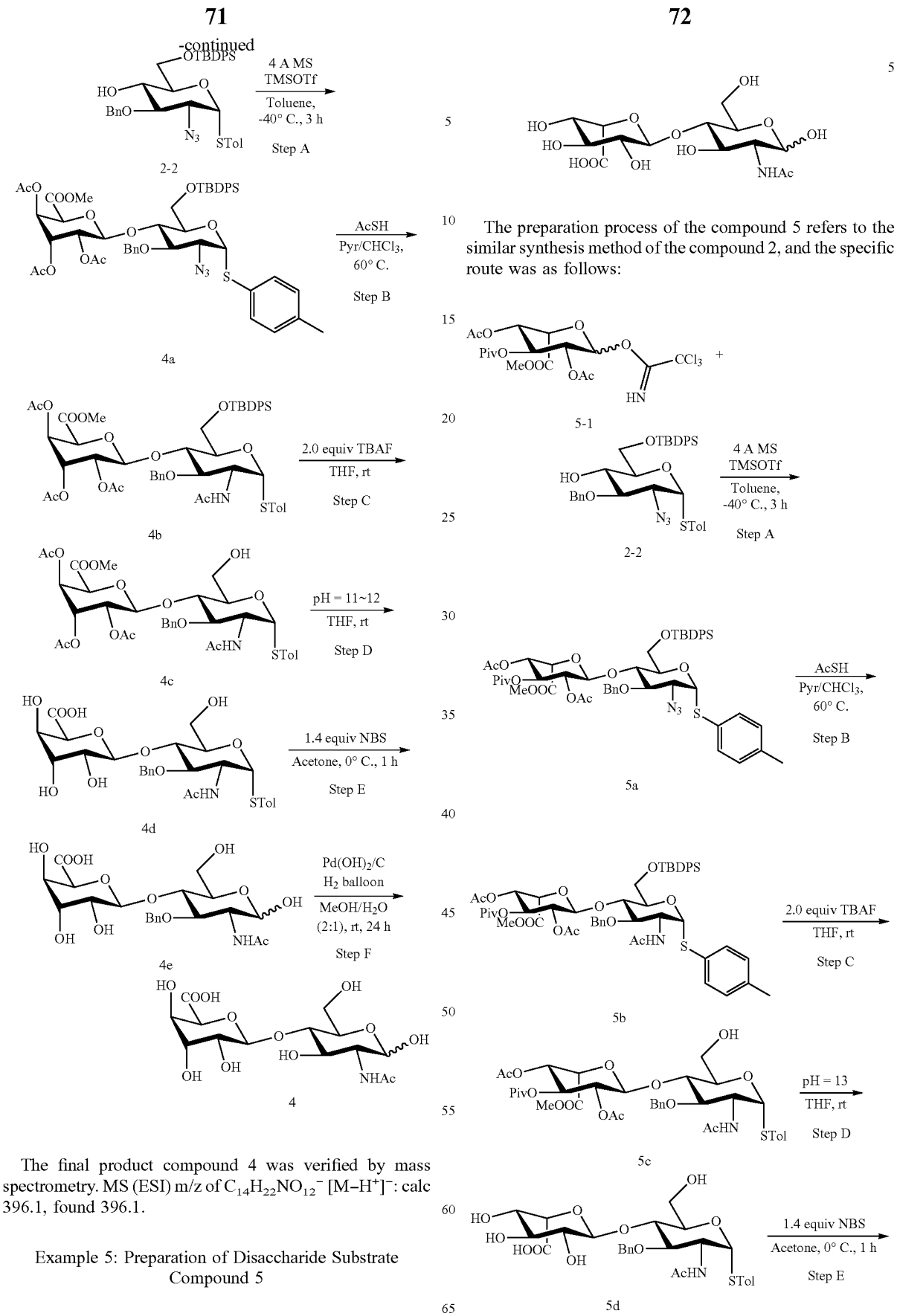

The final product compound 4 was verified by mass spectrometry. MS (ESI) m/z of $C_{14}H_{22}NO_{12}^-$ [M–H$^+$]$^-$: calc 396.1, found 396.1.

Example 5: Preparation of Disaccharide Substrate Compound 5

Compound 5 was prepared by employing the following steps, the structure of which was as follows:

The preparation process of the compound 5 refers to the similar synthesis method of the compound 2, and the specific route was as follows:

73
-continued
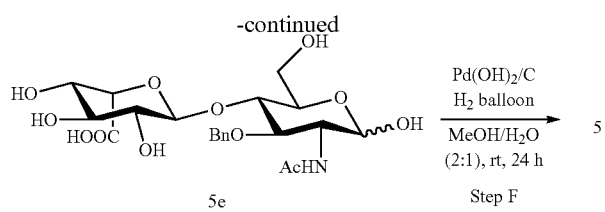
5e
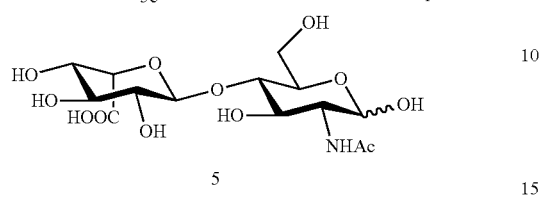
5
74
The final product compound 5 was verified by mass spectrometry. MS (ESI) m/z of $C_{14}H_{22}NO_{12}^{-}$ [M−H$^{+}$]$^{-}$: calc 396.1, found 396.0.
II. Preparation of Linker-Payload (LP Hereinafter)
Example 6: Preparation of LP-1
The structure of linker-payload 1 (LP-1) is as follows:
LP-1
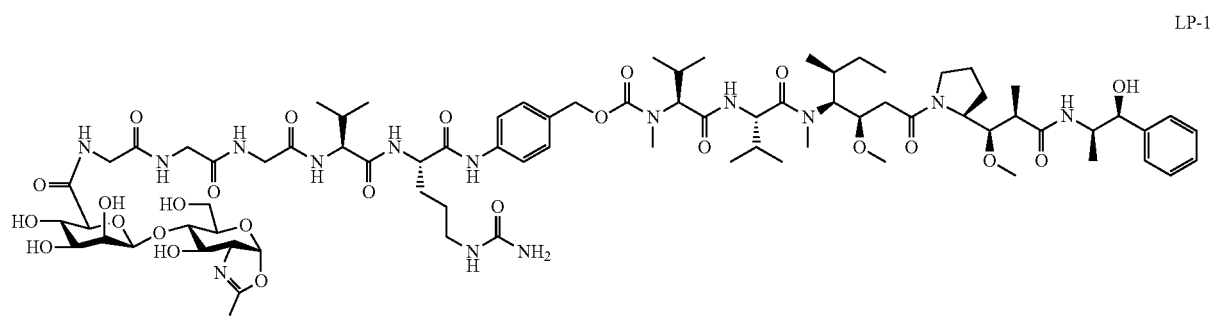
(1) Preparation of Compound LP-1b

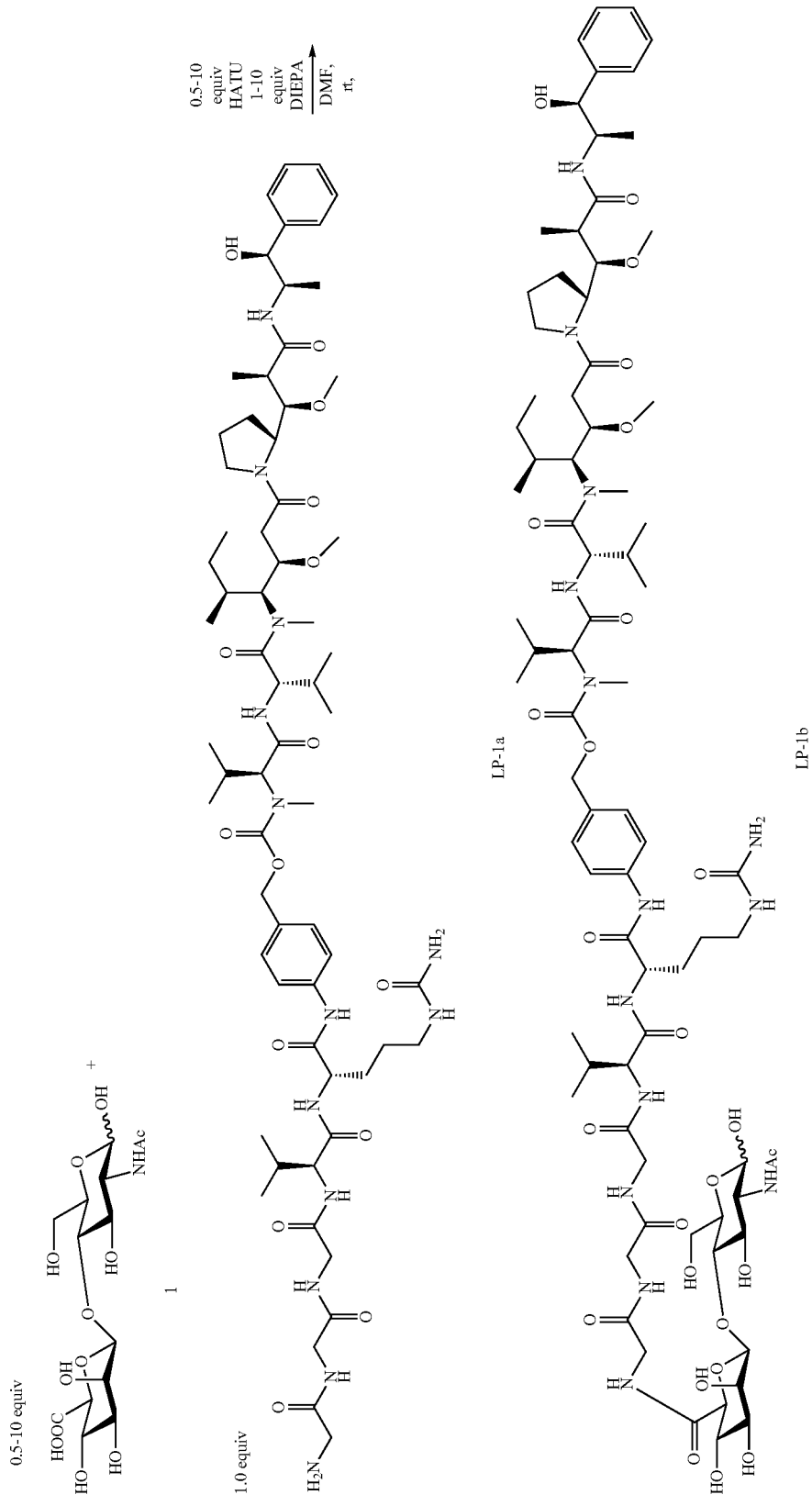

At rt, the compound 1 (0.5 to 5.0 equiv.), compound LP-1a (1.0 equiv., GGG-VC-PAB-MMAE, CAS number: 2684216-48-4, commercially available), DMF, DIPEA (1 to 10 equiv.), and HATU (0.5 to 10 equiv.) were added successively into a 10 mL single-neck flask, and the resulting reaction solution was stirred at rt until the reaction was complete as monitored by HPLC. The reaction solution was purified by semi-preparative HPLC to afford compound LP-1b (white solid, yield 81.2%). MS (ESI) m/z of $C_{78}H_{126}N_{14}O_{26}{}^{2+}$ $[M+2H]^{2+}$: calc 837.4, found 837.9.

(2) Preparation of Compound LP-1

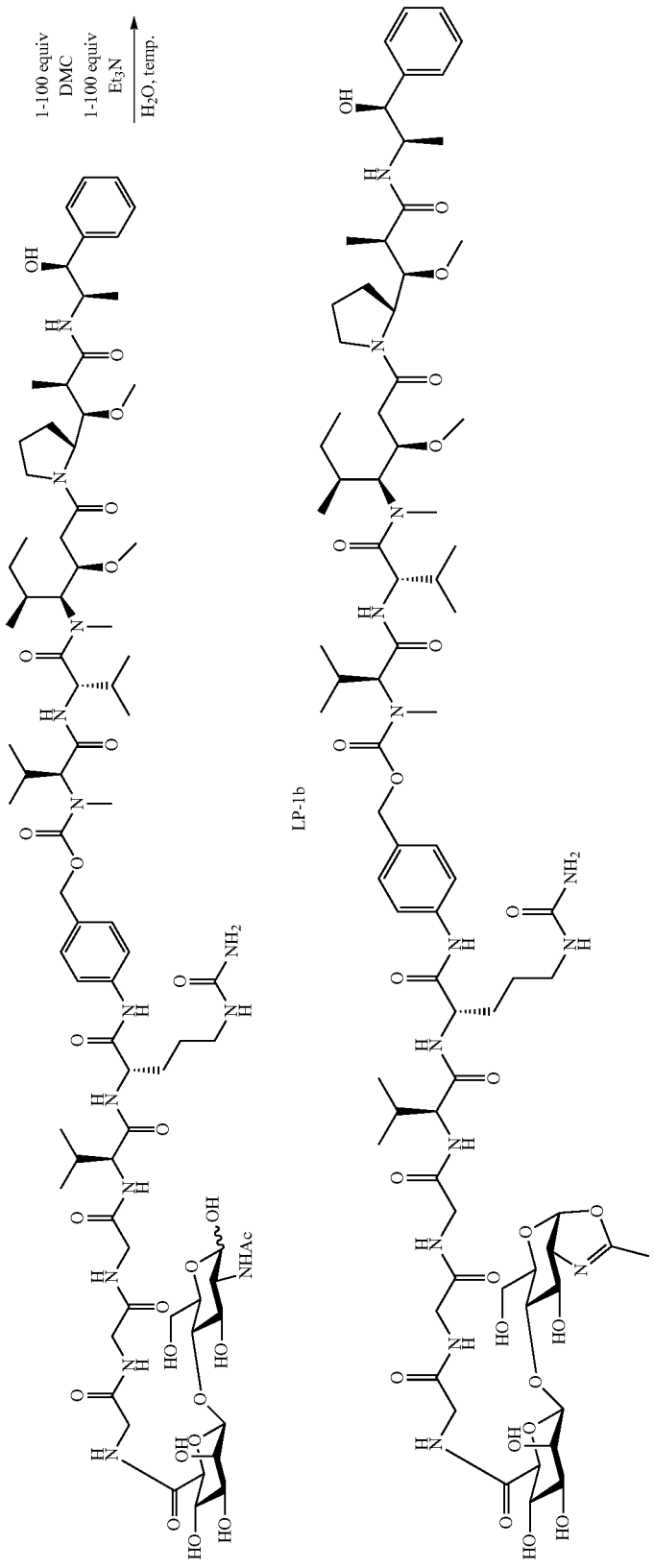

At rt, the compound LP-1b (21.7 mg, 0.013 mmol, 1 equiv.), H₂O, Et₃N (1 to 100 equiv.) and DMC (2-chloro-1,3-dimethylimidazolidinium chloride, CAS: 37091-73-9, 1 to 100 equiv.) were added successively into a 10 mL single-neck flask. The resulting reaction solution was stirred at rt, and the reaction was monitored by HPLC until the reaction was complete. The reaction solution was purified by semi-preparative HPLC to afford compound LP-1 (15.3 mg, yield 71.3%, white solid). MS (ESI) m/z of $C_{78}H_{124}N_{14}O_{25}{}^{2+}$ [M+2H]$^{2+}$: calc 828.4, found 828.6.

Example 7: Preparation of LP-2

The structure of linker-payload 2 (LP-2) was as follows:

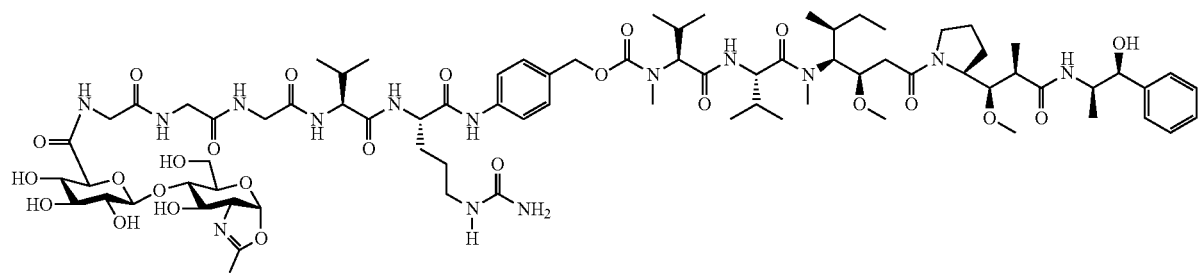

LP-2

The preparation process was as follows:

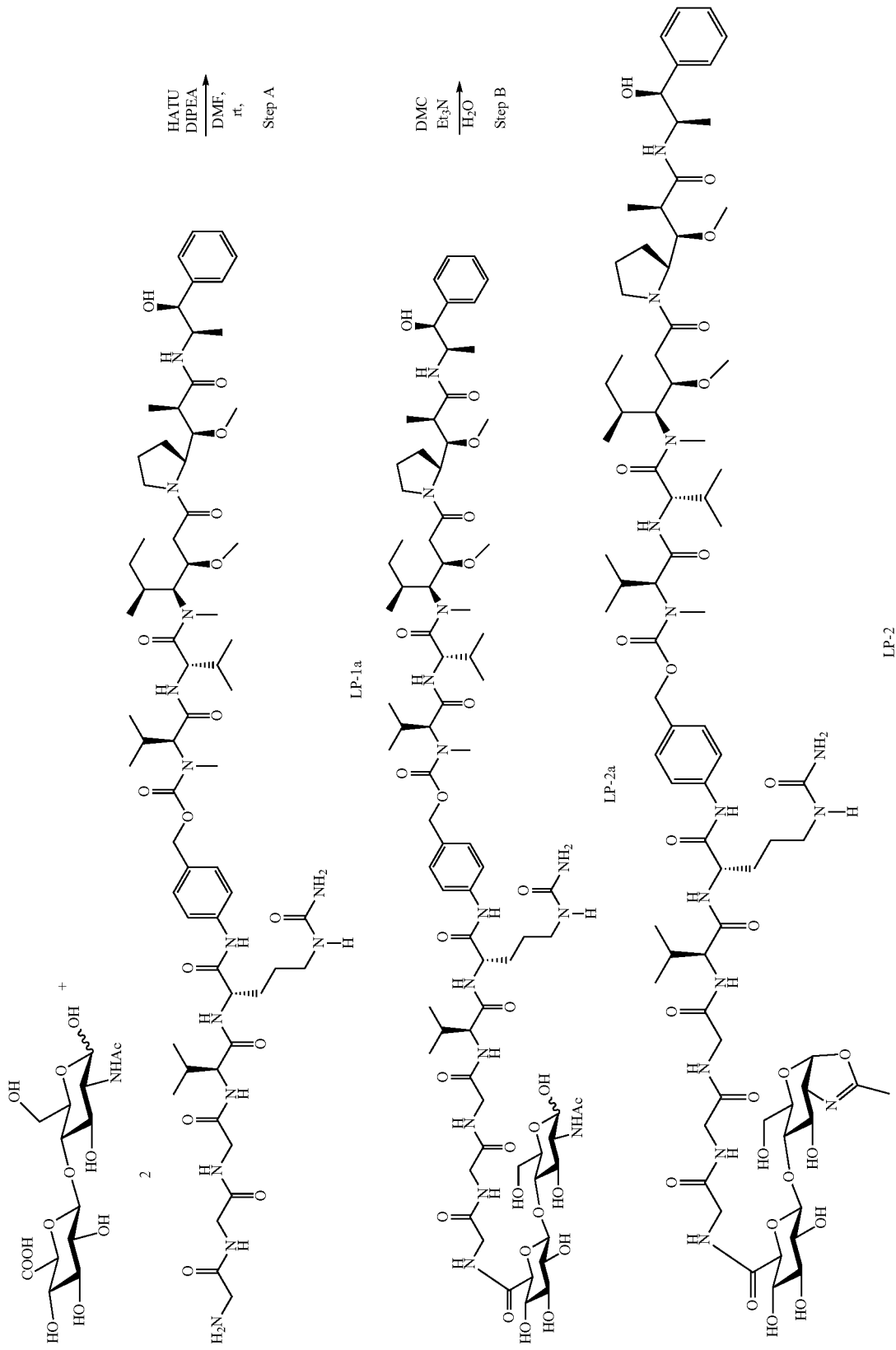

20.1 Step A: Preparation of Compound LP-2a

At rt, the compound 2 (0.5 to 5.0 equiv.), the compound LP-1a (1.0 equiv., GGG-VC-PAB-MMAE, CAS number: 2684216-48-4, commercially available), DMF, DIPEA (1 to 10 equiv.), and HATU (0.5 to 10 equiv.) were added successively into a 10 mL single-neck flask, and the resulting reaction solution was stirred at rt until the reaction was complete as monitored by HPLC. The reaction solution was purified by semi-preparative HPLC to afford compound LP-2a (white solid, yield 84%). MS (ESI) m/z of $C_{78}H_{126}N_{14}O_{26}{}^{2+}$ $[M+2H]^{2+}$: calc 837.4, found 837.8.

20.2 Step B: Preparation of Compound LP-2

At rt, the compound LP-2a (1 equiv.), $H_2O$, $Et_3N$ (1 to 100 equiv.) and DMC (2-chloro-1,3-dimethylimidazolidinium chloride, CAS: 37091-73-9, 1 to 100 equiv.) were added successively into a 10 mL single-neck flask. The resulting reaction solution was stirred at 0° C., and the reaction was monitored by HPLC until the reaction was complete. The reaction solution was purified by semi-preparative HPLC to afford compound LP-2 (yield 87%, white solid). MS (ESI) m/z of $C_{78}H_{124}N_{14}O_{25}{}^{2+}$ $[M+2H]^{2+}$: calc 828.4, found 828.7.

Example 8: Preparation of LP-3, LP-4 and LP-5

Linker-payloads LP-3, LP-4 and LP-5 with the following structures were prepared by employing steps similar to those of LP-2 preparation.

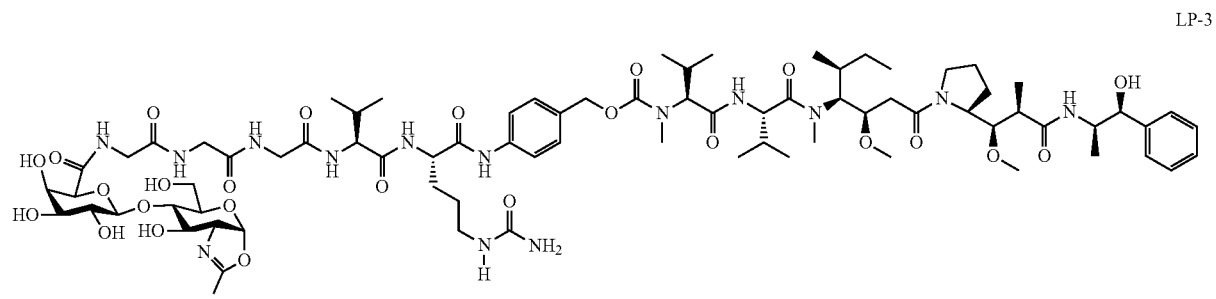

LP-3

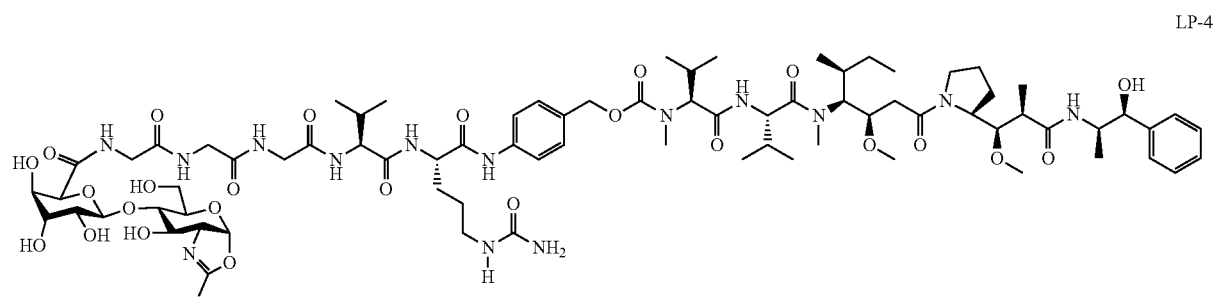

LP-4

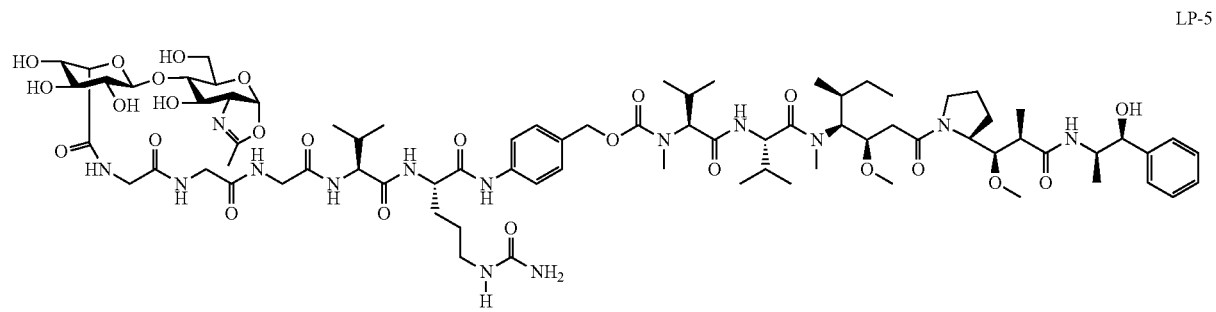

LP-5

Example 9: Preparation of LP-6
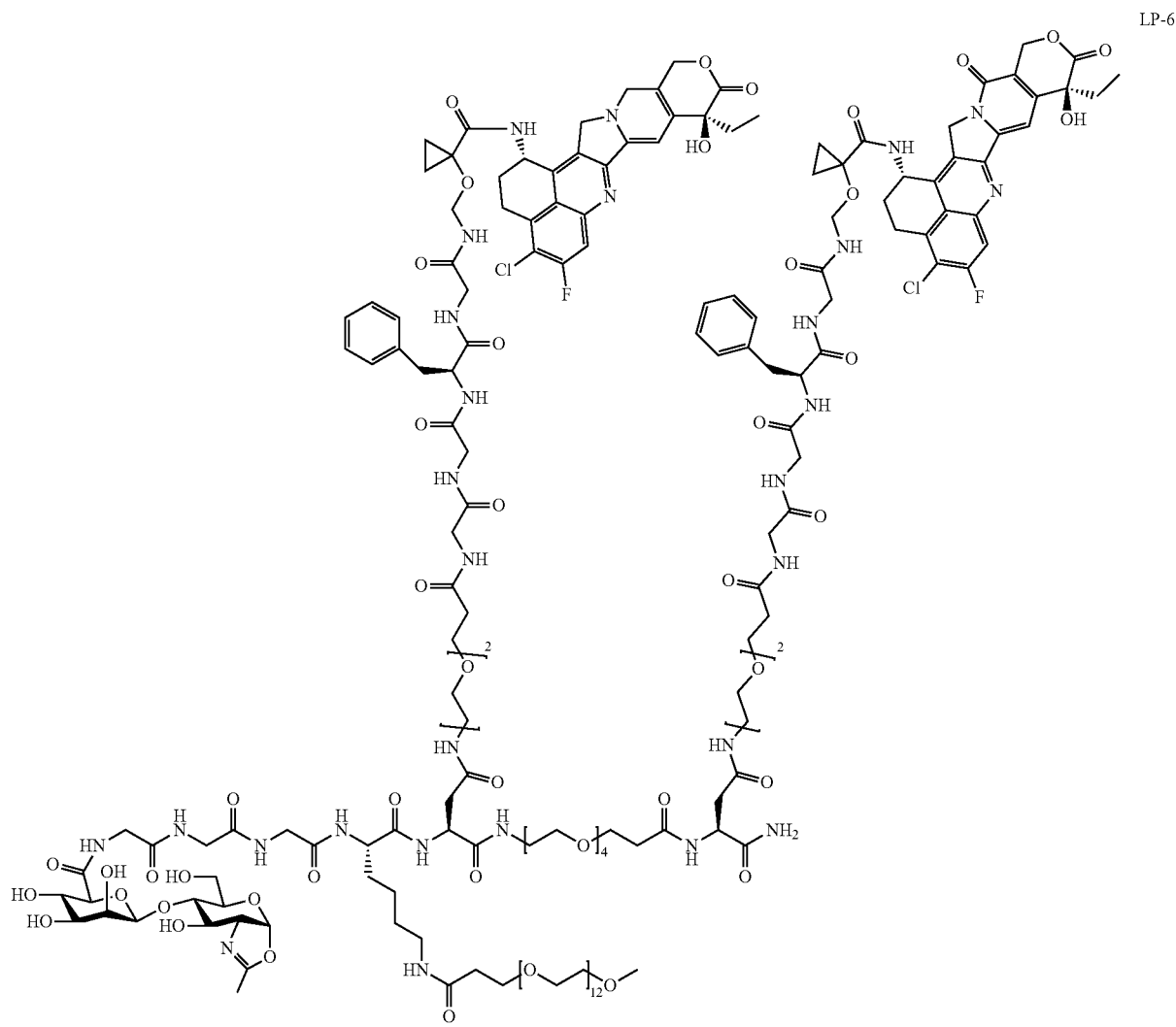
(1) Synthesis of LP-6-1
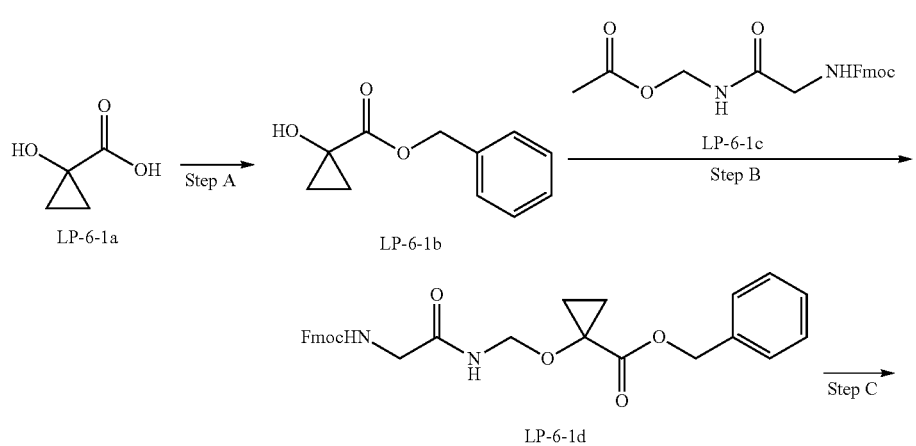

-continued

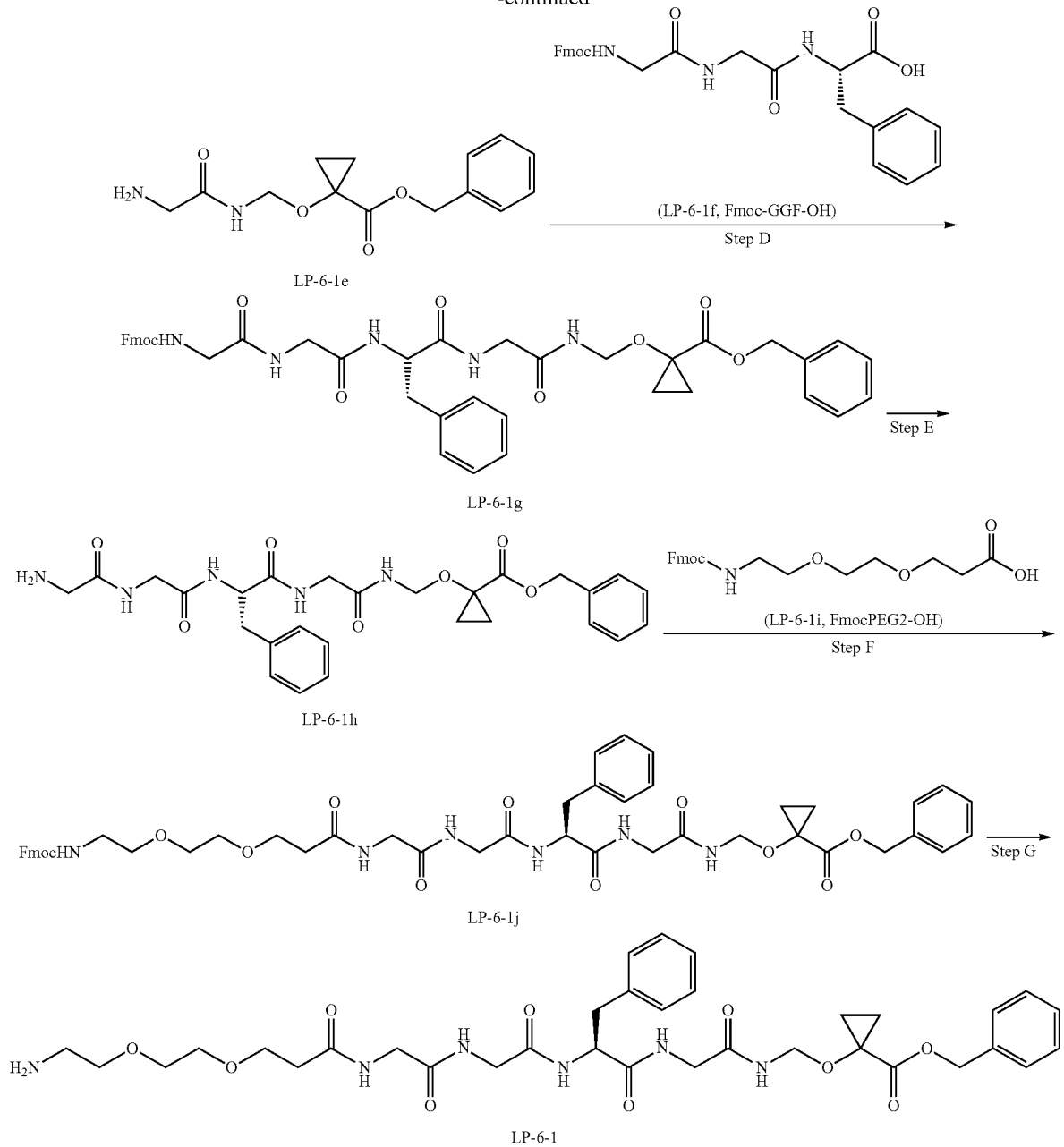

Step A: Synthesis of Intermediate LP-6-1b

Compound LP-6-1a (1.0 equiv.) and DMF (dissolution concentration: 1 g/mL) were added into a reaction flask, stirred for dissolution under the nitrogen atmosphere, and cooled to 0° C. to 5° C. Then DIEA (3 equiv.) was dropwise added. Subsequently, the resulting system was stirred at 5° C. for 10 min, and then benzyl bromide (1.3 equiv.) was dropwise added. After dropwise adding, the reaction system was allowed to naturally rise to rt and stirred for 16 h. The reaction solution was slowly poured into ice water, and methyl tert-butyl ether was added and stirred, followed by standing and liquid separation. An aqueous phase was extracted four times with methyl tert-butyl ether. Organic phases were merged, and washed with a saturated salt solution, dried over anhydrous sodium sulfate, filtered, and concentrated to afford a yellow oily crude product, and the yellow oily crude product was wet loaded, and purified by column chromatography on silica gel (eluent: PE/EA=6:1) to afford the product LP-6-1b (light yellow oil, quantitative yield).

Step B: Synthesis of Intermediate LP-6-1d

Under nitrogen protection, the intermediate LP-6-1b (2.0 equiv.), compound LP-6-1c (1.0 equiv.) and THF (dissolution concentration: 10 g/mL) were added into a reaction flask, and stirred for dissolution, TsOH (0.1 equiv.) was added to the reaction, and the system reacted at rt for 4 h. The reaction solution was slowly poured into ice water, and extracted with ethyl acetate three times. A merged organic phase was washed with a saturated sodium bicarbonate aqueous solution, water and a saturated salt solution, dried over anhydrous sodium sulfate, filtered and concentrated to afford a crude product, and the crude product was purified by column chromatography on silica gel (eluent: PE/EA=1:1) to afford product LP-6-1d (white solid, yield 40%).

Step C: Synthesis of Intermediate LP-6-1e

Under nitrogen protection, the compound LP-6-1d and N,N-dimethylacetamide (DMAc, dissolution concentration: 10 g/mL) were added into a reaction flask, and stirred for dissolution. The system was cooled to 14° C. to 18° C., DBU (0.5 equiv.) was dropwise added, and the reaction was performed at this temperature, until TLC showed that the reaction was complete (about 1.5 h) to afford intermediate LP-6-1e, and the intermediate was directly used for a next reaction without purification.

Step D: Synthesis of Intermediate LP-6-1g

The reaction solution in the previous step was cooled to 0° C. to 5° C., and pyridinium 4-toluenesulfonate (PPTS, 0.5 equiv.), 1-(3-dimethylaminopropyl)-3-ethylcarbodiimide (EDCI, 1.0 equiv.), 1-hydroxybenzotriazole (HOBT, 1.0 equiv.) and LP-6-1f (0.85 equiv.) were added successively. The reaction system reacted at 0° C. to 10° C. until LCMS showed that the reaction was complete (about 4 h). The reaction solution was added into ice water, and 2-methyl-tetrahydrofuran was added for extraction once. An aqueous phase was extracted twice with 2-methyltetrahydrofuran. Organic phases were merged, and washed successively with 0.5 M hydrochloric acid, a saturated NaHCO$_3$ aqueous solution, water and a saturated salt solution, dried over anhydrous sodium sulfate, filtered, concentrated, and purified by column chromatography on silica gel (eluent: DCM/MeOH) to afford product LP-6-1g (white solid, yield 78%).

Step E: Synthesis of Intermediate LP-6-1h

Under nitrogen protection, LP-6-1g and DMAc (dissolution concentration: 10 g/mL) were added into a reaction flask and stirred for dissolution. The temperature was lowered to 14° C. to 18° C.; DBU (0.5 equiv.) was dropwise added, and stirring and reaction were carried out at this temperature for 1.5 h. The extent of reaction was monitored by TLC. After the reaction, intermediate LP-6-1h was afforded, and was directly used for a next reaction without purification.

Step F: Synthesis of Intermediate LP-6-1j

The reaction solution of LP-6-1h in the previous step was cooled to 0° C. to 5° C., and PPTS (0.5 equiv.), EDCI (1 equiv.), HOBT (1 equiv.) and compound 3i (0.85 equiv.) were added, and reacted at 0° C. to 10° C. for 3 h to 4 h. The extent of reaction was monitored by LCMS. After the reaction was complete, the reaction solution was added into ice water, and 2-methyltetrahydrofuran was added for extraction once. An aqueous phase was extracted twice with 2-methyltetrahydrofuran. Organic phases were merged, and washed successively with 0.5 M hydrochloric acid, a saturated NaHCO$_3$ aqueous solution, water and a saturated salt solution, dried over anhydrous sodium sulfate, filtered, concentrated, dry-blended, and purified by column chromatography (eluent: DCM/MeOH) to afford LP-6-1j (white solid, yield 50%).

Step G: synthesis of compound LP-6-1

Under nitrogen protection, the intermediate LP-6-1j was dissolved in DCM (concentration: 15 g/mL), and DBU (0.5 equiv.) was dropwise added at 20° C. The temperature was maintained, and stirring and reaction were carried out until HPLC showed the reaction was complete. Subsequently, DCM was added into the system to dilute the reaction solution, directly wet loaded and purified by column chromatography (eluent: DCM/MeOH) to afford compound LP-6-1 (white solid, yield 82%). MS (ESI) m/z of $C_{34}H_{47}N_6O_{10}^+$ [M+H]$^+$: calc 699.4, found 699.6.

(2) Synthesis of LP-6-2

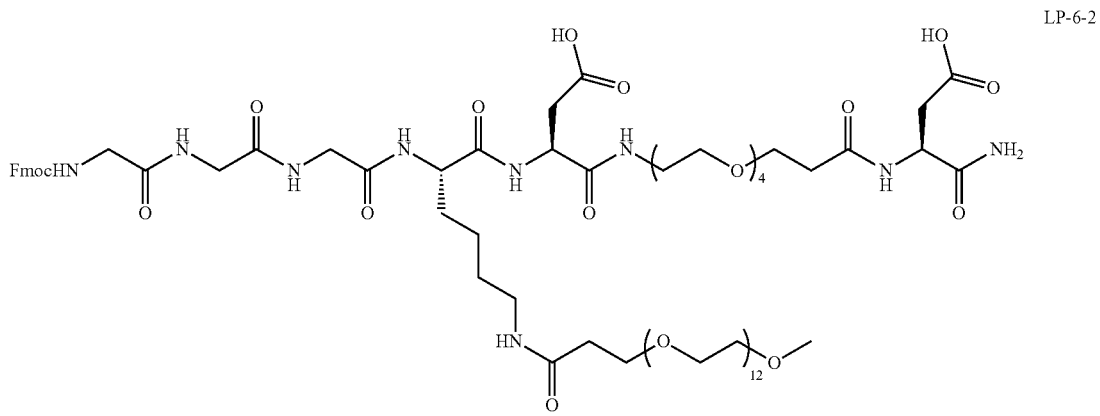

LP-6-2

LP-6-2 was synthesized by employing a peptide solid-phase synthesis, and the steps were shown as follows.

Step 1: Preparation of NH2-Asp(OtBu)-Rink Amide Resin 400 g of Rink amide resin was weighed and placed into a reactor, and soaked in 2400 mL of DCM for 0.5 h to allow the resin to fully swell, followed by draining. 2400 mL of decapping reagent was added, and washing was carried out, followed by draining. 2400 mL of decapping reagent was added, nitrogen was blown, and stirring and reaction were carried out at 25±1° C. for 0.5 h, followed by draining. Washing was performed twice successively with 2400 mL of DMF, 2400 mL of absolute ethanol, 2400 mL of DCM, and 2400 mL of DMF, followed by draining. Kaiser test showed blue.

88.87 g of Fmoc-Asp(OtBu)-OH and 29.19 g of HOBT were weighed and dissolved in 2000 mL of DMF solution and 80 nal of DIC, the mixture was placed in an ice bath at −10° C. for 0.5 h, and then slowly added into a reactor for reaction, at rt, nitrogen was blown, and stirring and reaction were carried out for 2 h, followed by draining. Washing was performed twice successively with 2400 mL of DMF, 2400 mL of absolute ethanol, 2400 mL of DCM, and 2400 mL of DMF, followed by draining. Kaiser test showed light blue. 2400 mL of DCM was added, and then 60 ml of capping reagent was added, nitrogen was blown, and stirring and reaction were carried out at 25±1° C. for 1 h, followed by draining. Washing was performed twice successively with 2400 mL of DMF, 2400 mL of absolute ethanol, 2400 mL of DCM, and 2400 mL of DMF, followed by draining. Kaiser test showed colorlessness.

2400 mL of decapping reagent was added, and washing was carried out, followed by draining. 2400 mL of decapping reagent was added, nitrogen was blown, and stirring and reaction were carried out at 25±1° C. for 0.5 h, followed by draining Washing was performed twice successively with 2400 mL of DMF, 2400 mL of absolute ethanol, 2400 mL of DCM, and 2400 mL of DMF, followed by draining. Kaiser test showed blue.

Step 2: Preparation of NH2-PEG4-Asp(OtBu)-Rink Amide Resin 131.64 g of Fmoc-PEG4-OH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction, at rt, nitrogen was blown, and stirring and reaction were carried out for 2 to 4 h, followed by draining. Washing was performed twice successively with 2400 mL of DMF, 2400 mL of absolute ethanol, 2400 mL of DCM, and 2400 mL of DMF, followed by draining. Kaiser test showed colorlessness.

2400 mL of decapping reagent was added, and washing was carried out, followed by draining. 2400 mL of decapping reagent was then added, nitrogen was blown, and stirring and reaction were carried out at 25±1° C. for 0.5 h, followed by draining Washing was performed twice successively with 2400 mL of DMF, 2400 mL of absolute ethanol, 2400 mL of DCM, and 2400 mL of DMF, followed by draining. Kaiser test showed blue.

Step 3: Preparation of NH2-Asp(OtBu)-PEG4-Asp(OtBu)-Rink Amide Resin 222.18 g of Fmoc-Asp(OtBu)-OH and 72.96 g of HOBT were weighed and dissolved in 2000 mL of DMF solution and 80 ml of DIC, and the mixture was placed in an ice bath at −10° C. for 0.5 h, and then slowly added into a reactor for reaction, at rt, nitrogen was blown, and stirring and reaction were carried out for 2 to 4 h, followed by draining. Washing was performed twice successively with 2400 mL of DMF, 2400 mL of absolute ethanol, 2400 mL of DCM, and 2400 mL of DMF, followed by draining. Kaiser test showed colorlessness.

2400 of decapping reagent was added, and washing was carried out, followed by draining. 2400 mL of decapping reagent was then added, nitrogen was blown, and stirring and reaction were carried out at 25±1° C. for 0.5 h, followed by draining Washing was performed twice successively with 2400 mL of DMF, 2400 mL of absolute ethanol, 2400 mL of DCM, and 2400 mL of DMF, followed by draining. Kaiser test showed blue.

Step 4: Preparation of Dde-Lys(NH2)-Asp(OtBu)-PEG4-Asp(OtBu)-Rink Amide Resin 191.75 g of Dde-Lys(Fmoc)-OH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction, at rt, nitrogen was blown, and stirring and reaction were carried out for 2 to 4 h, followed by draining. Washing was performed twice successively with 2400 mL of DMF, 2400 mL of absolute ethanol, 2400 mL of DCM, and 2400 mL of DMF, followed by draining. Kaiser test showed colorlessness.

2400±100 mL of decapping reagent was added, and washing was carried out, followed by draining. 2400 mL of decapping reagent was then added, nitrogen was blown, and stirring and reaction were carried out at 25±1° C. for 0.5 h, followed by draining Washing was performed twice successively with 2400 mL of DMF, 2400 mL of absolute ethanol, 2400 mL of DCM, and 2400 mL of DMF, followed by draining. Kaiser test showed blue.

Step 5: Preparation of Dde-Lys(mPEG12)-Asp(OtBu)-PEG4-Asp(OtBu)-Rink Amide Resin 170.84 g of m-PEG12-CH2CH2COOH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction, at rt, nitrogen was blown, and stirring and reaction were carried out for 2 to 4 h, followed by draining. Washing was performed twice successively with 2400 mL of DMF, 2400 mL of absolute ethanol, 2400 mL of DCM, and 2400 mL of DMF, followed by draining. Kaiser test showed colorlessness.

Step 6: Preparation of NH2-Lys(PEG12)-Asp(OtBu)-PEG4-Asp(OtBu)-Rink Amide Resin 2400 mL of de-dde reagent was added, nitrogen was blown, and stirring and reaction were carried out at 25±1° C. for 10 min, followed by draining. After this operation was repeated three times, washing was performed twice successively with 2400 mL of DMF, 2400 mL of absolute ethanol, 2400 mL of DCM, and 2400 mL of DMF, followed by draining. Kaiser test showed blue.

Step 7: Preparation of Fmoc-Gly-Gly-Gly-Lys(PEG12)-Asp(OtBu)-PEG4-Asp(OtBu)-Rink Amide Resin 111.08 g of Fmoc-Gly-Gly-Gly-OH and 48.64 g of HOBT were weighed and dissolved in 2000 mL of DMF solution and 80.0 ml of DIC, and the mixture was placed in an ice bath at −10° C. for 0.5 h, and then slowly added into a reactor for reaction, at rt, nitrogen was blown, and stirring and reaction were carried out for 2 to 4 h, followed by draining. Washing was performed twice successively with 2400 mL of DMF, 2400 mL of absolute ethanol, 2400 mL of DCM, and 2400 mL of DMF, followed by draining. Kaiser test showed colorlessness. Resin peptide was washed three times with 2400 mL of absolute ethanol, drained, and left to cut.

Step 8: Preparation of LP-6-2

10000 mL of cleavage reagent (TFA:TIS:H2O=95:2.5:2.5) was added into a 10 L reactor and cooled to −10±2° C., and the dried weighed resin was added thereinto, followed by heating, at 20±5° C., nitrogen was introduced and stirring was carried out for 2 h. Filtration was performed, the resin was washed once with 100 mL of TFA, and the filtrate and the washing solution were merged.

40 L of pre-cooled (below −10° C.) cold ether was added, and stirred for 10 min, and then centrifugal precipitation was carried out. Then the supernatant was discarded. Precipitates were mixed and shaken up with the cold ether. Then centrifugal precipitation was carried out again (this step was repeated three times, with the dosage of 10 L, 10 L, and 10 L each time. The revolution speed was set to be 3600 rpm for each centrifugation, the centrifugation time was 5 minutes, and the temperature of the inner chamber of a centrifuge was −5° C.).

The precipitates were collected to afford an LP-6-2 crude product, and the crude product was purified by Prep-HPLC and freeze-dried to afford LP-6-2. MS (ESI) m/z of $C_{74}H_{121}N_9O_{31}{}^{2+}$ $[M+2H]^{2+}$: calc 815.9, found 816.3.

(3) Synthesis of LP-6-3
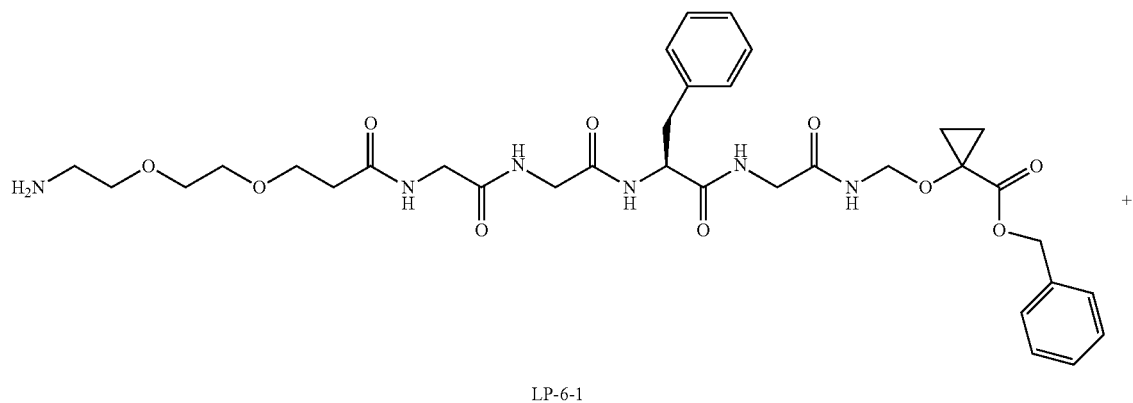
LP-6-1
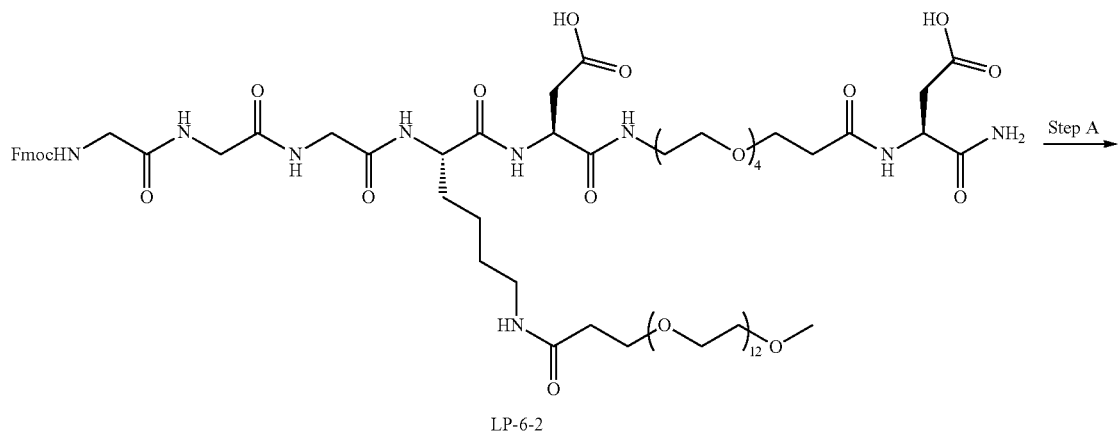
LP-6-2

-continued
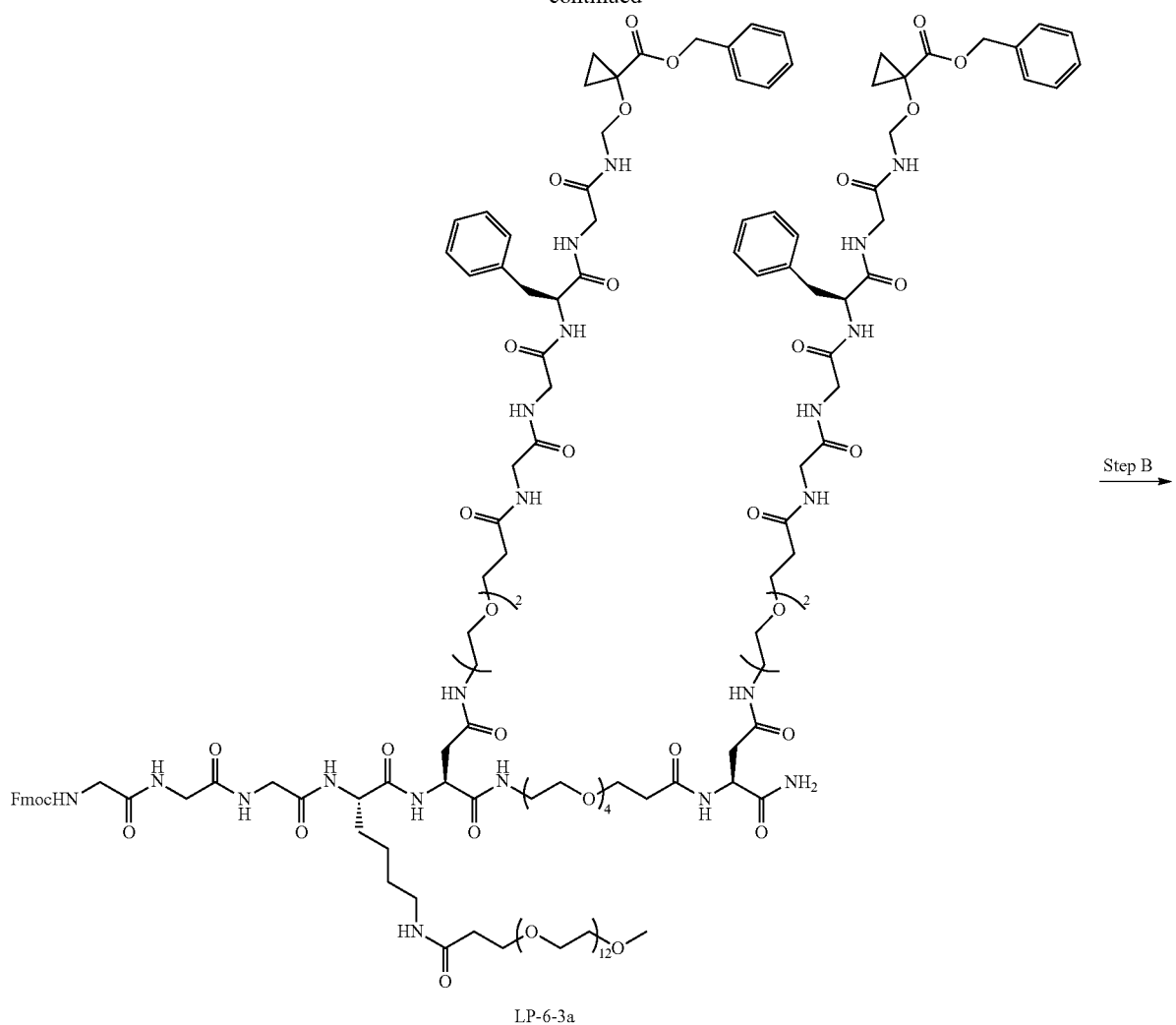
LP-6-3a
Step B

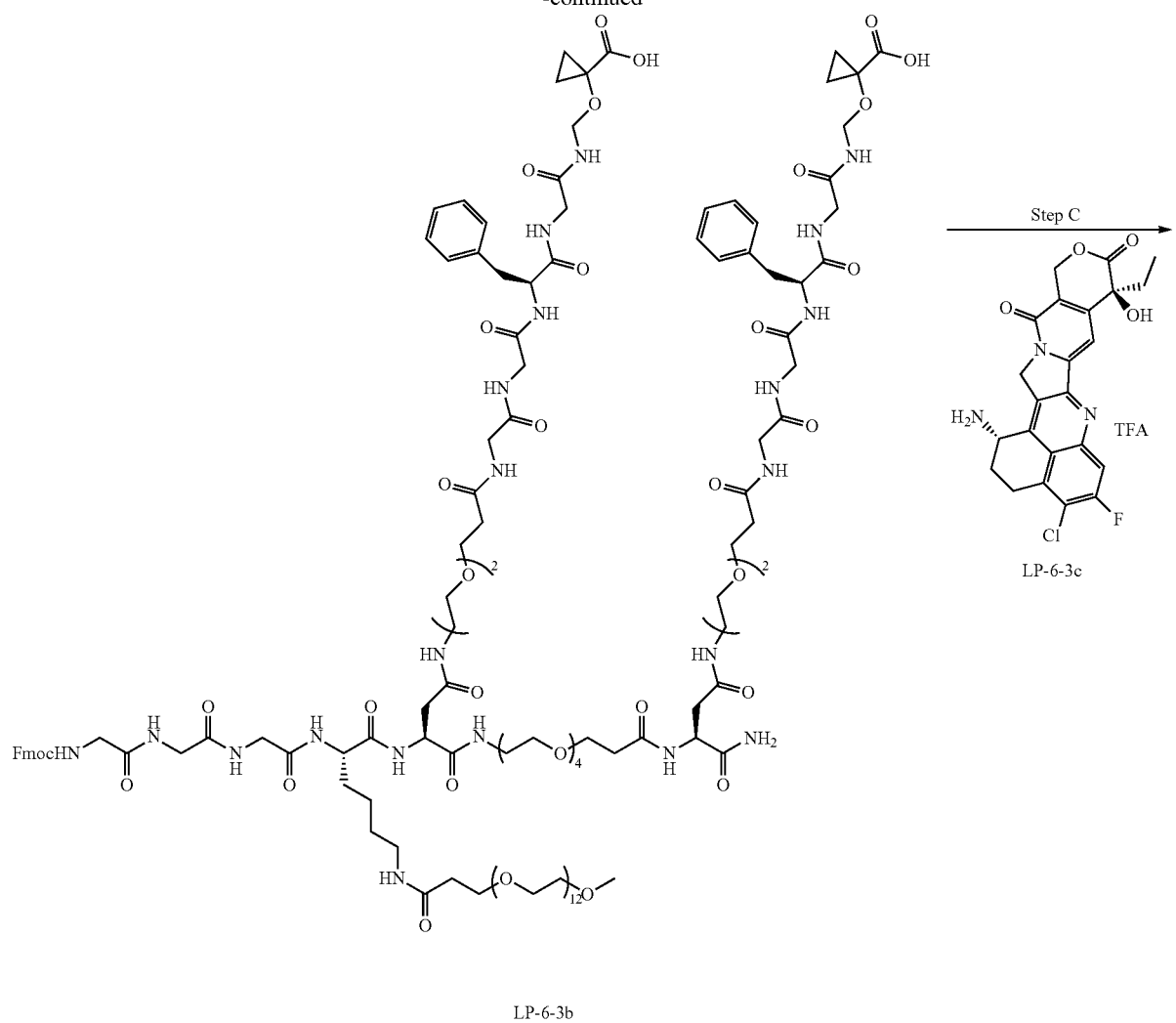
LP-6-3b
Step C →
LP-6-3c

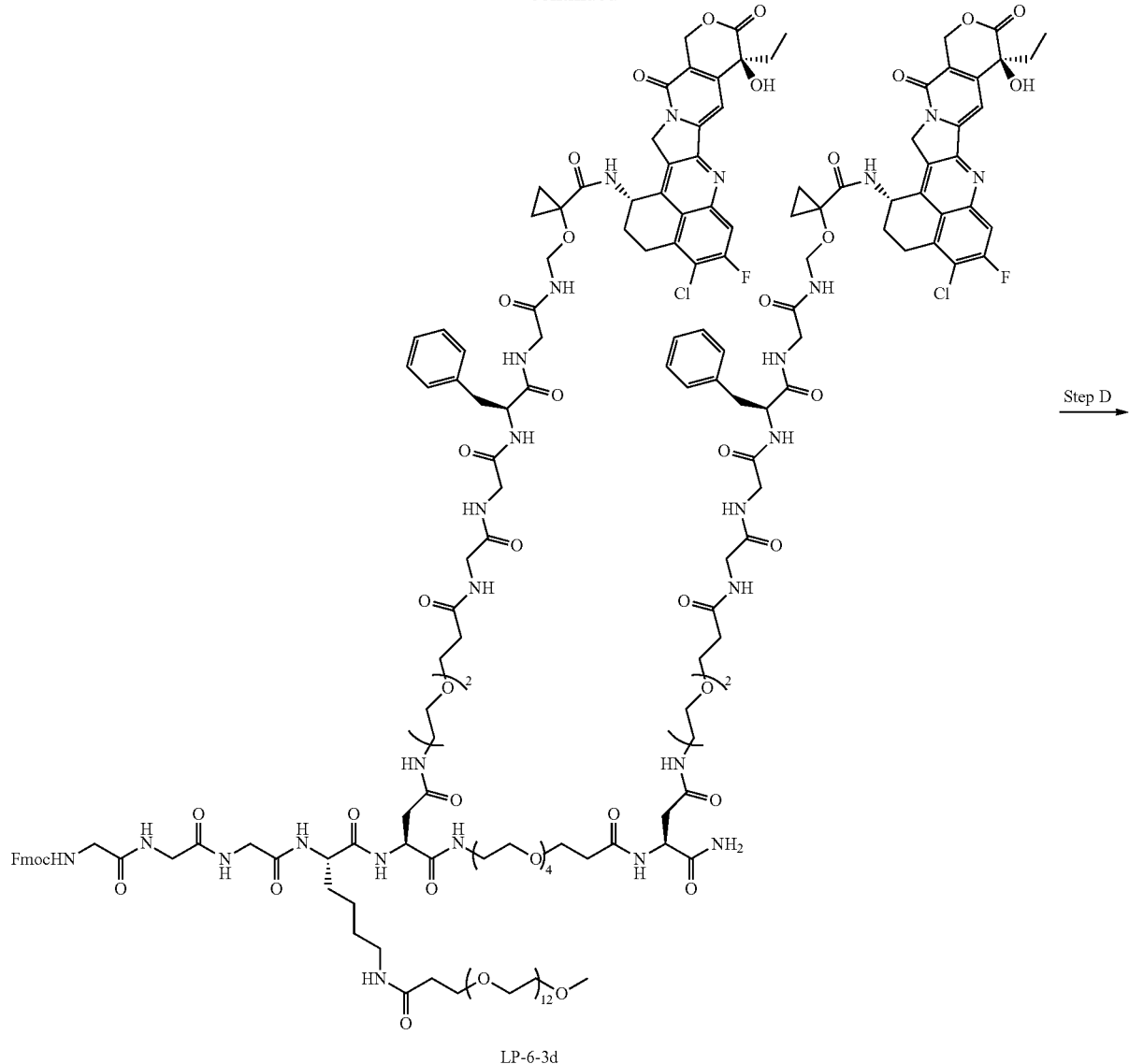
-continued
LP-6-3d

-continued

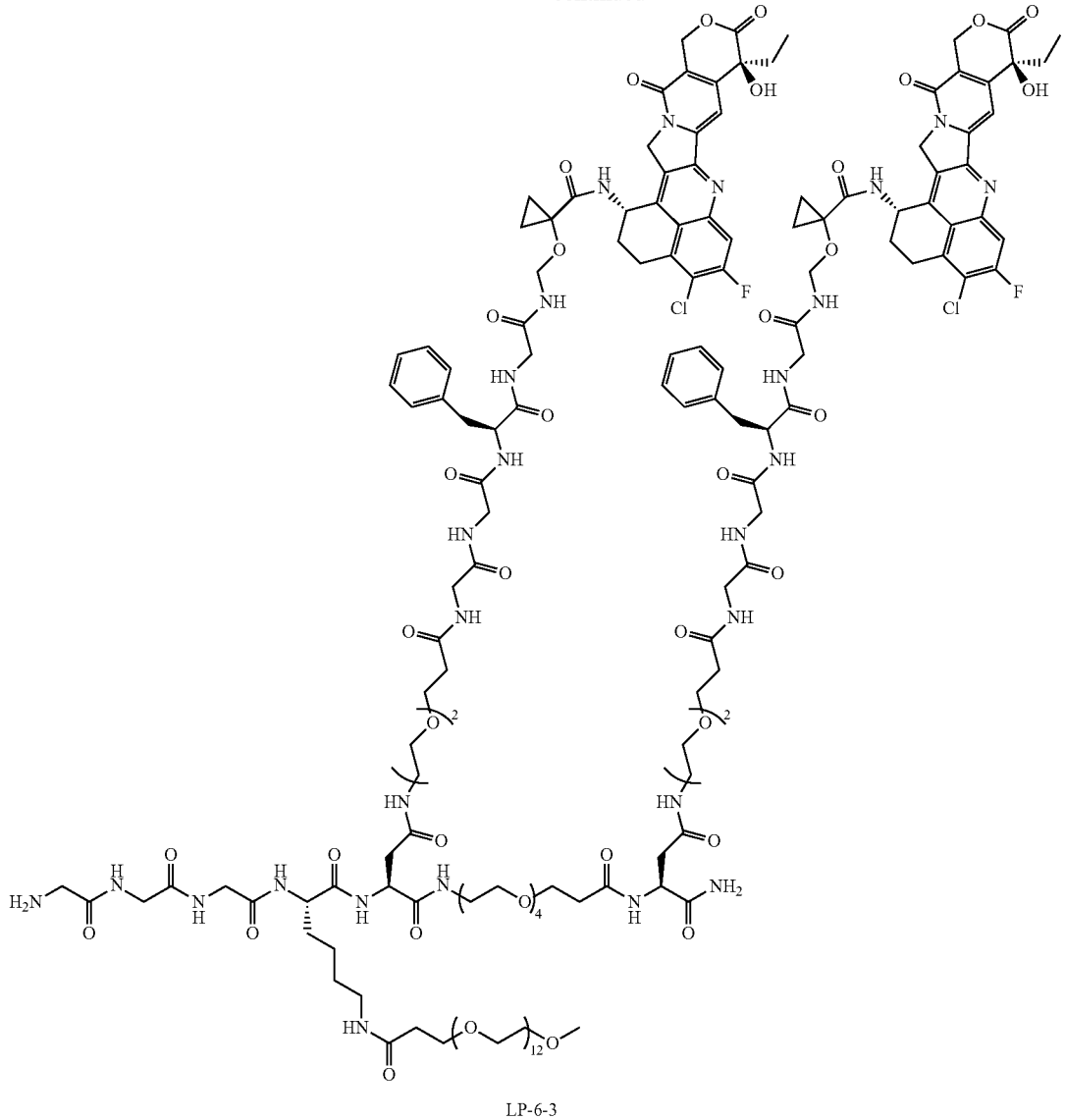

LP-6-3

Step A: synthesis of intermediate LP-6-3a

Compound LP-6-1 (2.2 equiv.) and the compound LP-6-2 (1.0 equiv.) were added into a reaction flask and dissolved in DMF. Subsequently, DIPEA (5.0 eq.) was added and well stirred, and then, HATU (2.5 equiv.) was added into the system for reaction at rt. Monitoring was performed by HPLC until the reaction was complete (about 2 h). The reaction mixture was directly purified by prep-HPLCA preparation solution was freeze-dried to afford compound LP-6-3a (white solid, yield 52%). MS (ESI) m/z of $C_{143}H_{212}O_{48}N_{21}{}^{3+}$ [M+3H]$^{3+}$: calc 997.2, found 875.9 (some functional groups would shed after ionization).

Step B: Synthesis of Intermediate LP-6-3b

The compound LP-6-3a was dissolved in purified water, and a certain amount of palladium hydroxide (10 wt % Pd(OH)$_2$ on carbon) was added. The system was replaced with hydrogen three times and then stirred at rt for 1.5 h, during which, the extent of reaction was monitored, and the reaction was immediately stopped after the disappearance of raw materials to prevent the increase of de-Fmoc products. The reaction solution was filtered, and preparation was performed by pre-HPLC to afford compound LP-6-3b (white solid, yield 76%). MS (ESI) m/z of $C_{128}H_{200}O_{48}N_{21}{}^{3+}$ [M+3H]$^{3+}$: calc 937.1, found 875.9 (some functional groups would shed after ionization).

Step C: Synthesis of Intermediate LP-6-3d

Compound LP-6-3b (1.0 equiv.) and compound LP-6-3c (2.2 equiv.) were weighed and dissolved in DMF. DIPEA (5.0 equiv.) was added and well stirred. Subsequently, HATU (2.5 equiv.) was added for reaction at rt. Monitoring was performed by HPLC until the reaction was complete (about 16 h). The reaction system was directly purified by prep-HPLC. A preparation solution was freeze-dried to afford compound LP-6-3d (yellow solid, yield 66%). MS (ESI) m/z of $C_{174}H_{232}O_{55}Cl_2F_2N_{27}{}^{3+}$ [M+3H]$^{3+}$: calc 1229.2, found 1229.3.

Step D: Synthesis of Compound LP-6-3

Compound LP-6-3d was dissolved in DMF, and diethylamine was added for reaction at rt. Monitoring was performed by HPLC until the reaction was complete (about 0.5 h). After the reaction, the pH was regulated to neutral, then preparation was performed by pre-HPLC, and freeze drying was performed to afford compound LP-6-3 (yellow solid, yield 73%). MS (ESI) m/z of $C_{159}H_{222}O_{53}Cl_2F_2N_{27}^{3+}$ [M+3H]$^{3+}$: calc 1155.2, found 1155.3.
For the synthesis of compound LP-6-3c, please refer to patent CN202211428194.6.
(4) Synthesis of LP-6
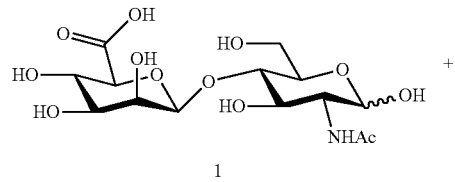
1
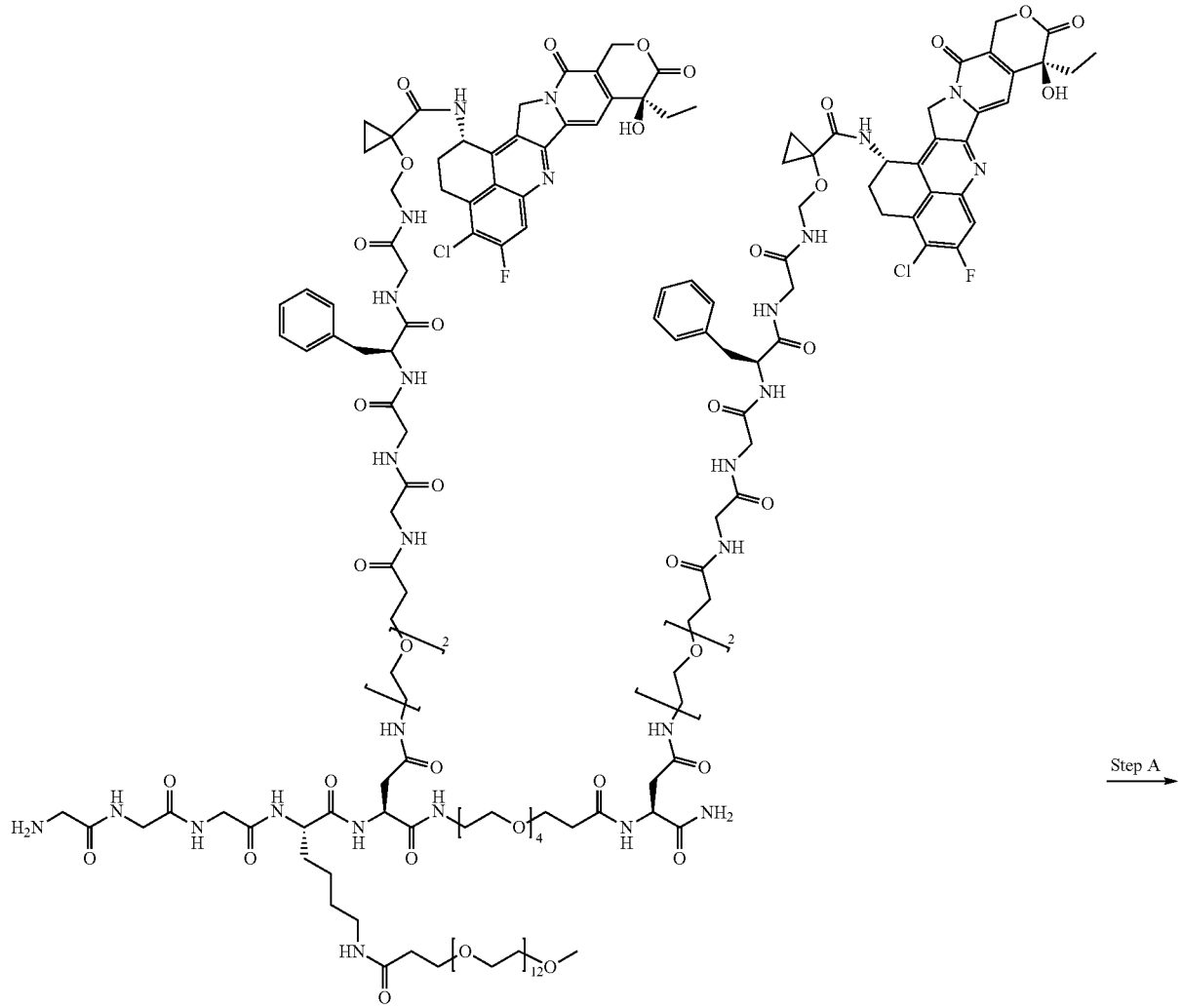
LP-6-3
Step A -continued
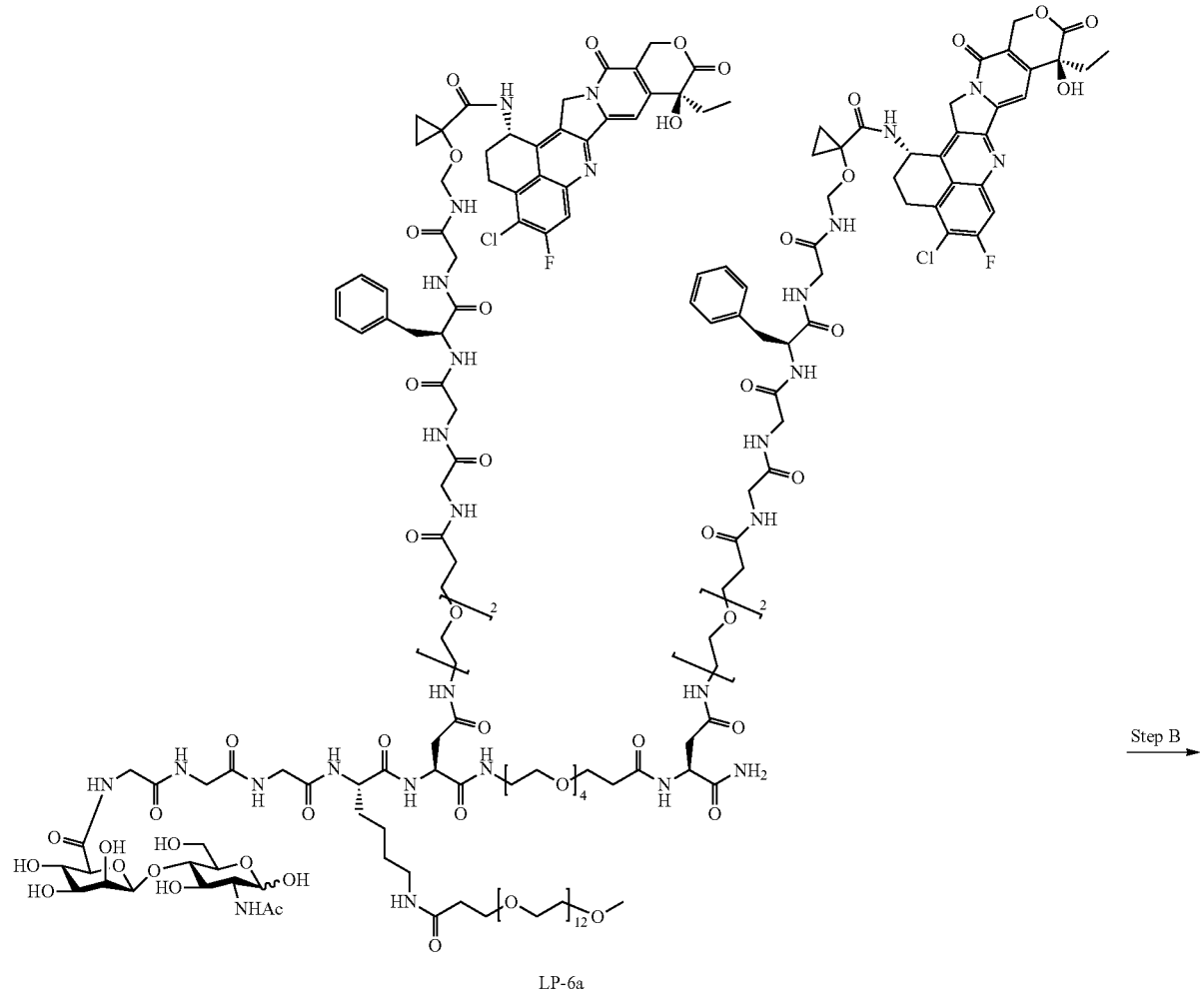
LP-6a
Step B

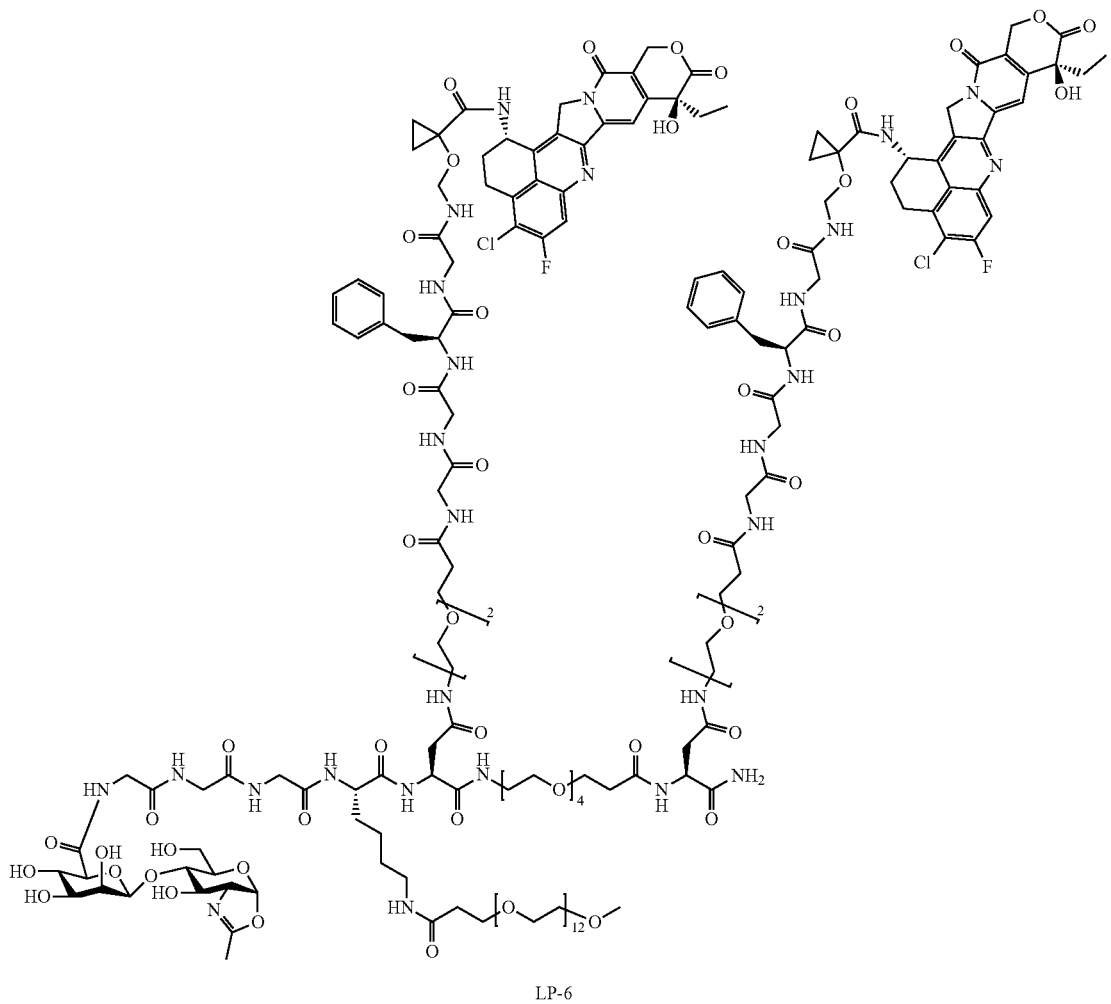

LP-6

Synthesis of LP-6a

The compound 1 (0.5 to 5.0 equiv.) and the compound LP-6-3 (1.0 equiv.) were dissolved in DMF. DIPEA (1 to 10 equiv.) was added and well stirred at 0° C. HATU (0.5 to 10 equiv.) was added. The resulting reaction system was stirred at 0° C. The extent of reaction was monitored by HPLC until the reaction was complete (about 2 h). The reaction system was prepared directly by prep-HPLC, and the preparation solution was freeze-dried to afford compound LP-6a (yellow solid, yield 63%). MS (ESI) m/z of $C_{173}H_{243}O_{64}Cl_2F_2N_{28}^{3+}$ [M+3H]$^{3+}$: calc 1281.5, found 1281.8.

Synthesis of LP-6

Compound LP-6a was weighed and dissolved in purified water. After the compound was stirred in an ice water bath and cooled, Et$_3$N (1 to 100 equiv.) and DMC (2-chloro-1,3-dimethylimidazolidinium chloride, CAS: 37091-73-9, 1 to 100 equiv.) were added. The extent of reaction was monitored by HPLC. After the reaction was complete, purification was performed by prep-HPLC, and the preparation solution was freeze-dried to afford compound LP-6 (light yellow solid, yield 74%). MS (ESI) m/z of $C_{173}H_{241}O_{63}Cl_2F_2N_{28}^{3+}$ [M+3H]$^{3+}$: calc 1275.5, found 1275.9.

Example 9: Preparation of LP-7
The structure of LP-7 was as follows:
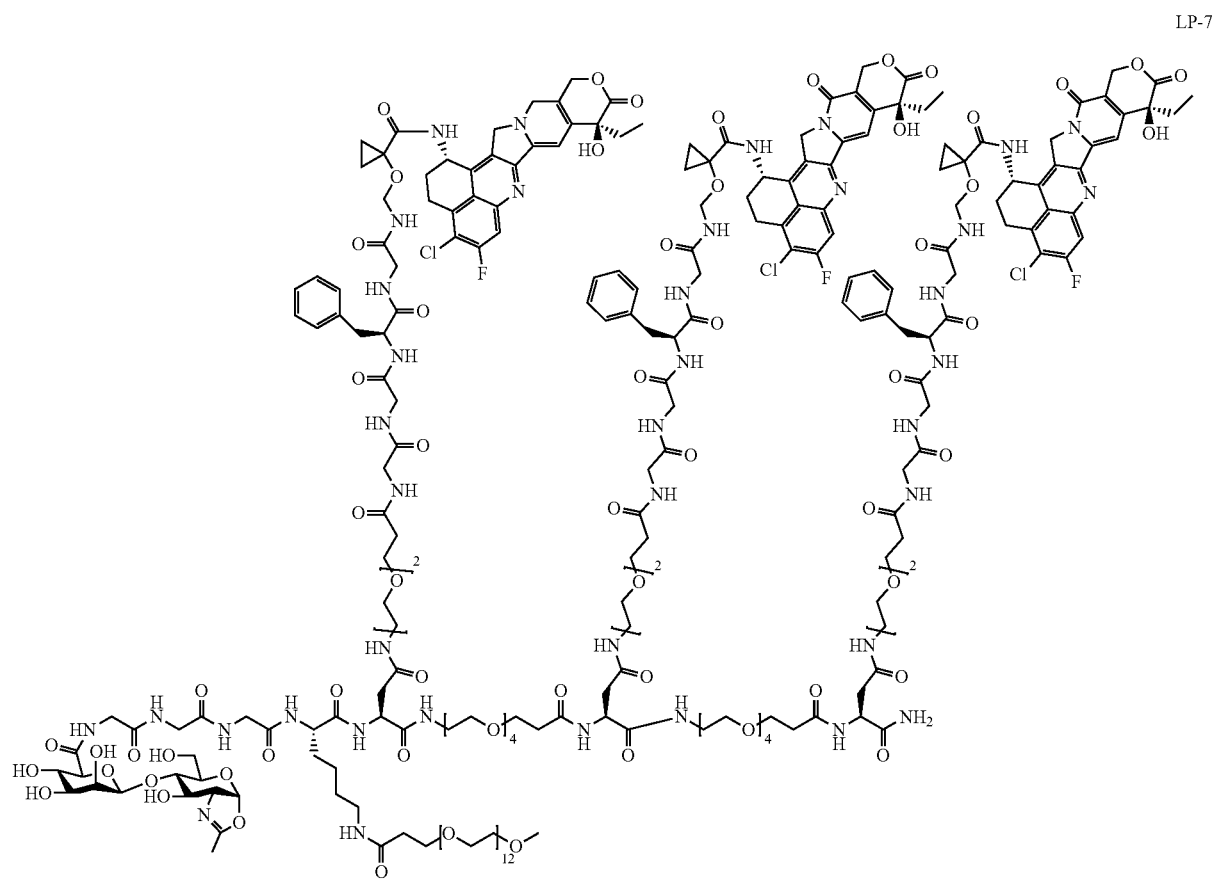
The synthesis route was as follows:

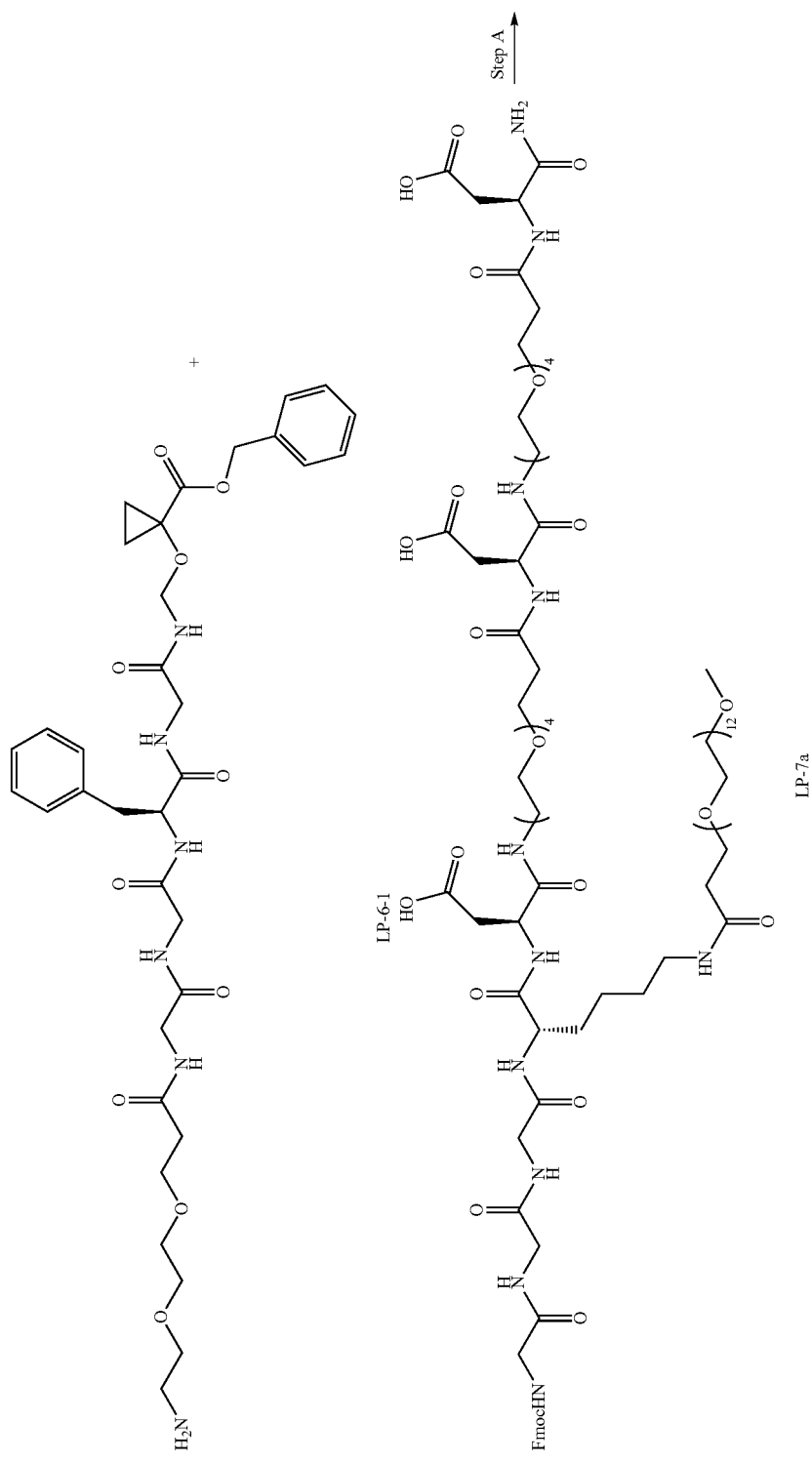

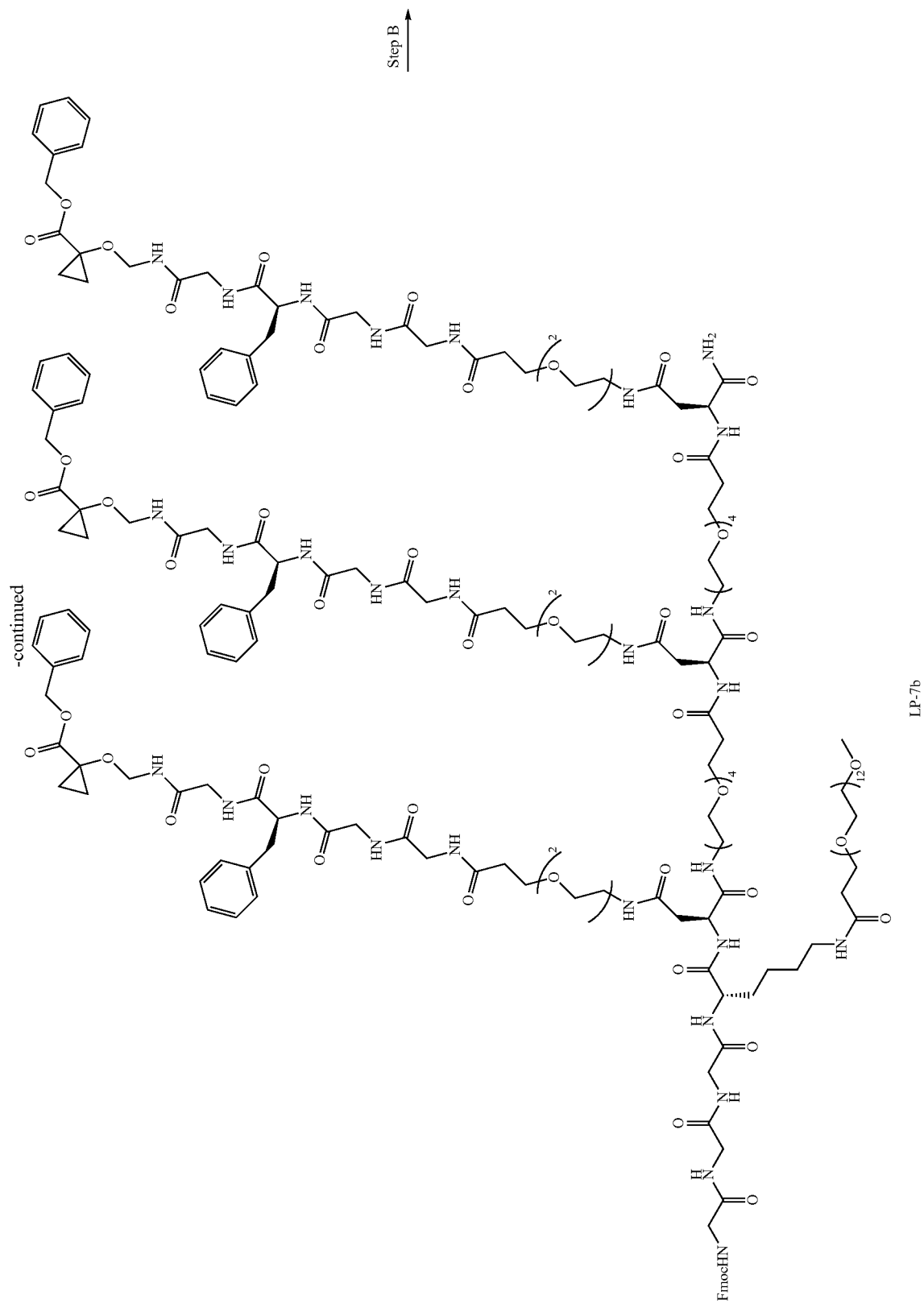

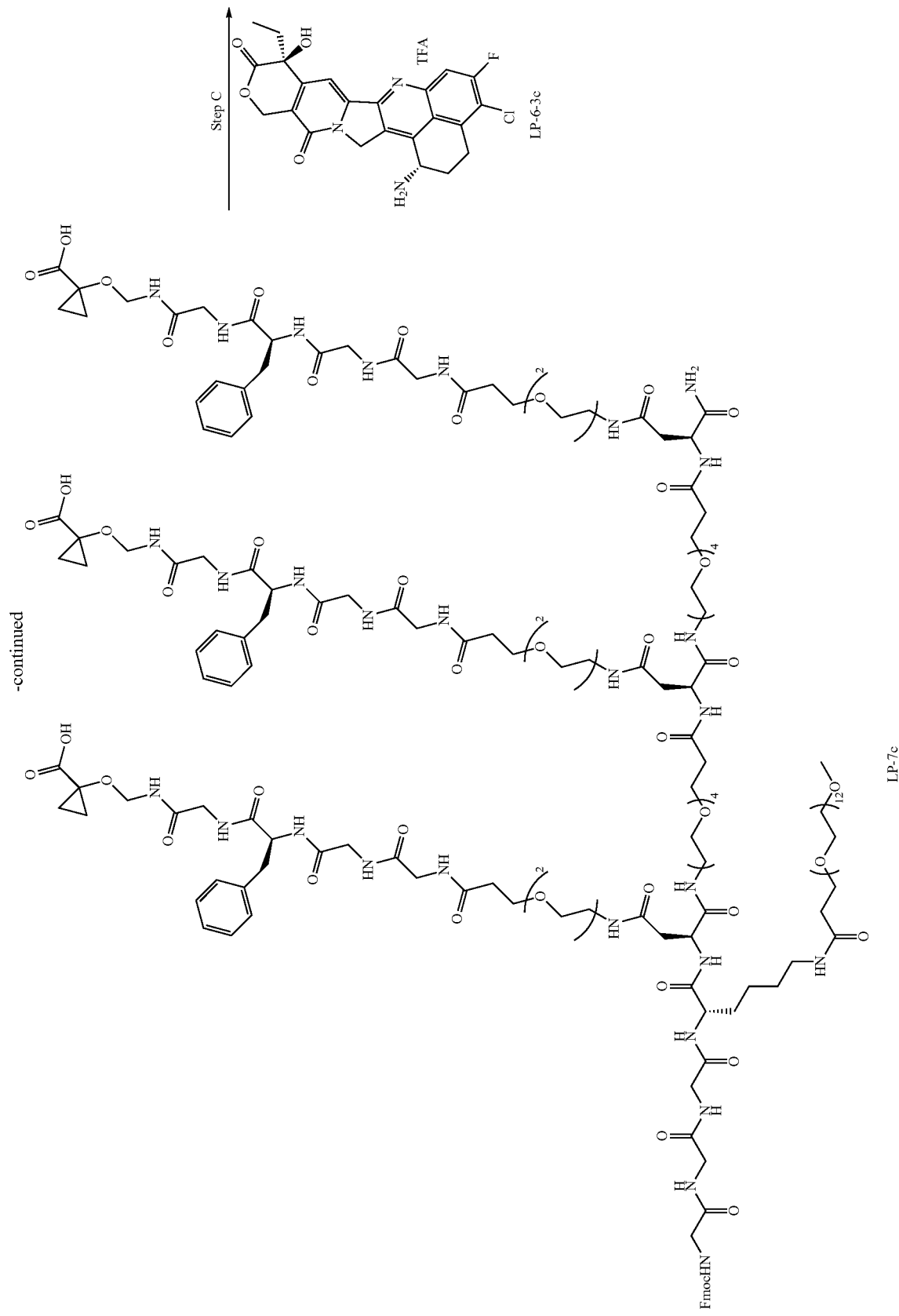

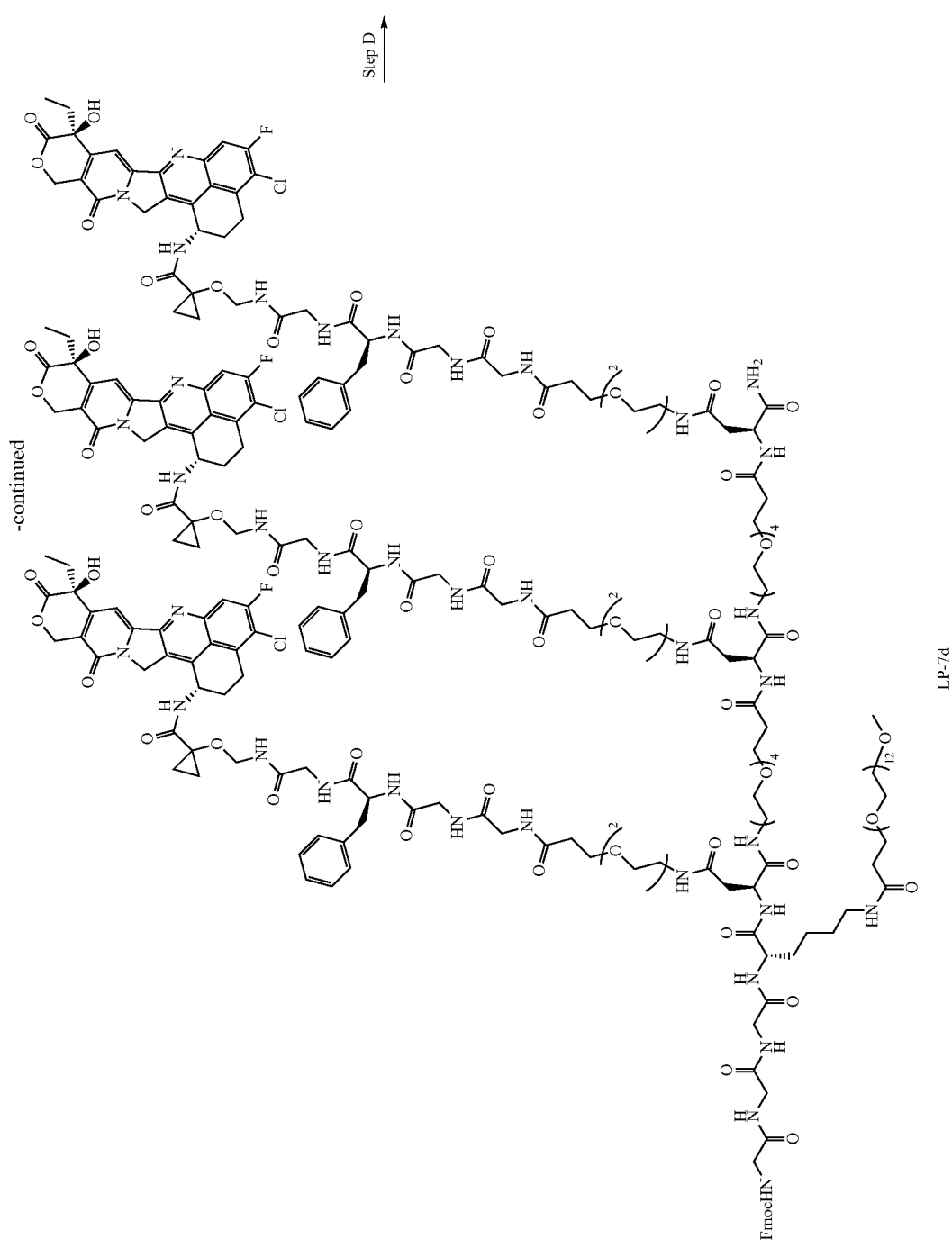

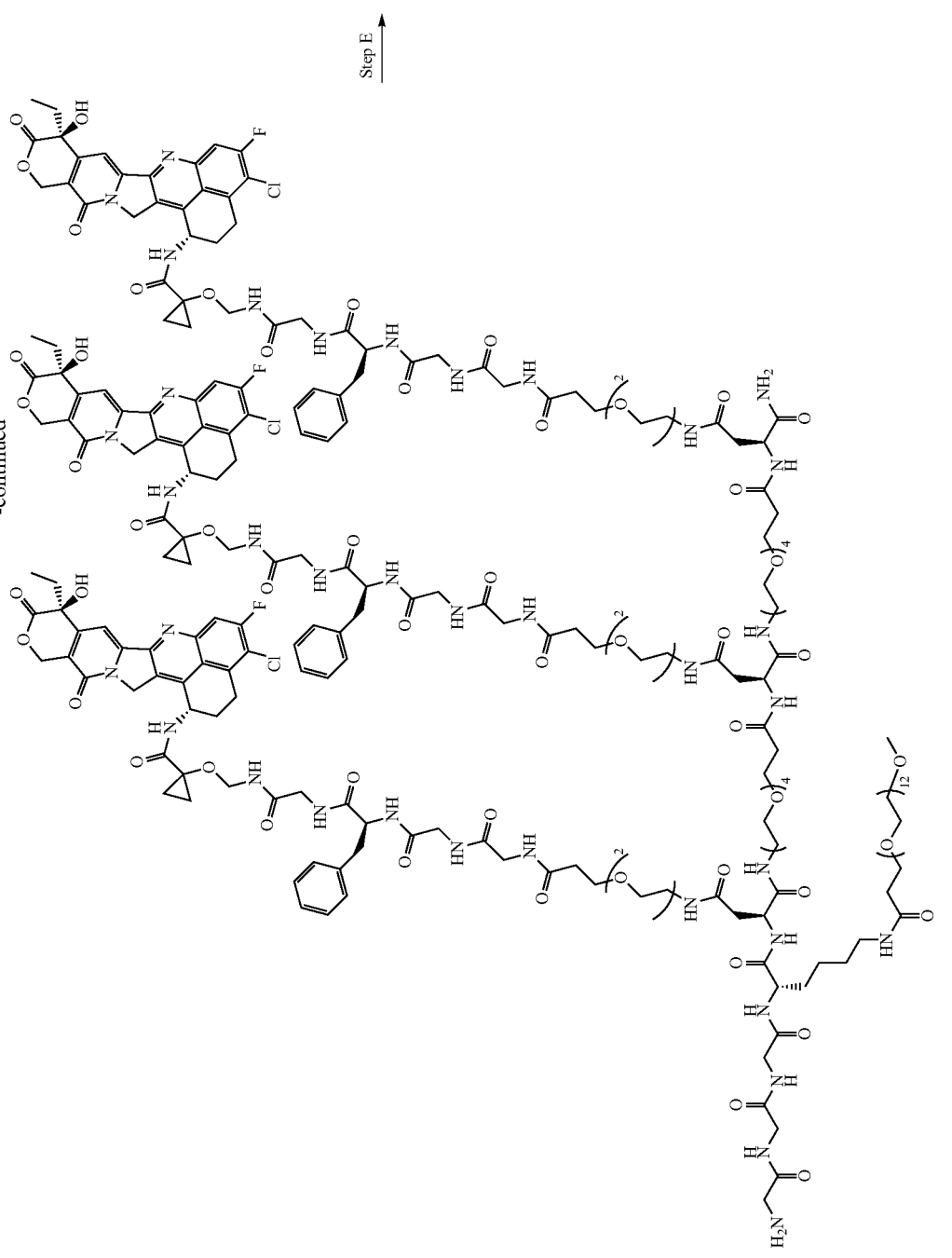
LP-7e

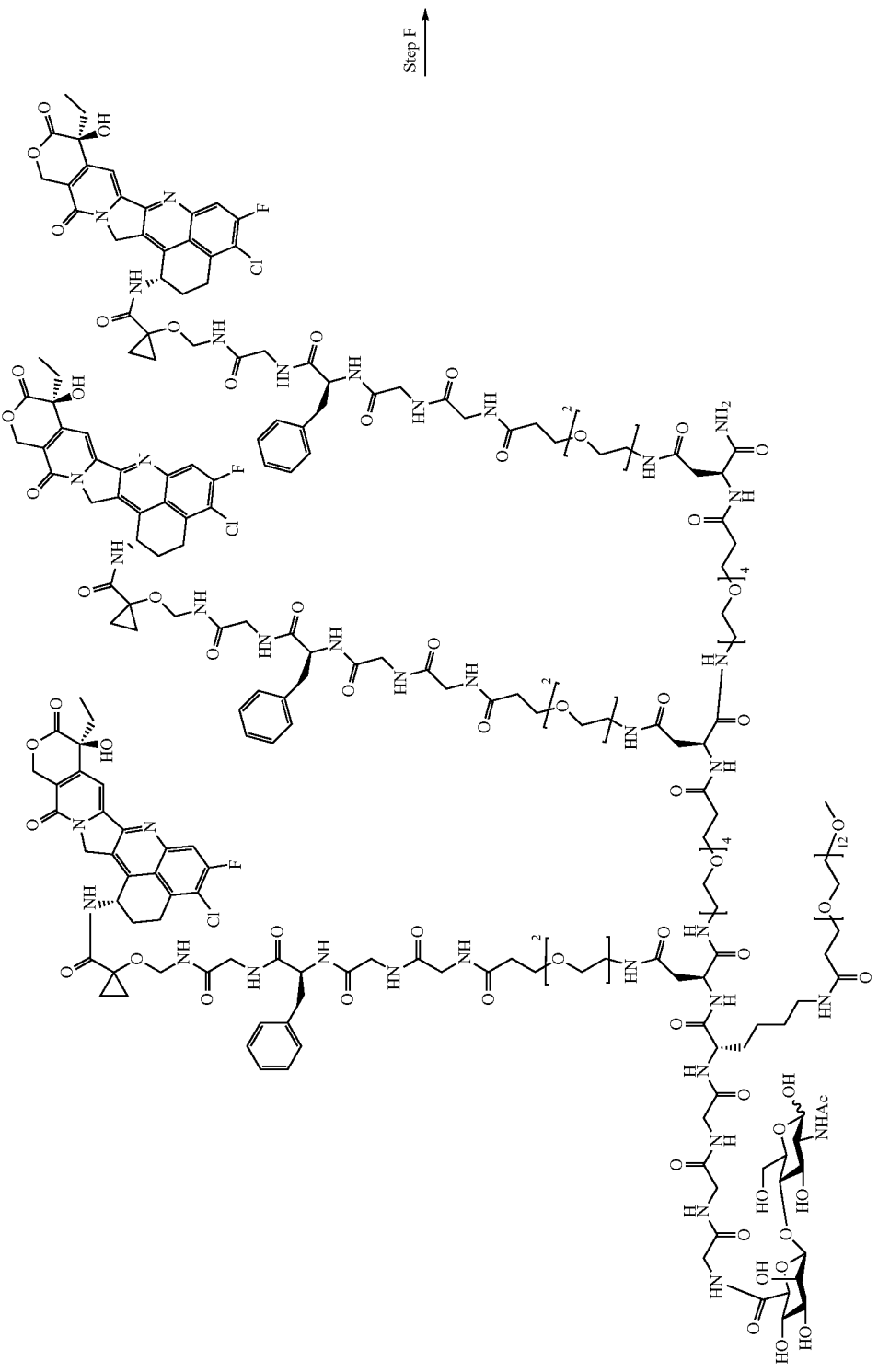

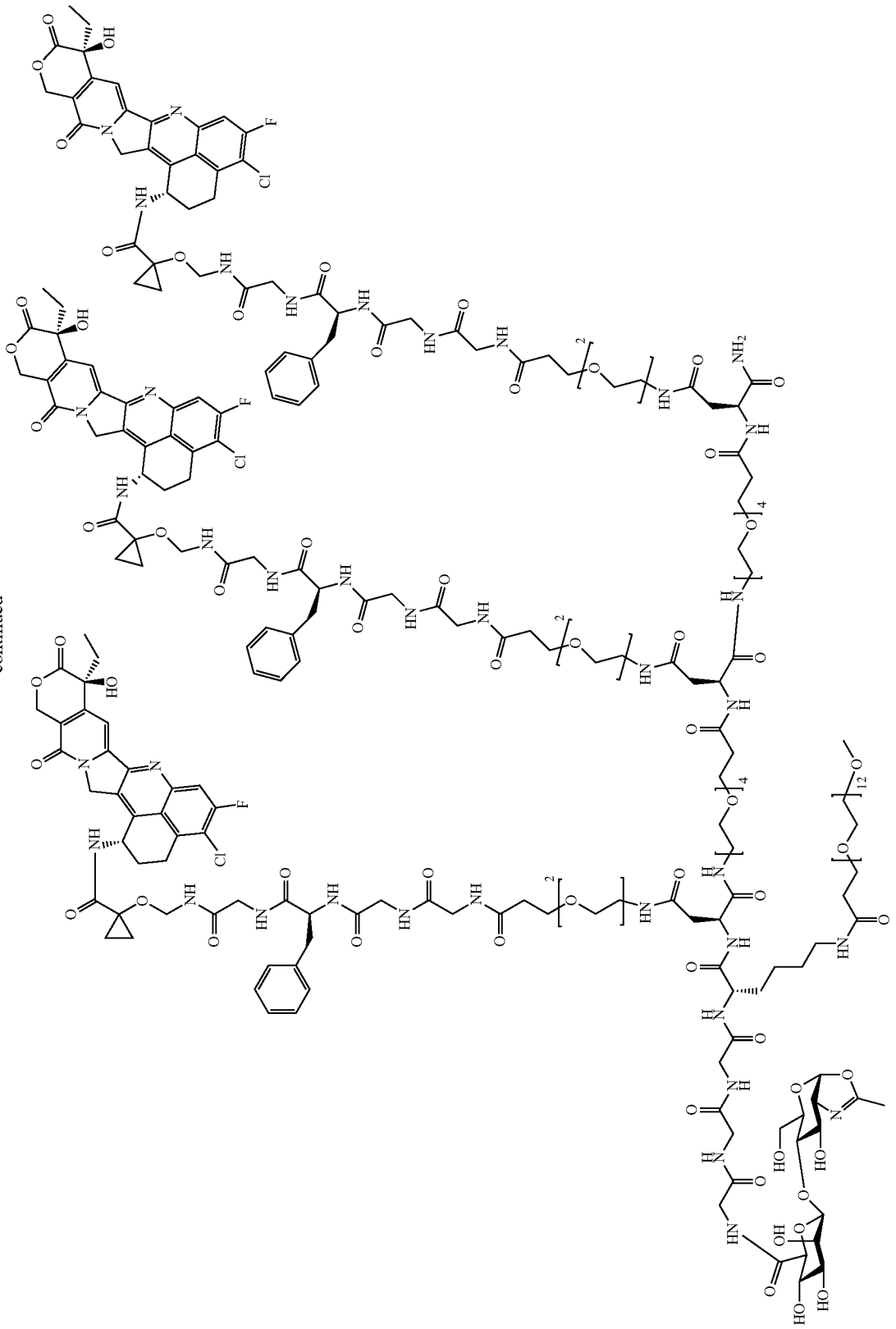
LP-7

Step A: Synthesis of Compound LP-7b

Compound LP-7a was synthesized by a method of polypeptide solid-phase synthesis, refer to a similar method of LP-6-2.

The compound LP-7a (1.0 equiv.) and the compound LP-6-1 (3.6 equiv.) were added into a reaction flask, and dissolved in DMF. Subsequently, DIPEA (6.0 equiv.) was added and well stirred, and then, HATU (3.6 equiv.) was added into the system for reaction at rt. Monitoring was performed by HPLC until the reaction was complete (about 2 h). The reaction system was prepared directly by prep-HPLC. A preparation solution was freeze-dried to afford compound LP-7b (white solid, yield 56%). MS (ESI) m/z of $C_{191}H_{280}O_{66}N_{29}{}^{3+}$ $[M+3H]^{3+}$: calc 1345.3, found 1345.8.

Step B: Synthesis of Intermediate LP-7c

Compound LP-7b was dissolved in purified water, and a certain amount of palladium hydroxide (10 wt % $Pd(OH)_2$ on activated carbon) was added. The system was replaced with hydrogen three times, and stirred at rt for 1.5 h, during which, the extent of reaction was monitored, then the reaction solution was prepared directly by prep-HPLC after being purified to afford compound LP-7c (white solid, yield 80%). MS (ESI) m/z of $C_{170}H_{262}O_{66}N_{29}{}^{3+}$ $[M+3H]^{3+}$: calc 1255.3, found 1255.9.

Step C: Synthesis of Intermediate LP-7d

Compound LP-7c (1.0 equiv.) and compound LP-6-3 (1 to 10 equiv.) were weighed and dissolved in DMF. DIPEA (1 to 20 equiv.) was added and well stirred. Subsequently, HATU (1 to 10 equiv.) was added for reaction at rt. Monitoring by HPLC was performed until the reaction was complete (about 2 h). The reaction was directly used for the next reaction. MS (ESI) m/z of $C_{239}H_{313}O_{75}Cl_3F_3N_{38}{}^{3+}$ $[M+3H]^{3+}$: calc 1692.4, found 1692.9.

Step D: Synthesis of Compound LP-7e

Compound LP-7d was dissolved in DMF, and diethylamine was added for reaction at rt. Monitoring by HPLC was performed until the reaction was complete (about 0.5 h). After the reaction, the pH was regulated to neutral, then preparation was performed by pre-HPLC, and freeze drying was performed to afford compound LP-7e (yellow solid, yield 73%). MS (ESI) m/z of $C_{224}H_{303}O_{73}Cl_3F_3N_{38}{}^{3+}$ $[M+3H]^{3+}$: calc 1618.3, found 1618.5.

Step E: Synthesis of Compound LP-7f

Compound 1 (0.5 to 5.0 equiv.) and compound LP-7e (1.0 equiv.) were dissolved in DMF. DIPEA (1 to 10 equiv.) was added and well stirred at 0° C. HATU (0.5 to 10 equiv.) was added. The resulting reaction system was stirred at 0° C. The extent of reaction was monitored by HPLC until the reaction was complete (about 2 h). The reaction system was prepared directly by prep-HPLC, and the preparation solution was freeze-dried to afford compound LP-7f (yellow solid, yield 65%). MS (ESI) m/z of $C_{238}H_{325}O_{84}Cl_3F_3N_{39}{}^{4+}$ $[M+4H]^{4+}$: calc 1308.8, found 1309.0.

15.6 Step F: Synthesis of Compound LP-7

Compound LP-7f was weighed and dissolved in purified water. After the compound was stirred in an ice water bath and cooled, $Et_3N$ (1 to 100 equiv.) and DMC (2-chloro-1,3-dimethylimidazolidinium chloride, CAS: 37091-73-9, 1 to 100 equiv.) were added. The extent of reaction was monitored by HPLC. After the reaction was complete, purification was performed by prep-HPLC, and the preparation solution was freeze-dried to afford compound LP-7 (light yellow solid, yield 50%).

III. Selection or Preparation of Antibody

Selection of Antibody

Any molecule comprising glycan chain in the Fc region of the antibody may be selected as the macromolecular moiety of the antibody-drug conjugate prepared from the substrate and conjugation method of the present disclosure, including, but not limited to, antibodies/bispecific antibodies/FC fusion proteins/single-chain antibodies, etc.

In the following specific examples, Trastuzumab may be selected, which is commercially available.

In addition, the antibody may be an engineered antibody. The preparation example of the antibody is as follows:

Example 10: Preparation of Engineered Anti-HER2 and Trop2 Antibodies

For the production, purification and identification of an anti-human ErbB2/HER2 antibody mAb-1 and an anti-human TROP2 antibody mAb-2, see Example 1 of Patent CN 106856656 B, which is incorporated in its entirety herein as a reference.

IV. Preparation, Characterization, and Activity Test of ADC

Example 11: Preparation and Characterization of ADC-1

Glycan remodeling at the Fc region of an antibody mAb-1 was promoted by endoglycosidase, and a linker-payload was specifically conjugated onto the antibody to form corresponding ADC.

1) Treatment of antibody mAb-1: the antibody was treated by using an ultra-filtration or dialysis or desalting column method, and a storage buffer of the antibody was replaced with 50 mM Tris HCl (pH value between 5 and 8) and 150 mM NaCl.

2) Preparation of ADC-1: the conjugation reaction of the antibody mAb-1 with the linker-payload LP-1 was catalyzed by the endoglycosidase Endo S2 to prepare ADC-1. In a 1× endonuclease buffer, the antibody mAb-1 was fully mixed with LP-1 in an appropriate molar ratio (1:1 to 1:100), the endoglycosidase Endo S2 was added, and well mixing was performed. The conjugation reaction in the well mixed state was carried out at 4° C. to 40° C. for 0.5 to 20 h. Purification was performed after the reaction was completed. Purified ADC-1 was stored at 4° C. or −80° C. in 1×PBS pH 7.4.

Characterization data for the antibody-drug conjugate ADC-1 are described below.

SDS-PAGE Detection Analysis of ADC-1

Upon the completion of the conjugation, the purity and conjugation efficiency of ADC-1 were tested by SDS-PAGE method. The SDS-PAGE detection results of ADC-1 are as shown in FIG. 1. The conjugation reaction occurs on the heavy chain of the antibody in a site-specific manner, and the heavy chain conjugated with cytotoxin has a significant molecular weight transition compared with the heavy chain unconjugated with the cytotoxin. The purity of the conjugate meets expectation.

HIC-HPLC Detection Analysis of ADC-1

HIC-HPLC: Proteomix HIC Butyl-NPS 4.6*100 mm 5 um Non-Porous column; column temperature 30° C.; 1.5 M ammonium sulfate+20 mM phosphate buffer salt, pH 7.0 as mobile phase A; 20 mM phosphate buffer salt:isopropanol=7:3 (v/v) as mobile phase B; flow rate 0.8 mL/min; gradient method: phase B increased from 10% to 100% within 8 min; and wavelength 280 nm were used for detecting the DAR distribution of ADC-1.

Figure 2:
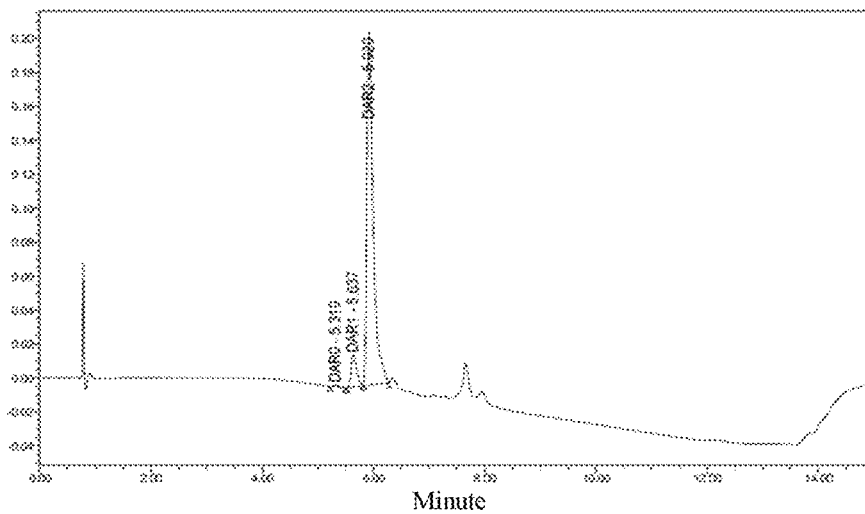
FIG. 2. HIC-HPLC detection analysis of ADC-1

The detection results are as shown in FIG. 2. Antibodies unconjugated with LP-1 are <1%. The conjugated product is mainly DAR 2, and the DAR mean of ADC is 1.93.

High-Precision Molecular Weight Mass Spectrometry (ESI-MS) Analysis of ADC-1

ADC-1 was analyzed and detected by using high-precision molecular weight mass spectrometry. The analysis and detection results show that the apparent molecular weight is 150539.27 and the theoretical molecular weight is 150538.78, which meets expectation, thereby confirming that the Fc region of each heavy chain is conjugated with the cytotoxin molecule.

SEC-HPLC Detection Analysis of ADC-1

Figure 3:
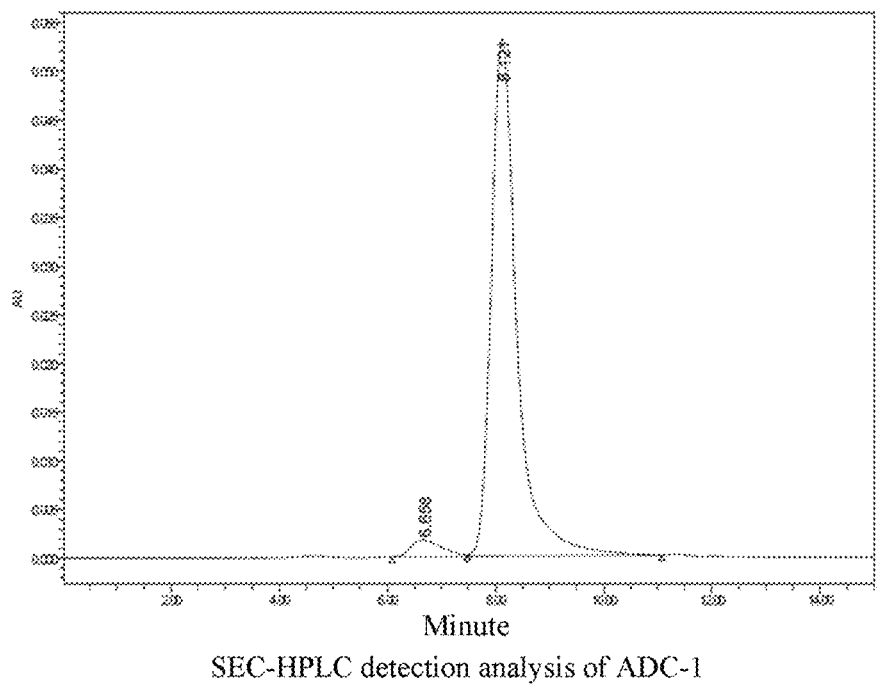
FIG. 3. SEC-HPLC detection analysis of ADC-1

The high molecular weight aggregation degree of ADC-1 was detected using SEC column analysis. The detection results are shown in FIG. 3. The high molecular weight aggregates at 6.7 mM in ADC-1 is less than 5%. ADC samples are mainly present in the form of monomers, and the damage of the conjugation reaction to the antibody is negligible.

Detection of Affinity of ADC-1 for Cell Surface ErbB2/HER2

1) HER2ECD was taken, prepared with a CBS coating buffer (0.1 M carbonate buffer, pH 9.6) to be 1 µg/mL, with 100 µL per well, and coated at 25° C. for 60 mM. 2) After the coating, a plate was washed with PBST three times, the plate was blocked (300 µL/well) with a blocking buffer (5% skimmed milk powder) at 25° C. under 200 rpm, and incubation was performed for 60 mM. 3) After the blocking, the plate was washed with PBST three times, antibodies mAb-1 and ADC-1 (100 µL/well) were added, the plate was placed at 25° C., and incubation was performed under the condition of 200 rpm for 60 mM 4) After incubation with the sample, the plate was washed with PBST three times, anti-human IgG Fc-HRP was added, 100 µL per well and incubation was performed at 25° C. and 200 rpm for 60 mM 5) After incubation for 60 mM, color development was performed with TMB (100 µL/well) for 5 mM, then the reaction was stopped with a stop buffer, and reading was performed at OD450.

Figure 4:
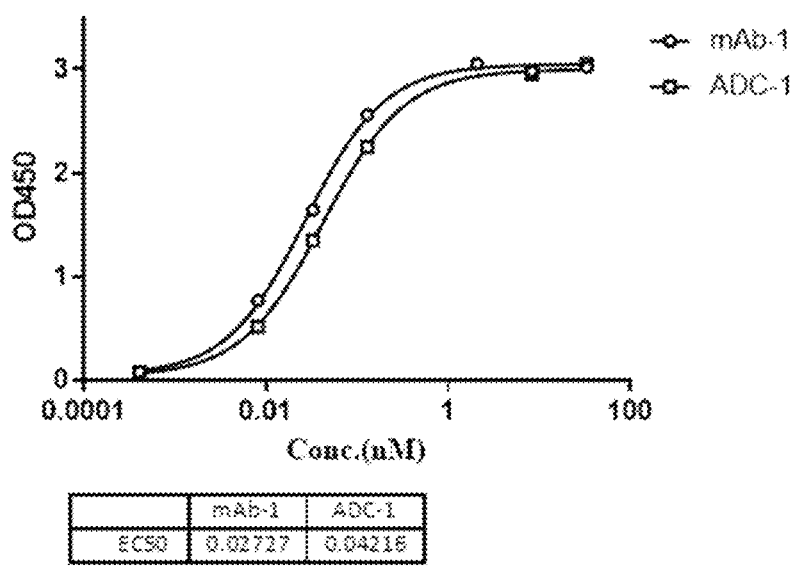
FIG. 4. Detection of affinity of ADC-1 with cell surface ErbB2/HER2 ($EC_{50}$, nM)

The Elisa test results show that there is no significant difference in antigen affinity between mAb-1 nude monoclonal antibody and ADC-1 for HER2ECD, as shown in FIG. 4.

Example 12: In Vitro Activity Test of ADC-1 (In BT-474, NCI-N87, HepG2 Cells)

The influence of ADC-1 on the proliferation of the tumor cells at different expression levels of ErbB2/HER2 was tested with the following methods 1) ErbB2/HER2-positive human breast cancer cells BT-474, ErbB2/HER2-positive human gastric cancer cells NCI-N87 and ErbB2/HER2-negative human liver cancer cells HepG2 were inoculated into a 96-well cell plate at 100 µL/well (1000 to 10000 cells), and incubated overnight in a cell incubator under the conditions of 37° C., 5% $CO_2$, 95% air and 100% humidity.

2) Different concentrations (10, 3.3, 1.1, 0.37, 0.12, 0.041, 0.014, 0.0046, 0.0015, and 0.00051 nM) of ADC-1 or antibody mAb-1 or different concentrations (30, 10, 3.3, 1.1, 0.37, 0.12, 0.041, 0.014, 0.0046, and 0.0015 nM) of MMAE (monomethylauristatin E) were added to ErbB2/HER2-positive cells cultured overnight; different concentrations (100, 10, 3.3, 1.1, 0.37, 0.12, 0.041, 0.014, 0.0046, and 0.0015 nM) of ADC-1 or antibody mAb-1 or different concentrations (30, 10, 3.3, 1.1, 0.37, 0.12, 0.041, 0.014, 0.0046, and 0.0015 nM) of MMAE were added to the ErbB2/HER2-negative cells cultured overnight; and puromycin with a final concentration of 5 µM was added to the control group. Incubation was further performed at 37° C. for 72 to 120 h.

3) The cell plate was removed from the 37° C. cell incubator, and equilibrated for about 30 min to rt. 100 µL of CellTiter Glo reagent was added into each well, a shaker shook for 2 min, followed by standing in a dark place at rt for 10 min, and the relative light unit (RLU) was measured with a Cytation 3 microplate reader.

Figure 5:
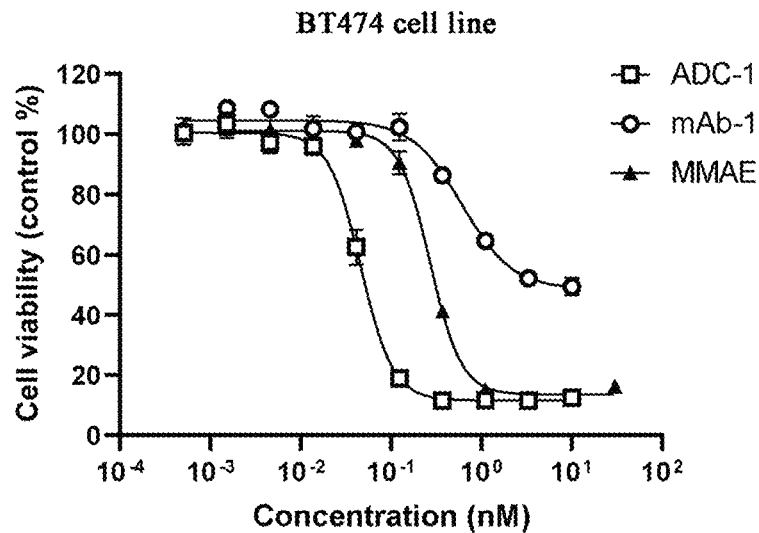
FIG. 5. Proliferation inhibition effect of ADC-1 and other different drugs against tumor cells BT474 ($IC_{50}$, nM)
Figure 6:
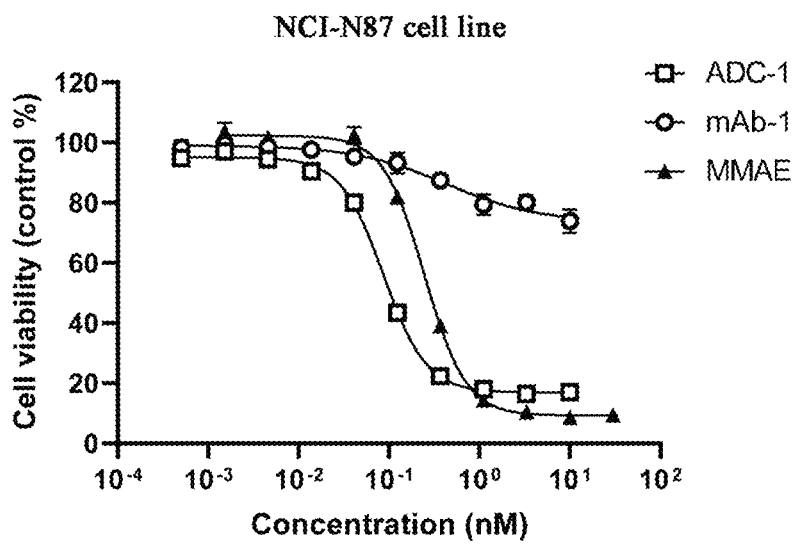
FIG. 6. Proliferation inhibition effect of ADC-1 and other different drugs against tumor cells NCI-N87 ($IC_{50}$, nM)
Figure 7:
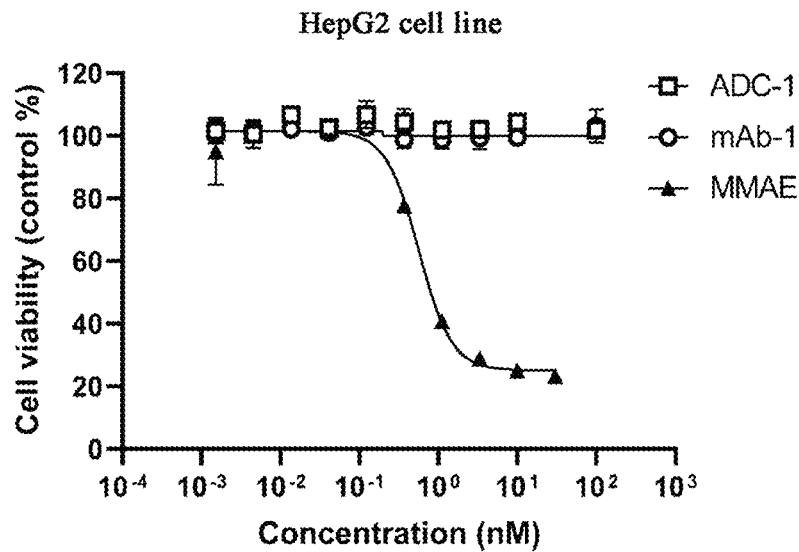
FIG. 7. Proliferation inhibition effect of ADC-1 and other different drugs against tumor cells HepG2 ($IC_{50}$, nM)

4) The results of the proliferation inhibition action of different drugs on the tumor cells are shown in Table 1, Table 2 and FIGS. 5 to 7. ADC-1 and MMAE small molecule toxins have obvious proliferation inhibition activity on the ErbB2/HER2-positive cells, the antibody mAb-1 monoclonal antibody has slight proliferation inhibition efficacy on the ErbB2/HER2-positive cells, and ADC-1 is significantly superior to the mAb-1 monoclonal antibody and the MMAE small molecule toxin. ADC-1 and mAb-1 monoclonal antibodies have no inhibition efficacy on ErbB2/HER2-negative cells.

TABLE 1

Proliferation Inhibition Effect of Different Drugs on Tumor Cells ($IC_{50}$, nM)

|  | ADC-1 | mAb-1 | MMAE |
| --- | --- | --- | --- |
| BT-474 | 0.04636 | 0.6093 | 0.2715 |
| NCI-N87 | 0.08706 | 0.4251 | 0.2481 |
| HepG2 | — | — | 0.5669 |

Note:
"—" undetected

TABLE 2

Proliferation Inhibition Effect of Different Drugs on Tumor Cell (the maximum killing percentage relative to the control group)

|  | ADC-1 | mAb-1 | MMAE |
| --- | --- | --- | --- |
| BT-474 | 88.39 | 51.19 | 86.46 |
| NCI-N87 | 83.17 | 26.36 | 90.78 |
| HepG2 | — | — | 74.88 |

Note:
"—" undetected

Example 13: In Vivo Activity Test of ADC-1 (NCI-N87 CDX Mouse Model)

The influence of ADC-1 on the tumor cell growth of an ErbB2/HER2 NCI-N87 CDX mouse model was tested using the following methods 1) Cell culture: NCI-N87 human gastric cancer tumor cells (ATCC, Manassas, VA, cat #CRL-5822) at logarithmic phase were collected, the cell density was adjusted with a matrix gel buffer (PBS:Matrigel=1:1), and 0.2 mL of NCI-N87 cell suspension prepared was subcutaneously injected into right shoulder blades of 7 to 9-week-old SPF-grade female BALB/c nude mice, with a cell inoculum size of $10\times10^6$/mouse.

2) The tumor diameter was measured with a vernier caliper, and the tumor volume was calculated according to the formula V=0.5 a*b² (where a is the longest diameter of the tumor and b is the shortest diameter of the tumor). After 5 days of cell inoculation, when the mean tumor volume range was 100-300 mm³, animals were randomly divided into a vehicle control group and ADC-1 3 mg/kg treatment group, with 5 animals in each group. Animals were administered via caudal veins, and the control group was given an equal volume of vehicle, and the day when the animals were grouped and administrated was defined as Day 0. The tumor volume of the animal in each group was measured twice a week within 35 days after administration. The tumor volumes of the animals on the day 35 were compared between groups, and the T/C value and TGI value were calculated with the tumor volume. The calculation formula was as follows: T/C %=$T_{RTC}/C_{RTV}$×100% ($T_{RTV}$: treatment group RTV; $C_{RTV}$: vehicle control group RTV). The relative tumor volume (RTV) was calculated according to the results of tumor measurements. The calculation formula was RTV=$V_t$/V0, with V0 representing an average tumor volume measured at the time of grouping, Vt representing an average tumor volume at a certain measurement, and $T_{RTV}$ and $C_{RTV}$ being taken from data of the same day. Calculation of TGI (%): TGI (%)=[1-(average tumor volume at the end of treatment in a treatment group-average tumor volume at the start of administration in this treatment group)/(average tumor volume at the end of treatment in a vehicle control group-average tumor volume at the start of treatment in the vehicle control group)]×100%.

3) Statistic analyses were performed on data between groups by using independent sample t-tests, and all the analyses were performed by using SPSS 17.0. P<0.05 indicates that the difference is statistically significant.

Figure 8:
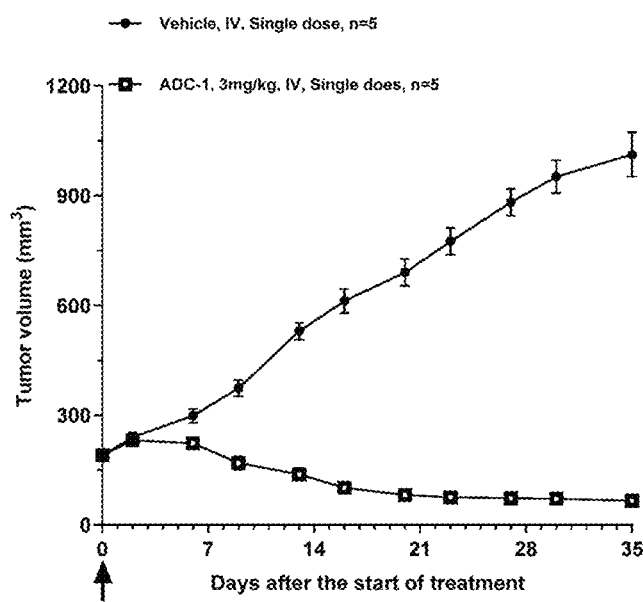
FIG. 8. Inhibition effect of ADC-1 in NCI-N87 CDX mouse model FIG. 9. SDS-PAGE detection analysis of ADC-2

4) Table 3 and FIG. 8 show that ADC-1 can significantly inhibit tumor growth in the NCI-N87 CDX mouse model compared to the vehicle control group.

TABLE 3

Inhibition Effect of ADC-1 on NCI-N87 CDX Mouse Model

| Administration Regimen | N | Tumor volume (mm³)[1] on day 35 | T/C[2] (%) | TGI[3] (%) | p value[4] |
|---|---|---|---|---|---|
| Vehicle | 5 | 1013 ± 60 | — | — | — |
| ADC-1, 3 mg/kg | 5 | 67 ± 10 | 6.57 | 115.07 | <0.001 |

Remarks:
1. Mean ± SEM;
2. T/C % = $T_{RTV}/C_{RTV}$ × 100% ($T_{RTV}$: treatment group RTV; $C_{RTV}$: vehicle control group RTV). The relative tumor volume (RTV) was calculated according to the results of tumor measurements. The calculation formula is RTV = $V_{35}/V_0$, where $V_0$ is the average tumor volume measured at the time of administration to the group (i.e., $D_0$), $V_{35}$ is the average tumor volume on day 35 after administration, and $T_{RTV}$ and $C_{RTV}$ are taken from data of the same day.
3. TGI (%) = [1-($T_{35}-T_0$)/ ($V_{35}-V_0$)] × 100)
4. P value was calculated according to the tumor volume.

Example 14: Preparation and Characterization of ADC-2

See the method described in Example 11 for preparation and characterization, except that the linker-payload used was LP-6. The characterization data of the antibody-drug conjugate ADC-2 are described below.

Figure 9:
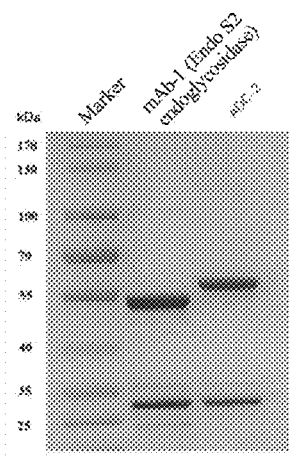
Figure 10:
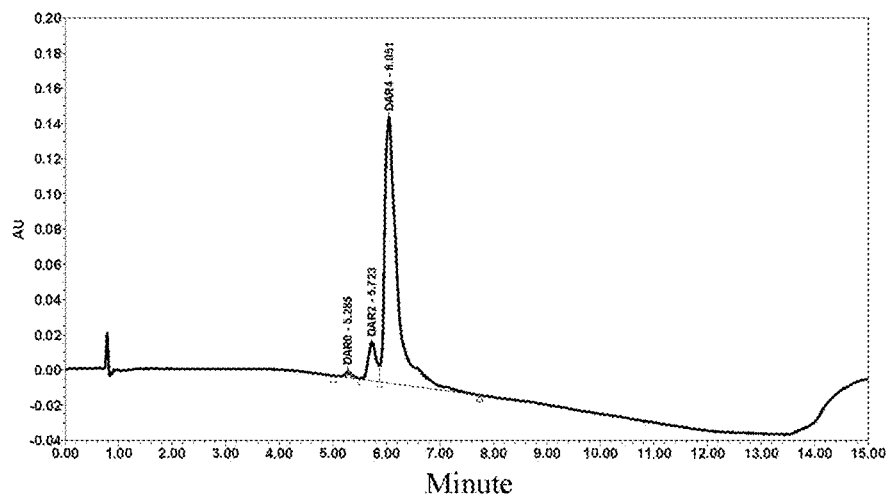
FIG. 10. HIC chromatogram of ADC-2

SDS-PAGE Detection analysis of antibody-drug conjugate ADC-2: after the conjugation reaction ended, the purity and conjugation efficiency of ADC-2 were detected by an SDS-PAGE method. The SDS-PAGE detection results of ADC-2 are as shown in FIG. 9. The conjugation reaction occurs on the heavy chain of the antibody in a site-specific manner, and the heavy chain of ADC-2 conjugated with the linker-payload has a significant molecular weight transition compared with the heavy chain of the monoclonal antibody with the glycan chain cut off, which proves successful site-specific conjugation of the linker-payload onto the heavy chain of the monoclonal antibody. The antibody unconjugated with the linker-payload is basically not observed in the conjugated product. The conjugation efficiency is as high as 95%, and the purity of the conjugated product meets expectation.

Figure 11:
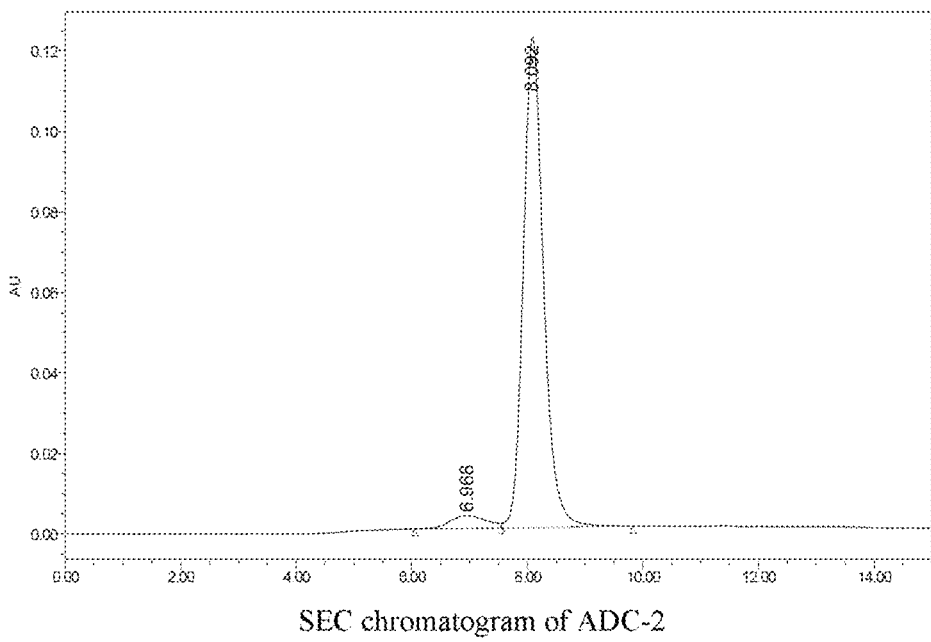
FIG. 11. SEC chromatogram of ADC-2

The HIC-HPLC detection analysis of ADC-2 has results as shown in FIG. 11, where the antibodies unconjugated with the cytotoxin are <5%, the conjugated product is mainly DAR4, and the DAR value of overall ADC-2 is around 3.8, as shown in the figure.

The SEC-HPLC detection analysis of ADC-2 is as shown in FIG. 11: the high molecular weight polymer in ADC is <5%, and the ADC sample at 8.1 min is present mainly in the form of monomers.

Plasma Stability Test of ADC-2
Experimental Design:

Mixed healthy human plasma (5 males and 5 females, mixed in an equal volume) was taken, and ADC-2 was added to a specific final concentration. The mixed healthy human plasma was divided into 4 portions, with 450 µL per portion, and incubated in an incubator at 37° C. The samples were collected at 0 h, 24 h, 48 h and 96 h. After the collection, the samples were stored in a refrigerator at -60° C. to -90° C. to detect the free load shedding rate and the DAR change rate.

LC-MS detection of small molecule toxin (the small molecule toxin of LP-6 involved in this example was represented by payload)

40 µL of each sample (except double blank) was taken, a certain amount of internal standard precipitant (1 ng/mL DXd) was added, and the mixture was shaken for at least 10 min; 40 µL of blank matrix was taken from the double blank and 120 µL of internal standard-free precipitant was added, and was shaken for at least 10 min, and centrifuged at 3600 g and 4° C. for 15 min. 60 µL of supernatant was pipetted into a sample injection vial, a certain amount of 0.1% FA ultrapure water was added, the mixture was shaken for at least 3 min, and HPLC detection was performed.

DAR Detection by Hybrid LC-MS Method 1 g of CNBr-activated agarose (Sigma, Cat #C9142) was weighed and put in a 50 mL centrifuge tube, and 50 mL of pre-cooled 1 mM HCl was added. The centrifuge tube was placed on a rotary mixer and incubated for at least 30 mM under the incubation conditions of 4° C. and 10 RPM. Centrifugation was performed for a certain time to remove 1 mM HCl. Sol was washed once with deionized water that is 5 to 10 times its volume, and then washed three times with 0.1 M NaHCO₃. An appropriate amount of HER2 ECD was taken, the buffer was replaced with 0.1 M NaHCO₃ by using a 30 kD ultrafiltration tube, and then HER2 ECD after the replacement was mixed with filler. The mixture was placed in a rotary mixer and incubated at 25° C. and 10 RPM for 2 h±10 mM for conjugation. 5 mL of 0.1 M NaHCO₃ buffer was then added, and centrifugation was performed for a certain time and washing was performed three times to remove unconjugated proteins. A certain amount of glycine (pH 8.0) was taken and added into filler, and the mixture was allowed to stand and block at 2° C. to 8° C. for 16 h to block unreacted chemical groups on the filler. First, the filler was washed with 5 mL of 0.1 M NaHCO₃ and centrifuged for a certain time, then the filler was washed with a certain amount of acetic acid buffer, and centrifuged for a certain time. The washing cycle was repeated several times. 0.1 mL of each sample was taken and put in a 1.5 mL EP tube. 0.1 mL of HER2 ECD conjugated filler was added. Incubation was performed at 25° C. and 10 RPM for 2 h. Washing was performed with 1 mL of PBST three times, and centrifugation was performed for a certain time. Elution and centrifugation were performed, and supernatant was taken to determine the concentration and LC-MS detection was performed.

Result Analysis:

ADC-2 is incubated in healthy mixed human plasma for 0 h, 24 h, 48 h and 96 h, with the DAR change rates of 100.00%, 106.7%, 104.2% and 106.5%. The shedding ratios of the small molecule toxins are only 0.006%, 0.179%, 0.373% and 1.07%, respectively. The above results show that after ADC-2 is incubated at 37° C. for 96 h in the healthy mixed human plasma, its toxin shedding amount is extremely low, and DAR remains stable. Low toxin shedding indicates that the toxic side effects caused by free toxins clinically are significantly reduced, and high DAR stability indicates that the antibody molecules can target and deliver more toxin molecules to tumor sites, thereby improving the drug efficacy. The synergy of low toxin shedding and high DAR stability can significantly broaden the therapeutic window of ADC-2.

Example 15: In Vitro Activity Test of ADC-2 (In SK-BR-3, HCC1954, MDA-MB-468 Cells)

The influence of ADC-2 on the proliferation of the tumor cell at different expression levels of ErbB2/HER2 was tested by the following methods.

Figure 12:
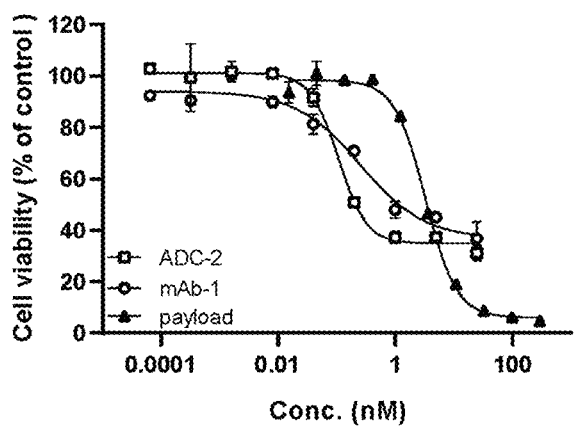
FIG. 12. Proliferation inhibition effect of ADC-2 and other different drugs against tumor cells SK-BR-3 ($IC_{50}$, nM)
Figure 13:
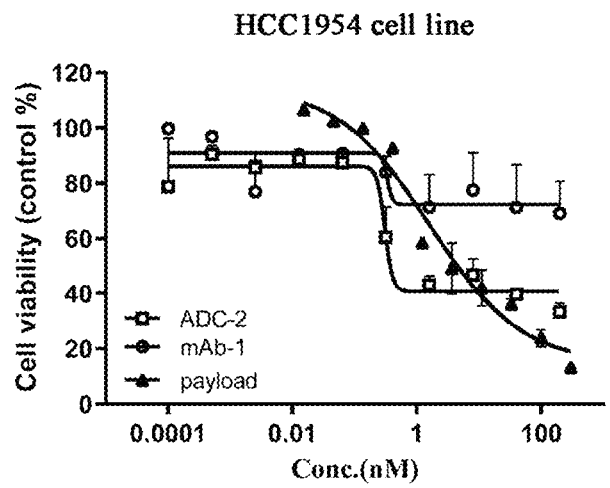
FIG. 13. Proliferation inhibition effect of ADC-2 and other different drugs against tumor cells HCC1954 ($IC_{50}$, nM)
Figure 14:
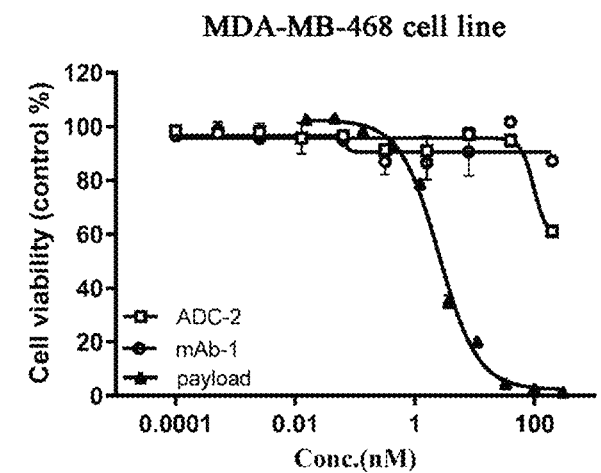
FIG. 14. Proliferation inhibition effect of ADC-2 and other different drugs against tumor cells MDA-MB-468 (IC50, nM)

Referring to the method described in Example 12, the antibody-drug conjugate ADC-2 was tested for its effect on the proliferation of cancer cells at different expression levels of ErbB2/HER2. For example, ErbB2/HER2-positive human tumor cells such as SK-BR-3 and HCC1954, and ErbB2/HER2-negative human tumor cells such as MDA-MB-468 were selected. The results of the proliferation inhibition action of different drugs on the tumor cells are as shown in Table 4, Table 5 and FIGS. 12 to 14. ADC-2 and small molecule toxins have obvious proliferation inhibition action on the ErbB2/HER2-positive cells, the antibody mAb-1 monoclonal antibody has certain proliferation inhibition action on the ErbB2/HER2-positive cells, and ADC-2 is significantly superior to mAb-1. ADC-2 and mAb-1 monoclonal antibodies have no inhibition action on the ErbB2/HER2-negative cells, which shows good targeting performance.

TABLE 4

Proliferation Inhibition Action of Different Drugs on Tumor Cells (IC50, nM)

|  | ADC-2 | mAb-1 | Small molecule toxin |
|---|---|---|---|
| SK-BR-3 | 0.1076 | 0.2565 | 3.321 |
| HCC1954 | 0.4355 | — | 1.622 |
| MDA-MB-468 | — | — | 2.558 |

Note:
"—" undetected

TABLE 5

Proliferation Inhibition Action of Different Drugs on Tumor Cell (the maximum killing percentage relative to the control group)

|  | ADC-2 | mAb-1 | Small molecule toxin |
|---|---|---|---|
| SK-BR-3 | 65.17 | 63.17 | 93.98 |
| HCC1954 | 59.29 | 27.68 | 85.40 |
| MDA-MB-468 | 39.00 | 13.00 | 97.74 |

Note:
"—" undetected

Example 16: Preparation and Characterization of ADC-3

See the method described in Example 11 for preparation and characterization of an antibody-drug conjugate ADC-3, except that the antibody used was an anti-TROP2 antibody, i.e., mAb-2, the linker-payload used was LP-6. The characterization data of the antibody-drug conjugate ADC-3 are described below.

Figure 15:
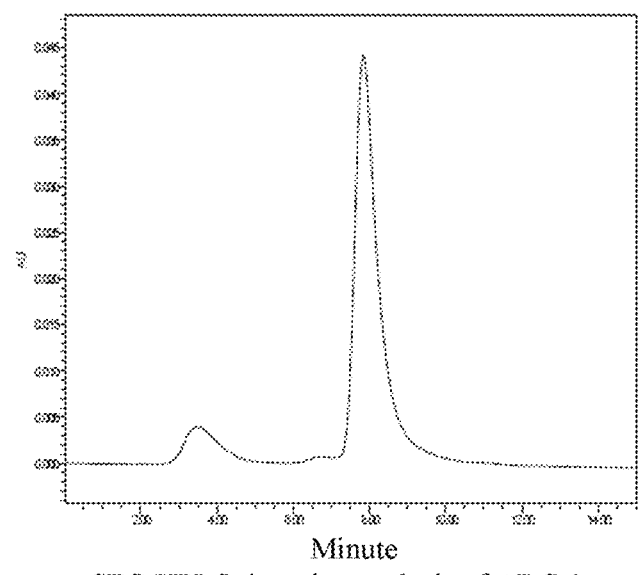
FIG. 15. SEC-HPLC detection analysis of ADC-3

SEC-HPLC Detection Analysis of ADC-3: the high molecular weight aggregation degree of ADC-1 was detected by using SEC column analysis. The detection results are as shown in FIG. 15. The high molecular weight polymer is less than 5%. ADC samples are mainly present in the form of monomers, and the damage of the conjugation reaction to the antibody is negligible.

High-Resolution Mass Spectrometry (ESI-MS) DAR Value Analysis of Antibody-Drug Conjugate ADC-3

Figure 16:
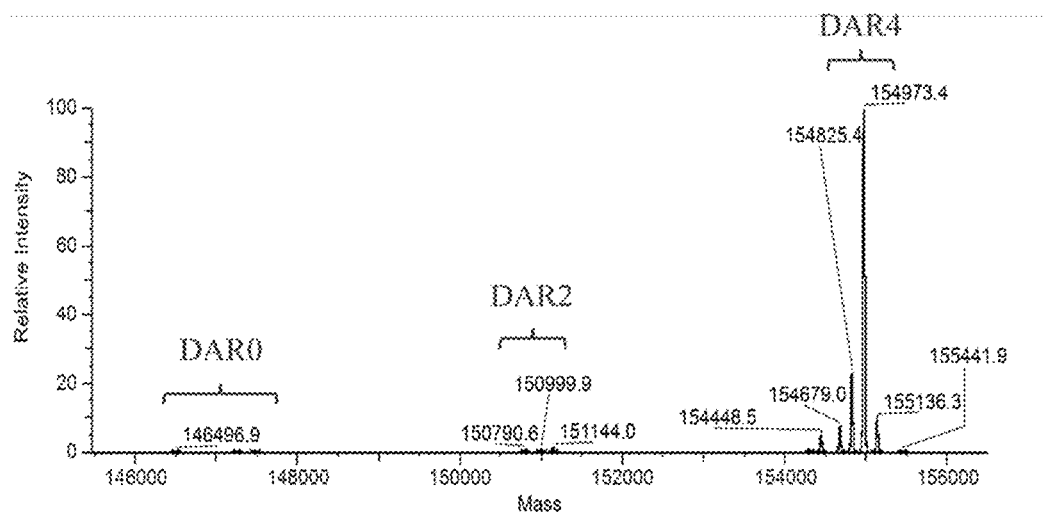
FIG. 16. High resolution mass spectrometry deconvolution diagram of ADC-3

The molecular weight of ADC-3 was resolved by a high-resolution mass spectrometer. A deconvolved mass spectrum is shown in FIG. 16. By comparing the measured molecular weight with the theoretical molecular weight, each main molecular weight variant could be attributed, and DAR value analysis was performed by using the mass spectrometry abundance of each major molecular weight variant, and its DAR mean was calculated to be 3.93.

Example 17: In Vitro Activity Test of ADC-3 (In BxPC-3, FaDu, HepG2 Cells)

Figure 17:
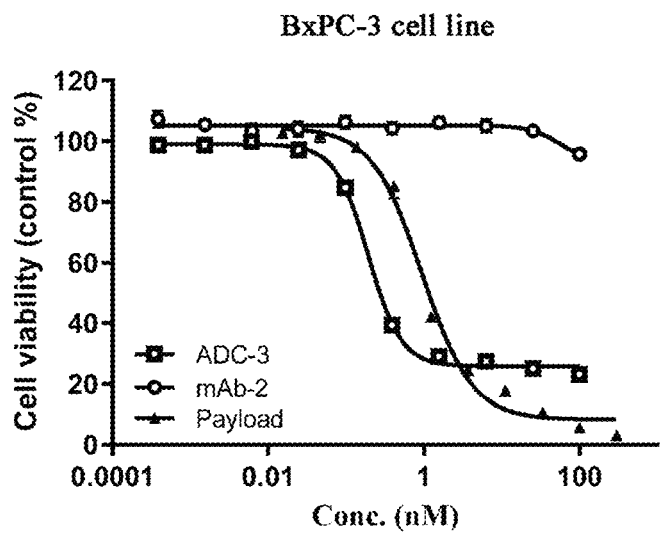
FIG. 17. Proliferation inhibition effect of ADC-3 and other different drugs against tumor cells BxPC-3 ($IC_{50}$, nM)
Figure 18:
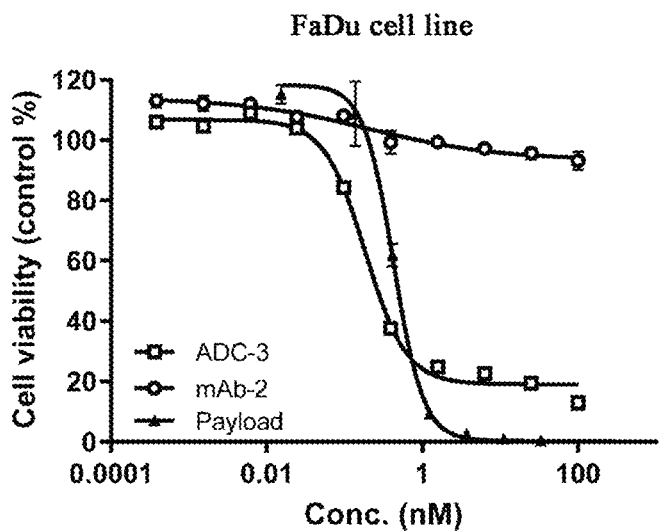
FIG. 18. Proliferation inhibition effect of ADC-3 and other different drugs against tumor cells FaDu ($IC_{50}$, nM)
Figure 19:
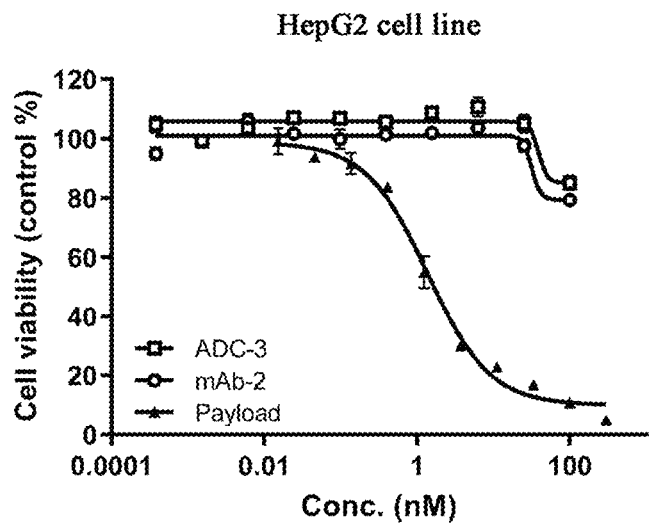
FIG. 19. Proliferation inhibition effect of ADC-3 and other different drugs against tumor cells HepG2 ($IC_{50}$, nM)

Referring to a similar operation of the method described in Example 12, an antibody-drug conjugate ADC-3 was tested for the proliferation inhibition action at different concentration gradients on cancer cells at different expression levels of TROP2. For example, BxPC-3, FaDu, HepG2 and other human tumor cells were selected. The results of the proliferation inhibition action of different drugs on the tumor cells are as shown in Table 6 and FIGS. 17 to 19, where ADC-3 and small molecule toxins have obvious proliferation inhibition action on TROP2-positive cells, the TROP2 antibody, i.e., mAb-2, has no obvious proliferation inhibition action on the TROP2-positive cells, and ADC-3 is significantly superior to the monoclonal antibody and the small molecule toxins. ADC-3 and mAb-2 monoclonal antibodies have no inhibition action on the TROP2-negative cells, which shows good targeting performance.

TABLE 6

Proliferation Inhibition Action of Different Drugs on Tumor Cells (IC50, nM)

| | IC50 (nM) | | |
|---|---|---|---|
| | BxPC-3 (TROP2 high expression) | FaDu (TROP2 high expression) | HepG2 (TROP2-negative) |
| ADC-3 | 0.1928 | 0.1839 | — |
| mAb-2 | — | — | — |
| Small molecule toxin | 0.9460 | 0.4250 | 1.383 |

Note:
"—" undetected

Example 18: In Vivo Activity Test of ADC-3 (NCI-N87 CDX Mouse Model)

Figure 20:
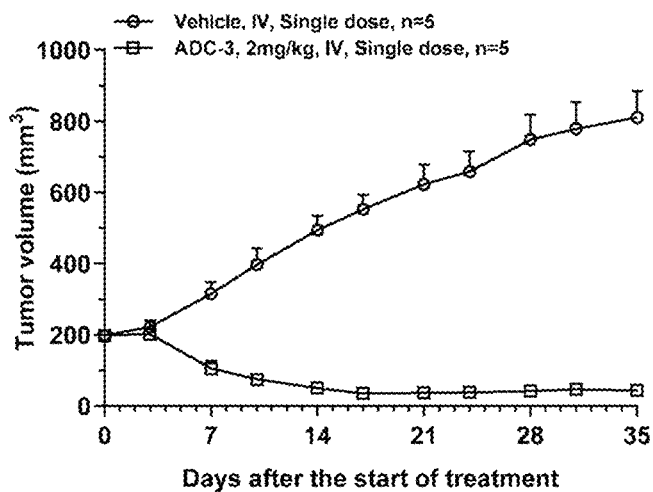
FIG. 20. Tumor inhibition effect of ADC-3 in NCI-N87 CDX mice
Figure 21:
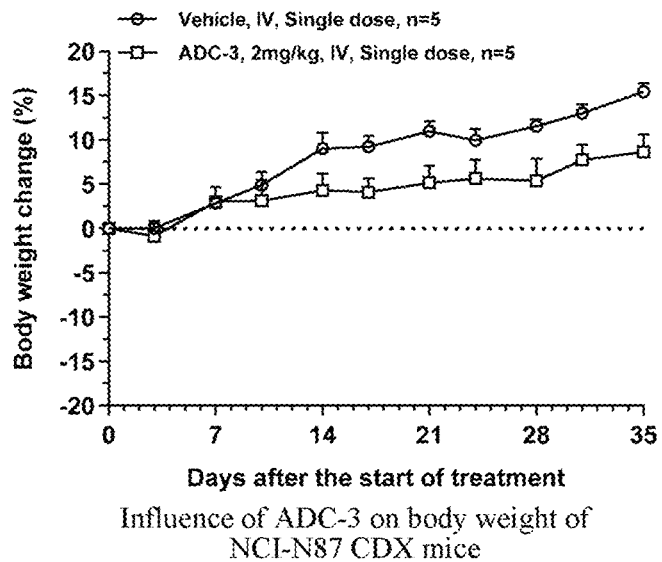
FIG. 21. Influence of ADC-3 on body weight of NCI-N87 CDX mouse model.

Referring to the similar method described in Example 13, the action of ADC-3 in a tumor growth inhibition method in an NCI-N87 CDX mouse model was evaluated. The tumor growth curve and body weight change curve after administration are shown in FIGS. 20 to 21. ADC-3 shows good tumor growth inhibition and good safety, and the experimental mice does not show weight loss-related toxicity.

Example 19: Preparation and Characterization of ADC-4

For the preparation and characterization of ADC-4, see the method described for ADC-1 for preparation and characterization, except that the antibody used was an anti-TROP2 antibody, i.e., mAb-2. The characterization data of the antibody-drug conjugate ADC-4 are described below.

Figure 22:
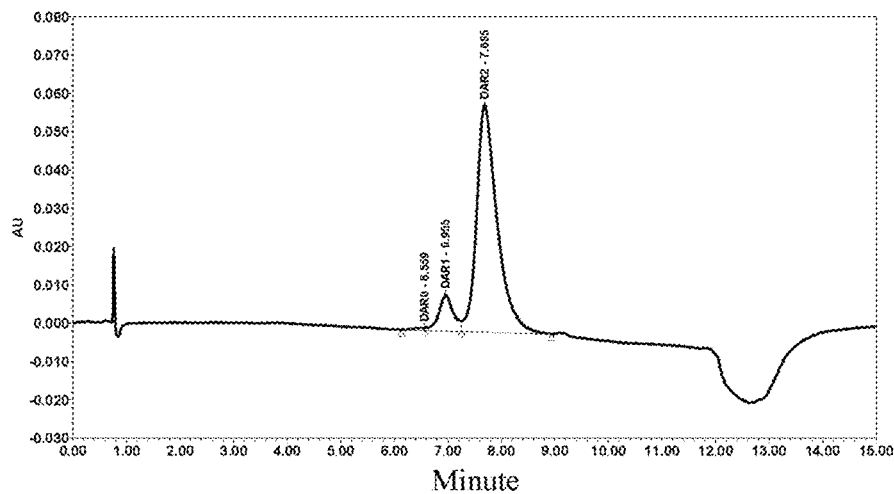
FIG. 22. HIC-HPLC analysis diagram of ADC-4
Figure 23:
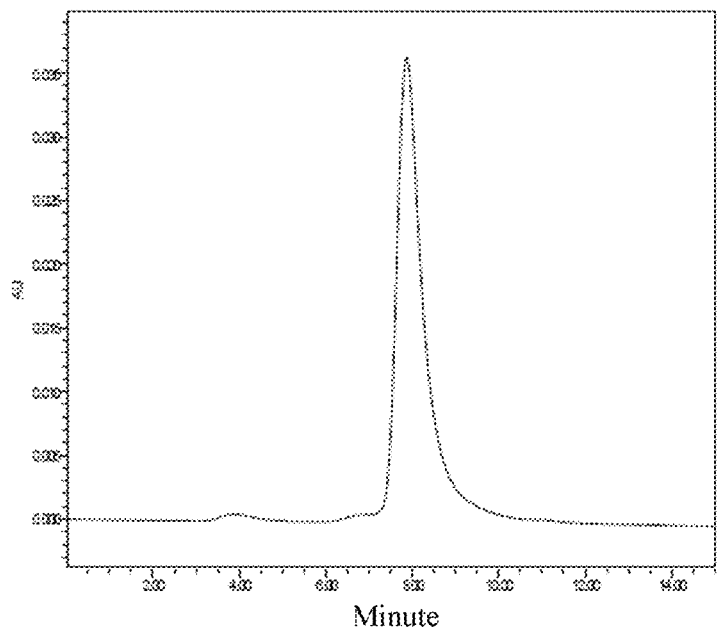
FIG. 23. SEC-HPLC analysis diagram of ADC-4

HIC-HPLC detection analysis of ADC-4: the detection results are as shown in FIG. 22. The antibodies unconjugated with the cytotoxin are <5%. The conjugated product is mainly DAR2, and the DAR value of overall ADC-4 is 1.89. The SEC-HPLC detection analysis of ADC-4 is as shown in FIG. 23, where the high molecular weight polymer in ADC is <5%, and the ADC sample is present mainly in the form of monomers.

Example 20: Preparation and Characterization of ADC-5

For the preparation and characterization of ADC-5, see the method described for ADC-1 for preparation and characterization, except that the antibody used was an anti-TROP2 antibody, i.e., mAb-2, and the linker-payload used was LP-2. The characterization data of the antibody-drug conjugate ADC-5 are described below.

Figure 24:
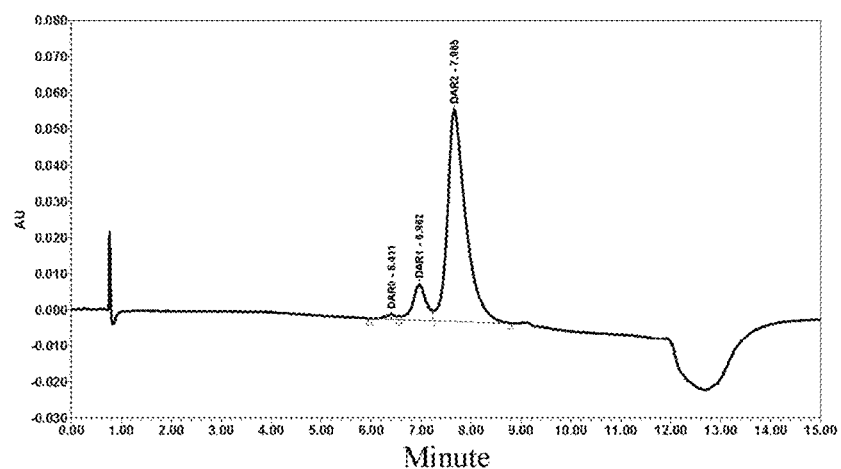
FIG. 24. HIC-HPLC analysis of ADC-5
Figure 25:
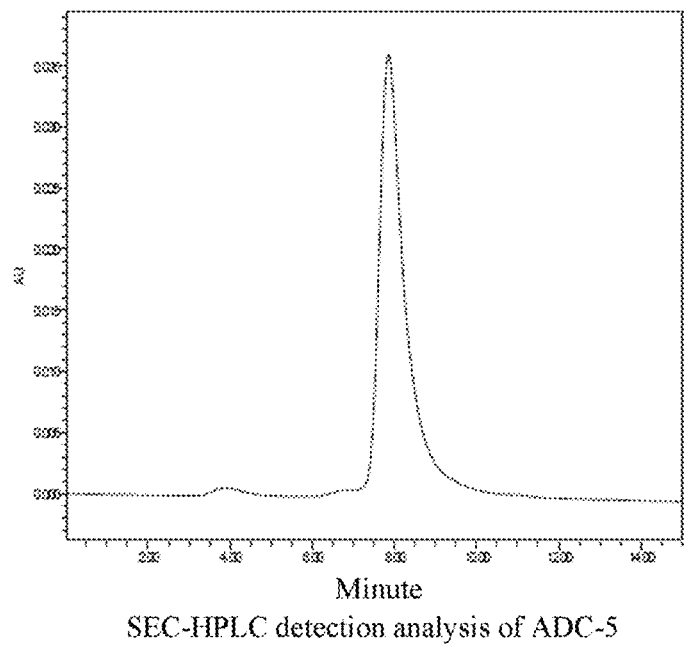
FIG. 25. SEC-HPLC analysis of ADC-5

HIC-HPLC detection analysis of ADC-5: the detection results are as shown in FIG. 24. The antibodies unconjugated with the cytotoxin are <5%. The conjugated product is mainly DAR2, and the DAR value of overall ADC-5 is 1.87. The SEC-HPLC detection analysis of ADC-5 is as shown in FIG. 25: the high molecular weight polymer in ADC is <5%, and the ADC sample is present mainly in the form of monomers.

Example 21: In Vitro Activity Comparison of ADC-4 and ADC-5 (In BxPC-3, FaDu, HepG2 Cells)

Figure 26:
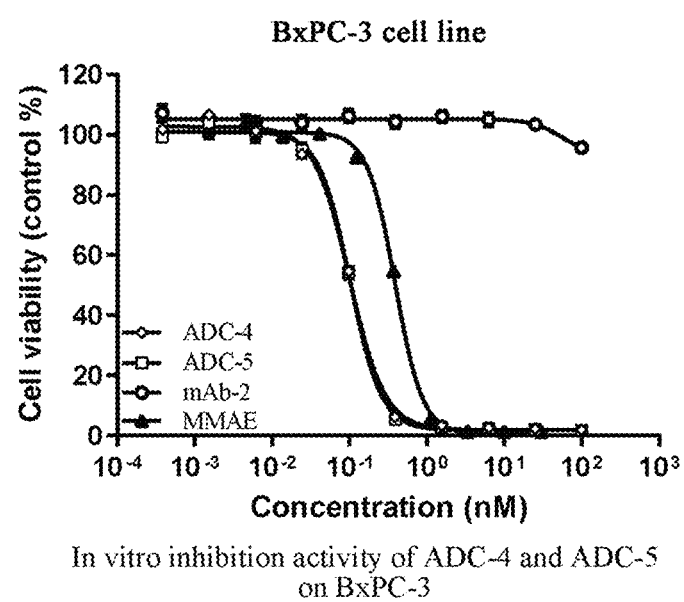
FIG. 26. In vitro inhibition activity of ADC-4 and ADC-5 against BxPC-3 cells
Figure 27:
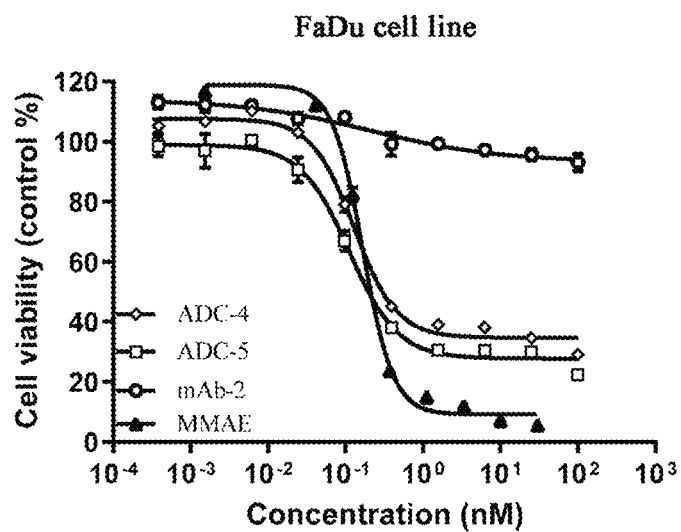
FIG. 27. In vitro inhibition activity of ADC-4 and ADC-5 against FaDu cells
Figure 28:
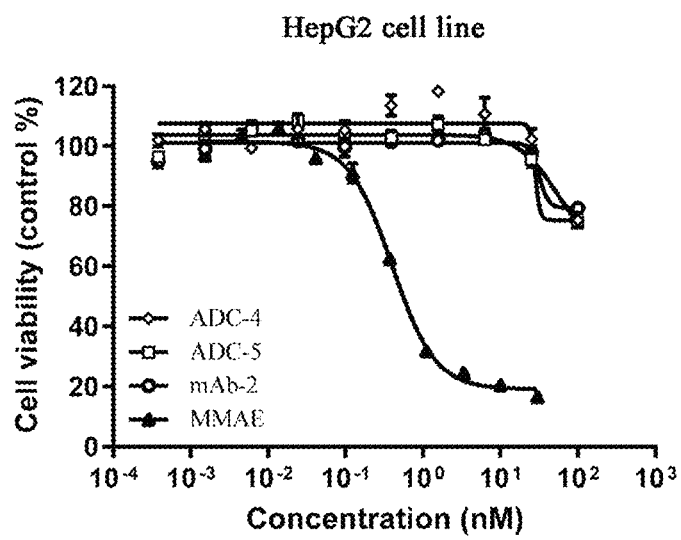
FIG. 28. In vitro inhibition activity of ADC-4 and ADC-5 against HepG2 cells

Referring to the operation of the method described in Example 12, the antibody-drug conjugates ADC-4 and ADC-5 were tested for its effect on the proliferation of the cancer cells at different expression levels of TROP2. For example, TROP2-positive human tumor cells such as BxPC-3 (human pancreatic cancer cell) and FaDu (human throat cancer cell), and TROP2-negative tumor cells such as HepG2 (human liver cancer cell) were selected. The results of the proliferation inhibition action of different drugs on the tumor cells are as shown in Tables 7 to 8 and FIGS. 26 to 28, where ADC-4, ADC-5 and MMAE small molecule toxins have obvious proliferation inhibition action on the positive cells, and there is no significant difference in activity between ADC-4 and ADC-5. The monoclonal antibody has no significant proliferation inhibition action on the TROP2-positive cells. ADC-4, ADC-5 and the monoclonal antibody have no inhibition action on the antigen-negative cells, which shows good targeting performance

TABLE 7

Proliferation Inhibition Action of Different Drugs on Tumor Cells (IC50, nM)

| | ADC-4 | ADC-5 | mAb-2 | MMAE |
|---|---|---|---|---|
| BxPC-3 | 0.09995 | 0.1017 | — | 0.3878 |
| FaDu | 0.1297 | 0.1121 | — | 0.1667 |
| HepG2 | — | — | — | 0.3976 |

Note:
"—" undetected

TABLE 8

Proliferation Inhibition Action of Different Drugs on Tumor Cell (the maximum killing percentage relative to the control group)

| | ADC-4 | ADC-5 | mAb-2 | MMAE |
|---|---|---|---|---|
| BxPC-3 | 98.19 | 98.21 | 6.93 | 99.56 |
| FaDu | 65.32 | 72.22 | 6.63 | 90.87 |
| HepG2 | 24.63 | 25.61 | 20.62 | 83.43 |

Note:
"—" undetected

Example 22: Preparation and Characterization of ADC-6

Figure 29:
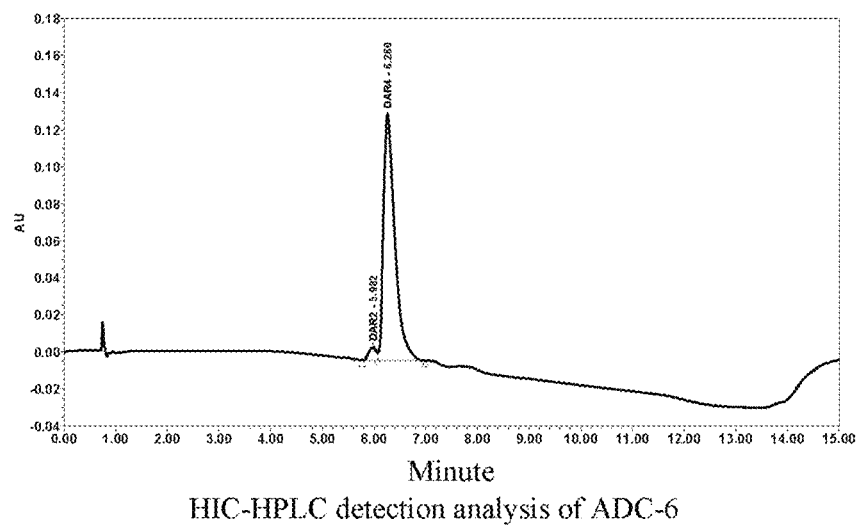
FIG. 29. HIC-HPLC analysis of ADC-6
Figure 30:
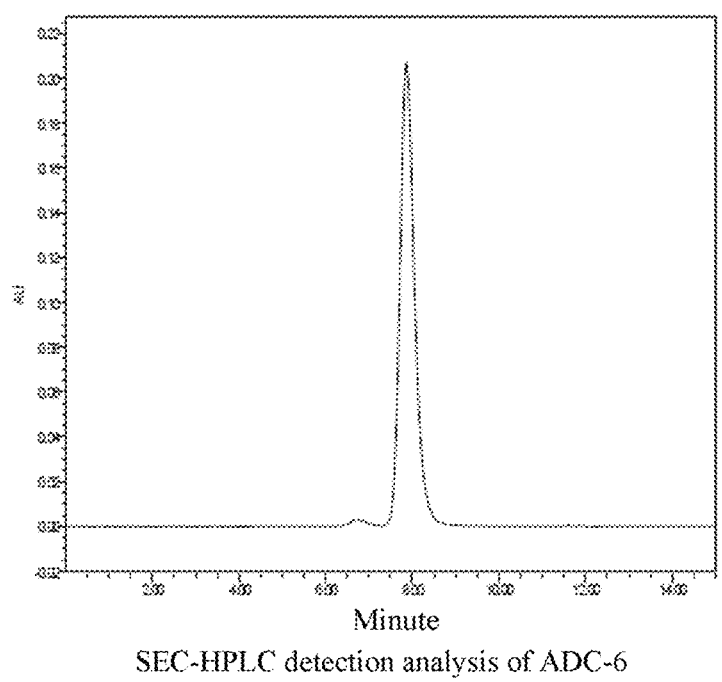
FIG. 30. SEC-HPLC analysis of ADC-6

For the preparation of ADC-6, see the method described for ADC-1 for preparation and characterization, except that the antibody used was an mAb-3 (Trastuzumab) and the linker-payload used was LP-6. The characterization data of the antibody-drug conjugate ADC-6 are described below. HIC-HPLC detection analysis of ADC-6: the detection results are as shown in FIG. 29. The antibodies unconjugated with the cytotoxin are <5%. The conjugated product is mainly DAR4, and the DAR value of overall ADC-6 is 3.93. The SEC-HPLC detection analysis of ADC-6 is as shown in FIG. 30: the high molecular weight polymer in ADC is <5%, and the ADC sample is present mainly in the form of monomers.

Example 23: In Vitro Activity Test of ADC-6 (In SK-BR-3, NCI-N87 Cells)

Figure 31:
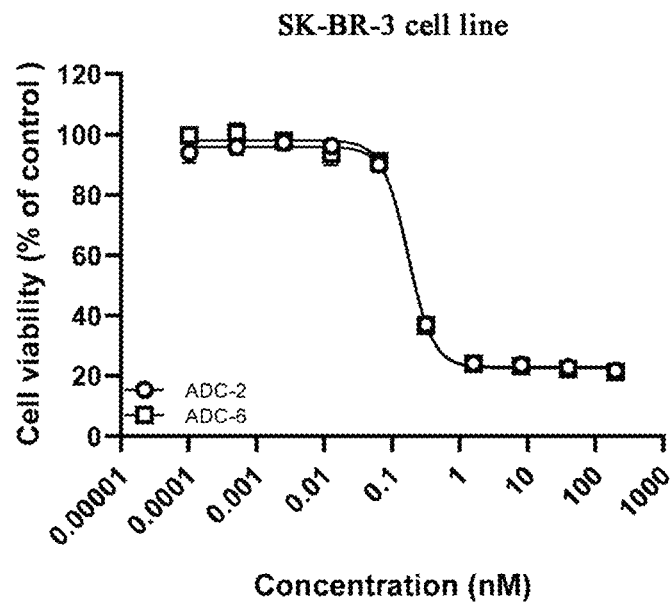
FIG. 31. In vitro inhibition activity of ADC-6 against SK-BR-3 cells
Figure 32:
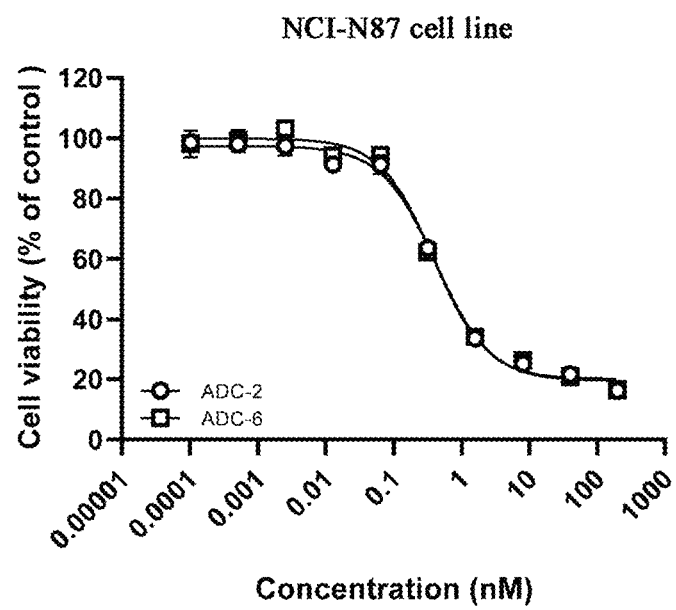
FIG. 32. In vitro inhibition activity of ADC-6 against NCI-N87 cells

Referring to the operation of the method described in Example 12, the antibody-drug conjugate ADC-6 was tested for its effect on the proliferation of cancer cells at different expression levels of HER2. For example, two groups of HER2 cell lines, SK-BR-3 and NCI-N87, were selected, and the activity differences between ADC-2 (with Srt A tag) and ADC-6 (without Srt A tag) were compared. The results show that the target ADC has no difference in the cell killing activity of the two cell lines, with or without specific recognition short peptide sequences of Srt A enzyme. See FIGS. 31 to 32

The sequences involved in this application are described below:

SEQ ID No. 1: mAb-1 Light Chain:
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECGALPETGG SEQ ID No. 2: mAb-1 Heavy Chain:
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK SEQ ID No. 3: mAb-2 Light Chain:
DIQLTQSPSSLSASVGDRVSITCKASQDVSIAVAWYQQKPGKAPKLLIY
SASYRYTGVPDRFSGSGSGTDFTLTISSLQPEDFAVYYCQQHYITPLTF
GAGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGECGALPETGG SEQ ID No. 4: mAb-2 Heavy Chain:
QVQLQQSGSELKKPGASVKVSCKASGYTFTNYGMNWVKQAPGQGLKWMG
WINTYTGEPTYTDDFKGRFAFSLDTSVSTAYLQISSLKADDTAVYFCAR
GGFGSSYWYFDVWGQGSLVTVSSASTKGPSVFPLAPSSKSTSGGTAALG
CLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVF
LFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYT
QKSLSLSPGK SEQ ID No. 5: mAb-3 Light Chain:
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC SEQ ID No. 6: mAb-3 Heavy Chain:
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSSASTKGPSVFPLAPSSKSTSGGTAALGC
LVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQ
KSLSLSPGK

What is claimed is:

1. An antibody-drug conjugate based on the site-specific conjugation at the N-glycosylation site in Fc region of an antibody, having the structure of a formula selected from the group consisting of formulas (II-1), (II-2), (II-3), (II-4) and (II-5):

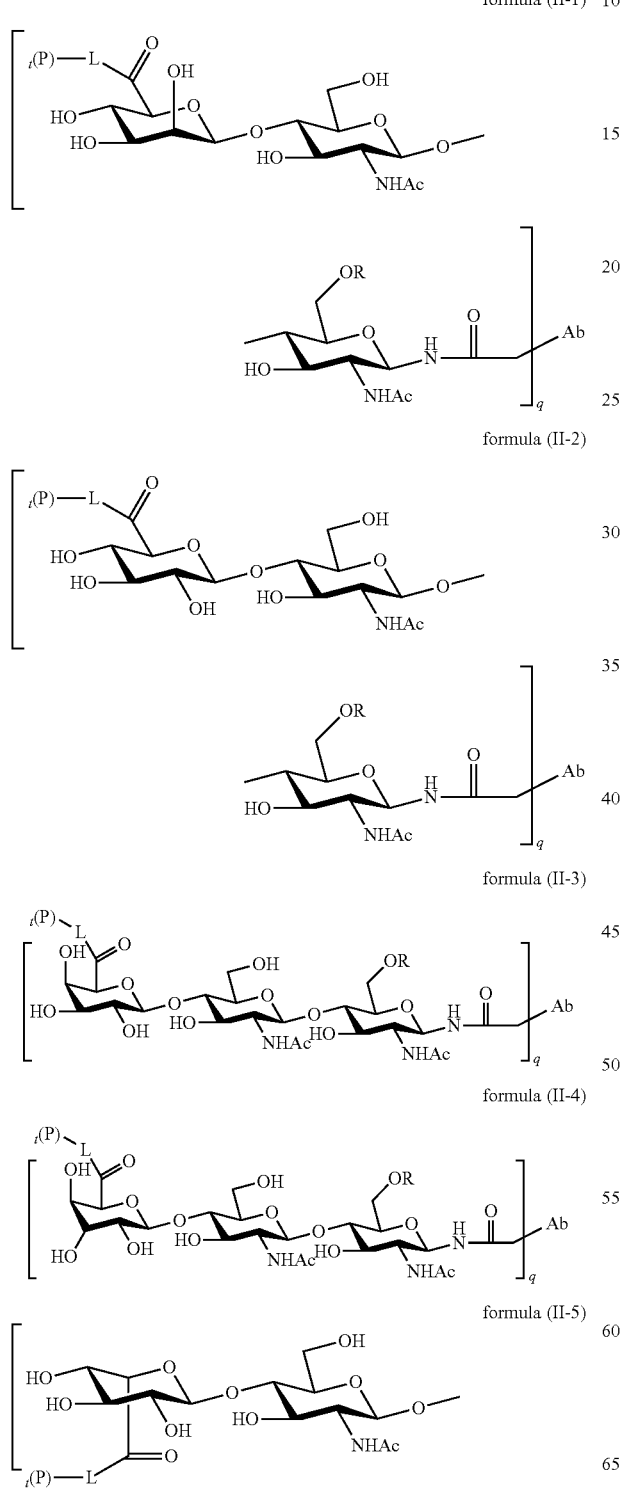

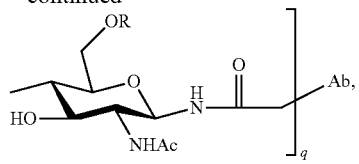

wherein
R is hydrogen or α-L-fucosyl;
q is 1 or 2;
Ab is an antibody or antigen-binding fragment thereof which contains the Fc region of the antibody, wherein the antibody is an anti-CD19 antibody, an anti-CD20 antibody, an anti-CD22 antibody, an anti-CD25 antibody, an anti-CD30/TNFRSF8 antibody, an anti-CD33 antibody, an anti-CD37 antibody, an anti-CD44v6 antibody, an anti-CD56 antibody, an anti-CD70 antibody, an anti-CD71 antibody, an anti-CD74 antibody, an anti-CD79b antibody, an anti-CD117/KITk antibody, an anti-CD123 antibody, an anti-CD138 antibody, an anti-CD142 antibody, an anti-CD174 antibody, an anti-CD227/MUC1 antibody, an anti-CD352 antibody, an anti-CLDN18.2 antibody, an anti-DLL3 antibody, an anti-ErbB2/HER2 antibody, an anti-CN33 antibody, an anti-GPNMB antibody, an anti-ENPP3 antibody, an anti-Nectin-4 antibody, an anti-EGFRvIII antibody, an anti-SLC44A4/AGS-5 antibody, an anti-CEACAM5 antibody, an anti-PSMA antibody, an anti-TIM1 antibody, an anti-LY6E antibody, an anti-LIV1 antibody, an anti-Nectin4 antibody, an anti-SLITRK6 antibody, an anti-HGFR/cMet antibody, an anti-SLAMF7/CS1 antibody, an anti-EGFR antibody, an anti-BCMA antibody, an anti-AXL antibody, an anti-*NaPi*2B antibody, an anti-GCC antibody, an anti-STEAP1 antibody, an anti-MUC16 antibody, an anti-mesothelin antibody, an anti-ETBR antibody, an anti-EphA2 antibody, an anti-5T4 antibody, an anti-FOLR1 antibody, an anti-LAMP1 antibody, an anti-Cadherin 6 antibody, an anti-FGFR2 antibody, an anti-FGFR3 antibody, an anti-CA6 antibody, an anti-CanAg antibody, an anti-integrin-aV antibody, an anti-TDGF1 antibody, an anti-ephrin A4 antibody, an anti-TROP2 antibody, an anti-PTK7 antibody, an anti-NOTCH3 antibody, an anti-C4.4A antibody, an anti-FLT3 antibody;
P is a payload selected from the group consisting of:

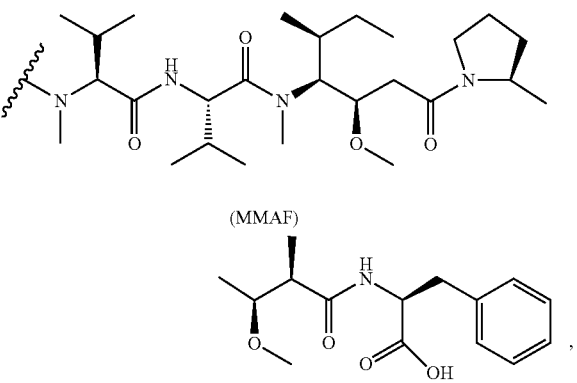

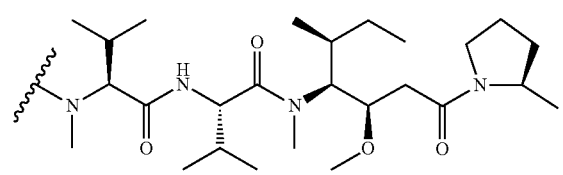
(MMAE)
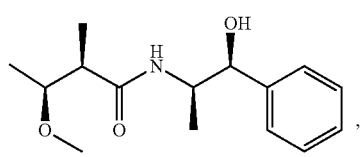
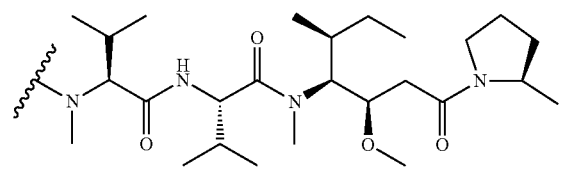
(Auristatin 0101)
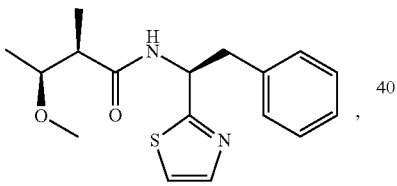
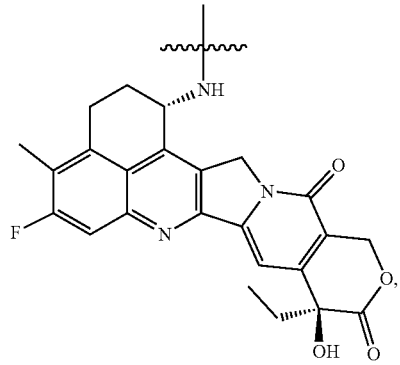
(DX8951f)
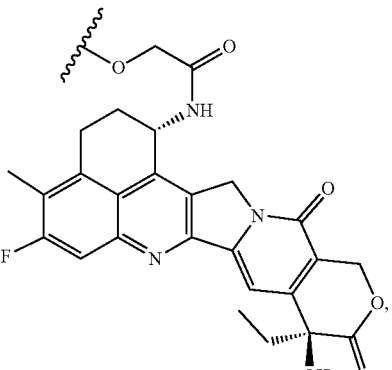
(DXd-(1))
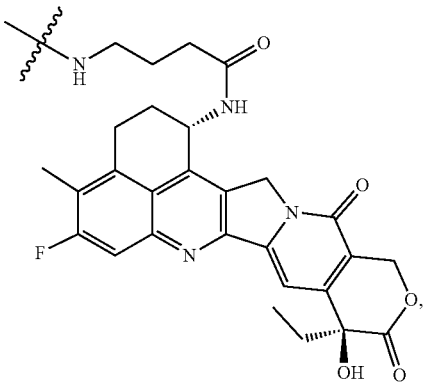
(DXD-(2))
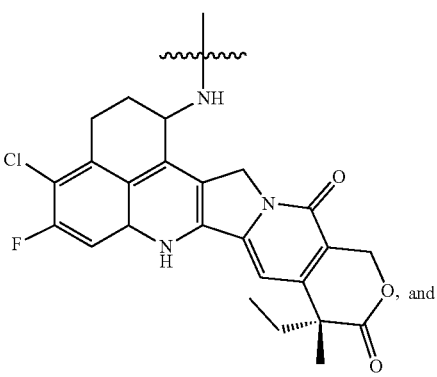
, and
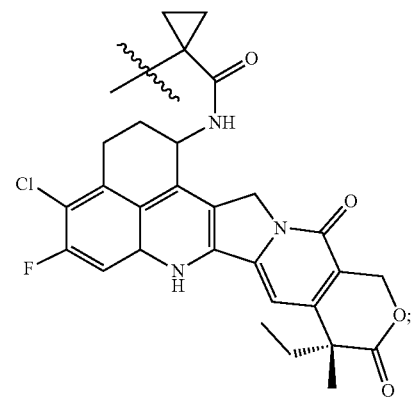

L is a linker end, L is attached to P by an amide bond or ester bond or ether bond, and L is directly attached to carbonyl in the oligosaccharide moiety via —NH— in the L to form an amide bond, wherein when L is an unbranched linker end, L is attached to one P, and t is 1, while when L is a branched linker end, each branch can be attached to one P, and t is an integer greater than 1, wherein (i) when L is an unbranched linker end, L is $L^2$-$L^1$-B or (ii) when L is a branched linker end, -L-(P)$_t$ is

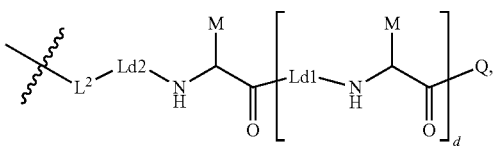

wherein

B is selected from:

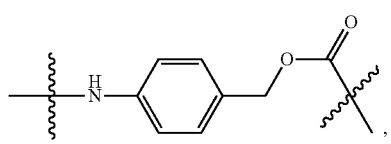
(-PABC-)

—NH—CH$_2$—U—, or —NH—CH$_2$—U—(CH$_2$)$_g$—(CO)—, where g is 1, 2, 3, 4, 5 or 6; U is absent or O;

$L^1$ is absent or selected from -Gly-Gly-Phe-Gly-, -Phe-Lys-, -Val-Cit-, -Val-Lys-, -Gly-Phe-Leu-Gly-, -Ala-Leu-Ala-Leu-, -Ala-Ala-Ala- and a combination thereof;

$L^2$ is NH—C$_{2-20}$ alkylene, wherein one or more —CH$_2$— structures in the alkylene are optionally replaced by the following groups: —O— and —(CO)—, or $L^2$ is an amino acid sequence comprising from 1 to 100 amino acids;

Ld2 and each Ld1 are independently selected from

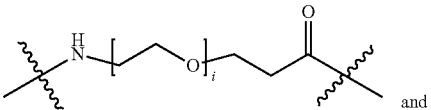 and

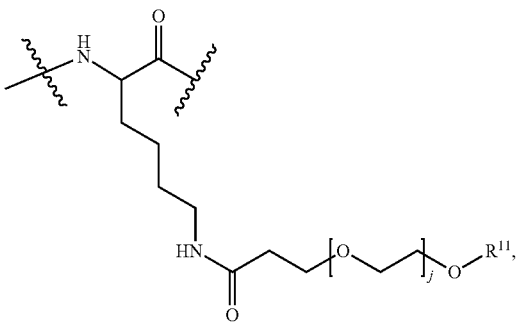

wherein each i and j are independently selected from integers from 1 to 20, and $R^{11}$ is C$_{1-10}$ alkyl;

M is LKa-$L^2$-$L^1$-B-P;

each LKa is

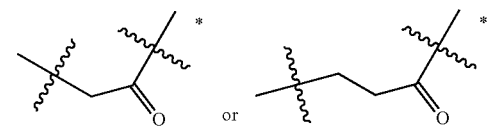 [SMILES: *CC(*)=O ; *CCC(*)=O]

where * represents a moiety attached to $L^2$;

Q is NH$_2$;

d is 1, 2, or 3.

2. The antibody-drug conjugate according to claim 1, wherein (P)$_t$-L- is selected from the group consisting of:

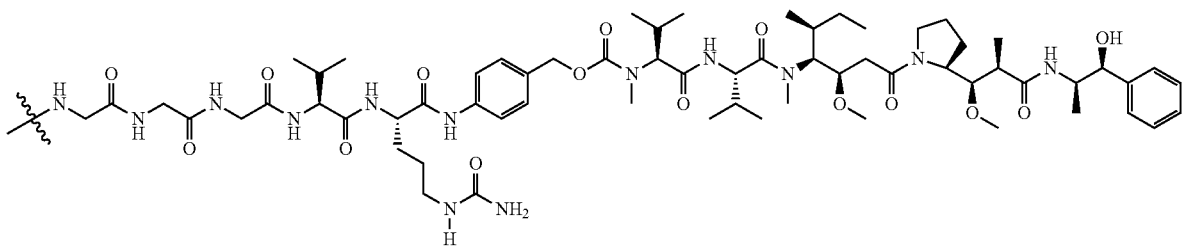

147 148
-continued
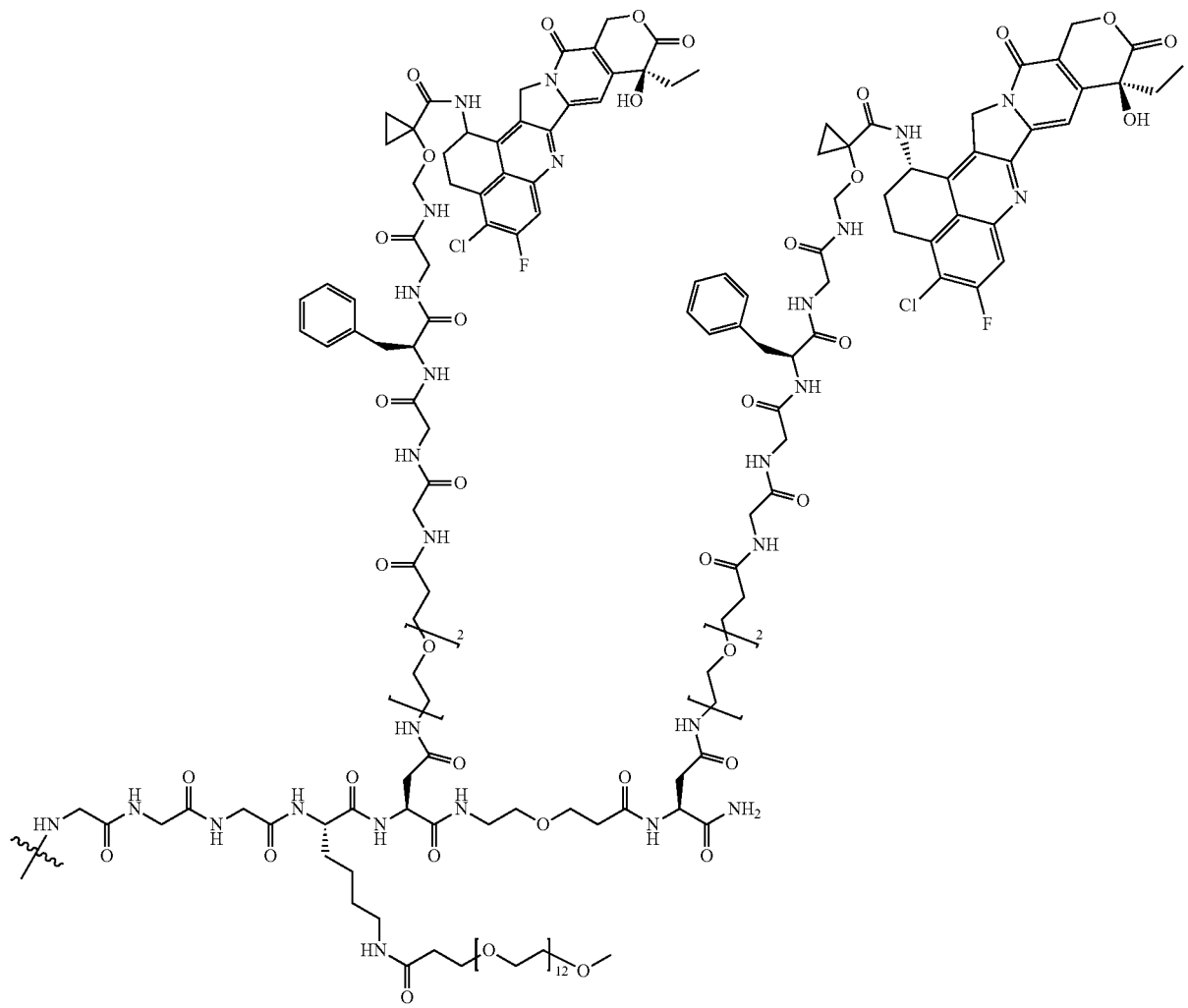

-continued

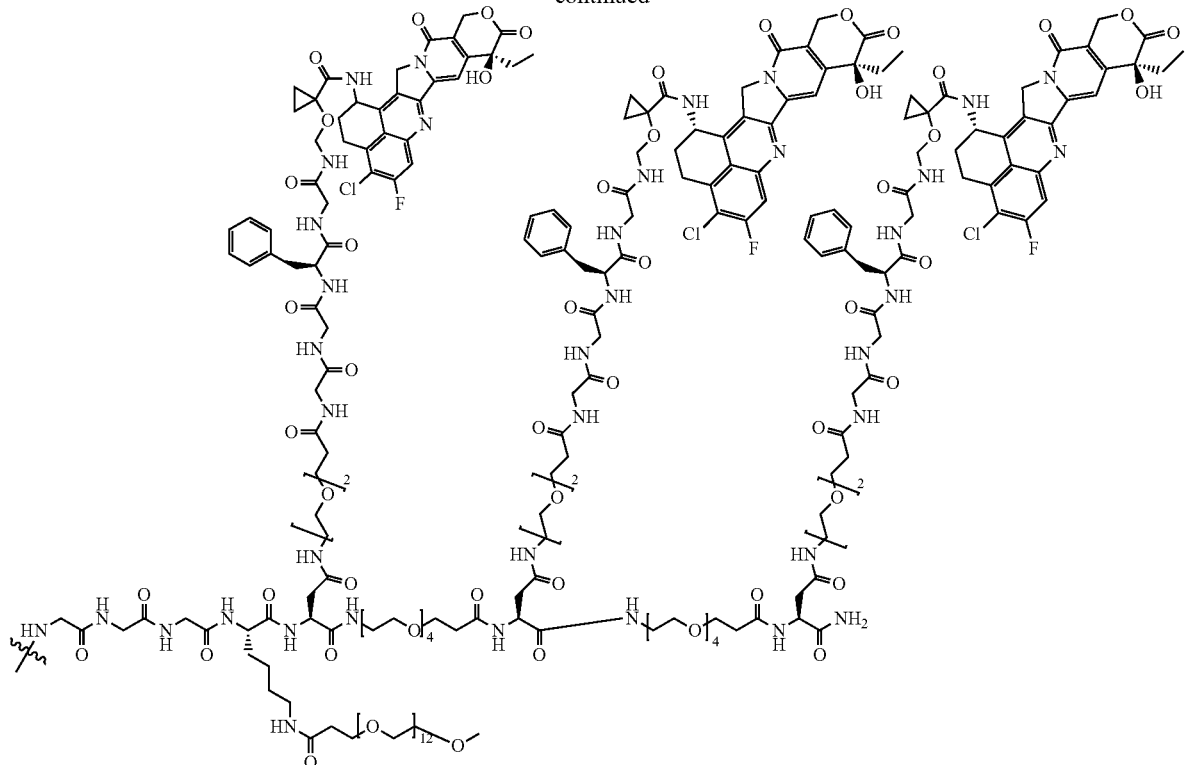

3. The antibody-drug conjugate according to claim 1, wherein the antibody-drug conjugate is obtained by a process comprising the following steps:

a) removing part of the N-glycan chain of the antibody Ab, under the catalysis of glycosidase or its mutants, to afford a remodeled antibody in which the N-glycosylation site in Fc region is N-acetylglucosamine or fucosyl-α-1,6-N-acetylglucosamine moiety;

b) conjugating the remodeled antibody obtained in step a) and a linker-payload compound having formula (I):

under the catalysis of glycosidase or its mutant, wherein $(P)_t$-L- is as defined in claim 1;

D-C(O)— is a disaccharide structure, which is a -first hexosyl or its derivative moiety-β-D-N-acetylglucosamine moiety or a -first hexosyl or its derivative moiety-β-D-glucose oxazoline moiety, wherein the first hexosyl or its derivative moiety is selected from the group consisting of

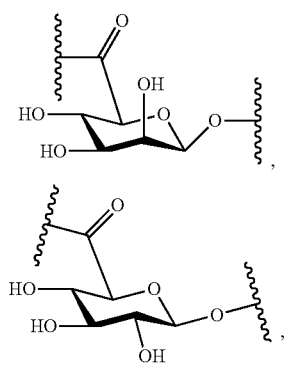

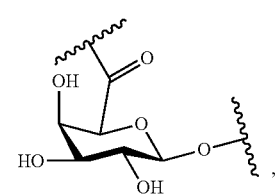

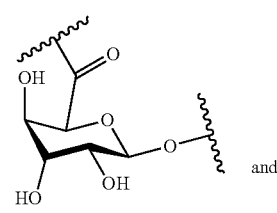

and

151

-continued

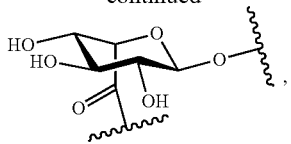

the β-D-N-acetylglucosamine moiety is

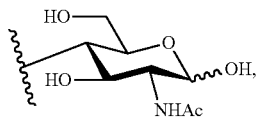

and the β-D-glucose oxazoline moiety is

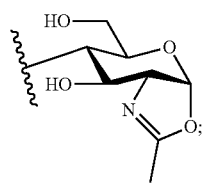

and
wherein the glycosidase or its mutant used in steps a) and b) may be the same or different.

4. A method for preparing the antibody-drug conjugate according to claim 1, comprising the following steps:
a) removing part of the N-glycan chain of the antibody Ab, under the catalysis of glycosidase or its mutants, to afford a remodeled antibody in which the N-glycosylation site in Fc region is N-acetylglucosamine or fucosyl-α-1,6-N-acetylglucosamine moiety;
b) conjugating the remodeled antibody obtained in step a) and a linker-payload compound having formula (I):

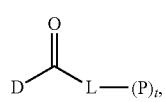

(I)

under the catalysis of glycosidase or its mutant,
wherein
(P)$_t$-L- is as defined in claim 1;
D-C(O)— is a disaccharide structure, which is a -first hexosyl or its derivative moiety-β-D-N-acetylglucosamine moiety or a -first hexosyl or its derivative moiety-β-D-glucose oxazoline moiety, wherein
the first hexosyl or its derivative moiety is selected from the group consisting of

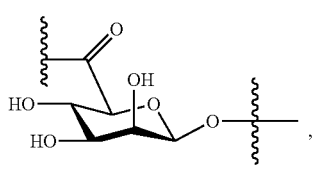

152

-continued

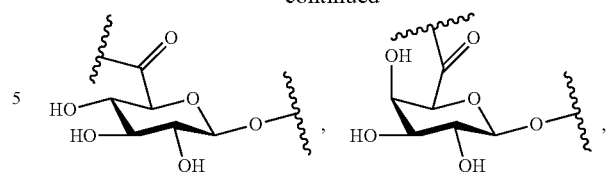

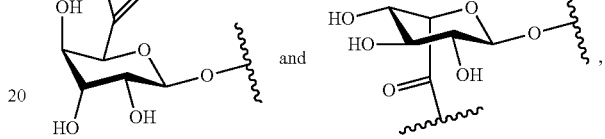

the β-D-N-acetylglucosamine moiety is

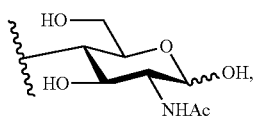

and the β-D-glucose oxazoline moiety is

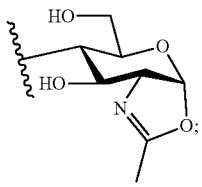

and
wherein the glycosidase or its mutant used in steps a) and b) may be the same or different.

5. The method according to claim 4, wherein the glycosidase or its mutant in steps a) and b) is fucose hydrolase, N-acetyl glucosamine endohydrolase or their mutants.

6. A pharmaceutical composition, comprising the antibody-drug conjugate according to claim 1.

7. The antibody-drug conjugate according to claim 1, wherein the antibody is an anti-ErbB2/HER2 antibody.

8. The antibody-drug conjugate according to claim 7, wherein the anti-ErbB2/HER2 antibody is Trastuzumab.

9. The antibody-drug conjugate according to claim 1, wherein R is α-L-fucosyl.

10. The antibody-drug conjugate according to claim 1, wherein the antibody-drug conjugate has the structure of formula (II-1):

formula (II-1)
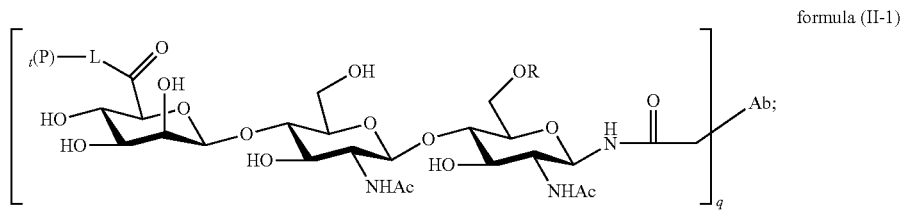
R is α-L-fucosyl; and
(P)$_t$-L- is
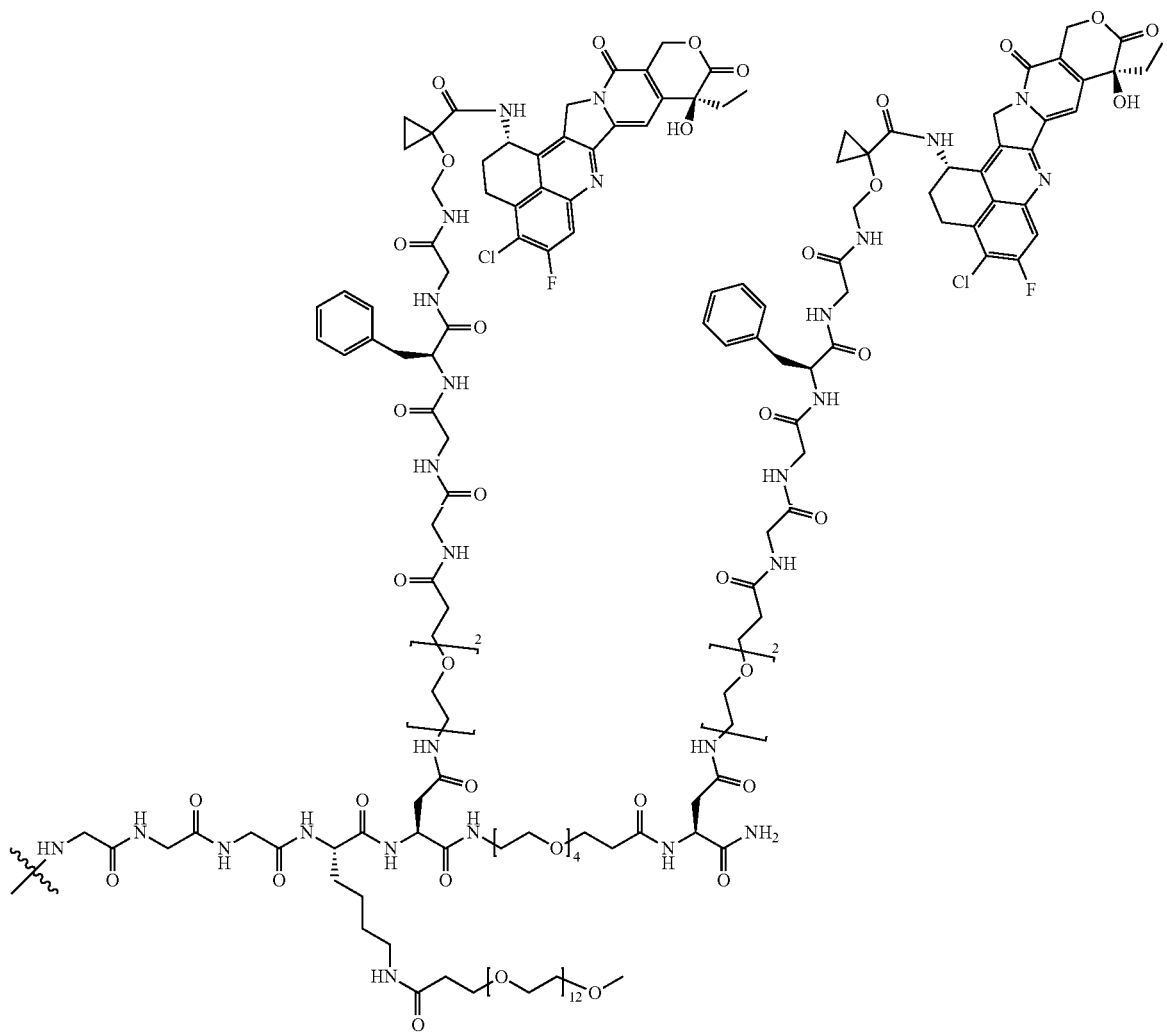
* * * * *

```
                        SEQUENCE LISTING

Sequence total quantity: 6
SEQ ID NO: 1            moltype = AA   length = 222
FEATURE                 Location/Qualifiers
source                  1..222
                        mol_type = protein
                        organism = synthetic construct
SEQUENCE: 1
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGECGALPET GG                     222

SEQ ID NO: 2            moltype = AA   length = 450
FEATURE                 Location/Qualifiers
source                  1..450
                        mol_type = protein
                        organism = synthetic construct
SEQUENCE: 2
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
```

```
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 3            moltype = AA  length = 222
FEATURE                 Location/Qualifiers
source                  1..222
                        mol_type = protein
                        organism = synthetic construct
SEQUENCE: 3
DIQLTQSPSS LSASVGDRVS ITCKASQDVS IAVAWYQQKP GKAPKLLIYS ASYRYTGVPD    60
RFSGSGSGTD FTLTISSLQP EDFAVYYCQQ HYITPLTFGA GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGALPET GG                      222

SEQ ID NO: 4            moltype = AA  length = 451
FEATURE                 Location/Qualifiers
source                  1..451
                        mol_type = protein
                        organism = synthetic construct
SEQUENCE: 4
QVQLQQSGSE LKKPGASVKV SCKASGYTFT NYGMNWVKQA PGQGLKWMGW INTYTGEPTY    60
TDDFKGRFAF SLDTSVSTAY LQISSLKADD TAVYFCARGG FGSSYWYFDV WGQGSLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAGGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                   451

SEQ ID NO: 5            moltype = AA  length = 214
FEATURE                 Location/Qualifiers
source                  1..214
                        mol_type = protein
                        organism = synthetic construct
SEQUENCE: 5
DIQMTQSPSS LSASVGDRVT ITCRASQDVN TAVAWYQQKP GKAPKLLIYS ASFLYSGVPS    60
RFSGSRSGTD FTLTISSLQP EDFATYYCQQ HYTTPPTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                                214

SEQ ID NO: 6            moltype = AA  length = 450
FEATURE                 Location/Qualifiers
source                  1..450
                        mol_type = protein
                        organism = synthetic construct
SEQUENCE: 6
EVQLVESGGG LVQPGGSLRL SCAASGFNIK DTYIHWVRQA PGKGLEWVAR IYPTNGYTRY    60
ADSVKGRFTI SADTSKNTAY LQMNSLRAED TAVYYCSRWG GDGFYAMDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450
```